(12) United States Patent
Wang et al.

(10) Patent No.: US 11,944,677 B2
(45) Date of Patent: *Apr. 2, 2024

(54) CHIMERIC VIRUS-LIKE PARTICLES AND USES THEREOF AS ANTIGEN-SPECIFIC REDIRECTORS OF IMMUNE RESPONSES

(71) Applicant: VERIMMUNE INC., Washington, DC (US)

(72) Inventors: Joshua Weiyuan Wang, Alexandria, VA (US); Nattha Ingavat, Bangkok (TH)

(73) Assignee: VERIMMUNE INC., Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/704,933

(22) Filed: Mar. 25, 2022

(65) Prior Publication Data

US 2022/0226460 A1 Jul. 21, 2022

Related U.S. Application Data

(63) Continuation of application No. 16/626,281, filed as application No. PCT/US2018/038701 on Jun. 21, 2018, now Pat. No. 11,285,203.

(60) Provisional application No. 62/676,566, filed on May 25, 2018, provisional application No. 62/524,308, filed on Jun. 23, 2017.

(51) Int. Cl.
| | |
|---|---|
| A61K 39/12 | (2006.01) |
| A61K 39/29 | (2006.01) |
| A61K 45/06 | (2006.01) |
| A61P 35/00 | (2006.01) |
| C07K 14/005 | (2006.01) |
| C12N 7/00 | (2006.01) |
| A61K 39/00 | (2006.01) |

(52) U.S. Cl.
CPC ............ *A61K 39/12* (2013.01); *A61K 39/292* (2013.01); *A61K 45/06* (2013.01); *A61P 35/00* (2018.01); *C07K 14/005* (2013.01); *C12N 7/00* (2013.01); *A61K 2039/5258* (2013.01); *A61K 2039/585* (2013.01); *C12N 2710/16722* (2013.01); *C12N 2710/16723* (2013.01); *C12N 2710/16734* (2013.01); *C12N 2710/20023* (2013.01); *C12N 2710/20034* (2013.01); *C12N 2730/10023* (2013.01); *C12N 2730/10134* (2013.01); *C12N 2760/16022* (2013.01); *C12N 2760/16023* (2013.01); *C12N 2760/16034* (2013.01)

(58) Field of Classification Search
CPC ...... A61K 2039/5258; A61K 2039/585; A61K 39/12; A61K 2039/545; A61K 2039/627; A61K 35/17; A61K 35/76; A61K 35/768; A61K 38/162; A61K 39/02; A61K 39/292; A61K 39/39; A61K 45/06; A61K 9/107; A61P 35/00; A61P 31/12; C07K 14/005; C12N 2710/20023; C12N 2710/16723; C12N 2710/16734; C12N 2710/20034; C12N 2760/16034; C12N 2760/16023; C12N 2760/16022; C12N 2730/10023; C12N 2760/00034; C12N 2760/00023; C12N 2730/00034; C12N 2710/20011

See application file for complete search history.

(56) References Cited

U.S. PATENT DOCUMENTS

| | | | |
|---|---|---|---|
| 7,521,209 B2 | 4/2009 | Brown | |
| 8,062,642 B1 | 11/2011 | Rose et al. | |
| 8,168,190 B2 | 5/2012 | Murray | |
| 9,045,727 B2 | 6/2015 | Compans et al. | |
| 9,149,503 B2 | 10/2015 | Roden et al. | |
| 9,580,474 B2 | 2/2017 | Viscidi et al. | |
| 9,855,347 B2 | 1/2018 | De Los Pinos et al. | |
| 10,117,947 B2 | 11/2018 | De Los Pinos et al. | |
| 10,688,172 B2 | 6/2020 | Coursaget et al. | |
| 10,933,129 B2 | 3/2021 | Altreuter et al. | |
| 11,285,203 B2 * | 3/2022 | Wang | A61K 39/12 |
| 11,506,408 B2 * | 11/2022 | Uhlik | F24F 8/10 |
| 2002/0039584 A1 | 4/2002 | Hallek et al. | |
| 2004/0209295 A1 | 10/2004 | Schwabe et al. | |
| 2004/0223976 A1 | 11/2004 | Bianchi et al. | |
| 2005/0118191 A1 * | 6/2005 | Robinson | C07K 14/005 |
| | | | 435/235.1 |
| 2005/0142115 A1 | 6/2005 | Qiao et al. | |
| 2007/0104689 A1 | 5/2007 | Gillies et al. | |
| 2007/0160628 A1 | 7/2007 | Birkett et al. | |
| 2007/0184473 A1 | 8/2007 | Shirwan et al. | |

(Continued)

FOREIGN PATENT DOCUMENTS

| | | |
|---|---|---|
| CN | 102153656 A | 8/2011 |
| EP | 2416798 B1 | 9/2017 |

(Continued)

OTHER PUBLICATIONS

Holx et al. Antiviral Res. Feb. 2015 114, 96-105.*

(Continued)

*Primary Examiner* — Bao Q Li
(74) *Attorney, Agent, or Firm* — BioPharma Law Group, PLLC

(57) ABSTRACT

This invention relates to chimeric virus-like particles (VLPs) assembled from a polypeptide comprising a papilloma virus (PV) L1 protein or L1/L2 protein and a target peptide comprising a CD8+ T cell epitope derived from a human pathogen. This invention also relates to methods using the chimeric VLPs as antigen-specific redirectors of immune responses.

14 Claims, 9 Drawing Sheets

Specification includes a Sequence Listing.

(56) References Cited

U.S. PATENT DOCUMENTS

| | | |
|---|---|---|
| 2010/0092504 A1 | 4/2010 | Rose et al. |
| 2010/0111995 A1 | 5/2010 | Bachman et al. |
| 2010/0135902 A1 | 6/2010 | Roberts et al. |
| 2010/0172936 A1 | 7/2010 | Lowy et al. |
| 2010/0260792 A1 | 10/2010 | Murata et al. |
| 2014/0050753 A1 | 2/2014 | Viscidi et al. |
| 2014/0099337 A1 | 4/2014 | Davis et al. |
| 2015/0231239 A1 | 8/2015 | Hung et al. |
| 2016/0058852 A1 | 3/2016 | Ter Meulen et al. |
| 2017/0152316 A1 | 6/2017 | Cobbold |
| 2017/0274099 A1 | 9/2017 | De Los Pinos et al. |
| 2017/0327543 A1 | 11/2017 | Viscidi et al. |
| 2018/0078655 A1 | 3/2018 | Dziadek et al. |
| 2018/0104320 A1 | 4/2018 | Gravekamp |
| 2018/0110883 A1 | 4/2018 | De Los Pinos et al. |
| 2018/0193382 A1 | 7/2018 | Barrat |
| 2018/0311269 A1 | 11/2018 | Lobb et al. |
| 2018/0311374 A1 | 11/2018 | Lobb et al. |
| 2018/0325952 A1 | 11/2018 | Masopust, Jr. et al. |
| 2019/0022206 A1 | 1/2019 | Pedersen et al. |
| 2019/0117760 A1 | 4/2019 | Graham et al. |
| 2020/0121779 A1 | 4/2020 | Garcea et al. |
| 2020/0164054 A1 | 5/2020 | Snyder et al. |

FOREIGN PATENT DOCUMENTS

| | | |
|---|---|---|
| JP | H10506796 A | 7/1998 |
| JP | 2008543810 A | 12/2008 |
| WO | 96/11274 A1 | 4/1996 |
| WO | 99/50424 A1 | 10/1999 |
| WO | 01/23422 A1 | 4/2001 |
| WO | 2008154868 A1 | 12/2008 |
| WO | 2009055491 A2 | 4/2009 |
| WO | 2010/001409 A2 | 1/2010 |
| WO | 2010/118424 A1 | 10/2010 |
| WO | 2012/033911 A2 | 3/2012 |
| WO | 2012/123755 A1 | 9/2012 |
| WO | 2013080187 A1 | 6/2013 |
| WO | 2014043523 A1 | 3/2014 |
| WO | 2014145932 A1 | 9/2014 |
| WO | 2016112921 A1 | 7/2016 |
| WO | 2016176164 A1 | 11/2016 |
| WO | 201720570 A1 | 2/2017 |
| WO | 2017/075615 A1 | 5/2017 |
| WO | 2017/079747 A1 | 5/2017 |
| WO | 2017087789 A1 | 5/2017 |
| WO | 2017/112830 A1 | 6/2017 |
| WO | 2017/177204 A1 | 10/2017 |
| WO | 2018/106972 A1 | 6/2018 |
| WO | 2019/028406 A1 | 2/2019 |
| WO | 2019/090304 A1 | 5/2019 |
| WO | 2020017962 A1 | 1/2020 |
| WO | 2020198344 A1 | 10/2020 |

OTHER PUBLICATIONS

Huber, B., et al., "Chimeric L2-based virus-like particle (VLP) vaccines targeting cutaneous human papillomaviruses (HPV).", PLOS One, Jan. 5, 2017, vol. 12, No. 1, e0169533, pp. 1-27.
Plummer, E.M., et al., "Viral nanoparticles and virus-like particles: platforms for contemporary vaccine design.", Wires Nanomedicine and Nano Biotechnology, Sep. 24, 2010, vol. 3, No. 2, pp. 174-196.
JPO Notice of Reasons for Rejection dated Jun. 28, 2022, Japanese Application No. 2020-520192, pp. 1-9.
Eurasian Office Action dated Mar. 24, 2022, Eurasian Patent Application No. 202090030, pp. 1-3 (English Translation of Original Office Action).
Extended European Search Report dated Aug. 30, 2022, European Application No. 19903832.4, pp. 1-8.
Martin Muller et al., "Chimeric Papillomavirus-like Particles," Virology, vol. 234, Article No. VY978591, 1997, pp. 93-111.
Mark T. Wakabayashi et al., "Comparison of Human Papillomavirus Type 16L1 Chimeric Virus-Like Particles versus L1/L2 Chimeric Virus-Like Particles in Tumor Prevention," Intervirology, vol. 45, 2002, pp. 300-307.
Joshua W. Wang et al., "Virus-like particles for the prevention of human papillomavirus-associated malignancies." Expert review of vaccines 12.2 (2013): 129-141.
Singapore Search Report and Written Opinion dated Mar. 15, 2023, Singapore Patent Application No. 11202106931P, pp. 1-9.
Japanese Pre-Trial Examination Report dated Aug. 29, 2023, Japanese Application No. 2020-520192, pp. 1-2.
National Cancer Institute, What is Cancer?, https://www.cancer.gov/about-cancer/understanding/what-is-cancer accessed May 8, 2020 (Year: 2015).
National Cancer Institute, Cancer Prevention, https://www.cancer.gov/about-cancer/causes-prevention/patient-prevention-overview-pdq accessed May 8, 2020 (Year: 2020).
Merck Manual, Cancer Treatment Principles, by Robery Gale, https://www.merckmanuals.com/home/cancer/prevention-and-treatment-of-cancer/cancer-treatment-principles?query=Cancer%20treatment accessed May 8, 2020 (Year: 2018).
Merck Manual, Overview of Cancer Therapy, by Robert Gale, https://www.merckmanuals.com/professional/hematology-and-oncology/principles-of-cancer-therapy/overview-of-cancer-theray?query=Cancer assessed May 8, 2020 (Year: 2018).
Medical News Today by Christina Chun, https://www.medicalnewstoday.com/articles/322700 accessed May 8, 2020 (Year: 2018).
Xiaojiang S. Chen et al., "Structure of Small Virus-like Particles Assembled from the L1 Protein of Human Papillomavirus 16", Molecular Cell, vol. 5, Mar. 2000, pp. 557-567.
Jeffrey I. Cohen, "Epstein-barr virus vaccines", Clinical & Transitional Immunology, vol. 4, No. 4, 2015, pp. 1-6.
Christopher P. Fox et al., "A novel latent membrane 2 transcript expressed in Epstein-Barr virus-positive NK- and T-cell lymphoproliferative disease encodes a target for cellular immunotherapy", Blood Journal, vol. 116, No. 19, Nov. 11, 2010, pp. 3695-3704.
Gregson et al., "Phase I trail of an alhydrogel adjuvanted hepatitis B core virus-like particle containing epitopes of Plasmodium falciparum circumsporozoite protein", PLoS One, 3(2), Feb. 6, 2008, p. e1556 (Abstract Submitted).
PCT International Search Report and Written Opinion dated Dec. 12, 2018, International Application No. PCT/US2018/038701, pp. 1-19.
Wen Jun Liu et al., "Papillomavirus Virus-like Particles for the Delivery of Multiple Cytotoxic T Cell Epitopes", Virology, vol. 273, 2000, pp. 374-382.
Slavica Matic et al., "Efficient production of chimeric Human papillomavirus 16 L1 protein bearing the M2e influenza epitope in Nicotiana benthamiana plants", BMC Biotechnology, 11:106, 2011, pp. 1-12.
Cuburu Nicolas et al., "Harnessing pre-existing anti-viral immunity for tumor therapy", SITC 2019, Retrieved from the Internet on Nov. 11, 2019: www.sitcancer.org, pp. 920-921.
Sharmila Pejawar-Gaddy et al., "All in one: VLP-MUC1 vaccine for prevention and treatment of epithelial tumors", The FASEB Journal, vol. 22, No. 1_supplement, Mar. 2008, pp. 1077-7 (Abstract Submitted).
John T. Schiller et al., "Papillomavirus-like particle based vaccines: cervical cancer and beyond", Expert Opinion on Biological Therapy, vol. 1, No. 4, Aug. 2001, pp. 571-581.
Julian P. Sefrin et al., "Sensitization of Tumors for Attack by Virus-Specific CD8+ T-Cells Through Antibody-Mediated Delivery of Immunogenic T-Cell Epitopes", Frontiers in Immunology, vol. 10, Article 1962, Aug. 2019, pp. 1-14.
Katharina Slupetzky et al., "Chimeric papillomavirus-like particles expressing a foreign epitope on capsid surface loops", Journal of General Virology, vol. 82, Issue 11, Nov. 2001, pp. 2799-2804.
Susan Thrane et al., "A Novel Virus-like Particle Based Vaccine Platform Displaying the Placental Malaria Antigen VAR2CSA", PLoS One, 10(11), Nov. 23, 2015, pp. 1-16.
S. Kirk Wright et al., "Evaluation of methods for the quantitation of cysteines in proteins", Analytical Biochemistry, vol. 265, Issue 1, Dec. 1, 1998, pp. 8-14 (Abstract Submitted).

(56) References Cited

OTHER PUBLICATIONS

David G. Millar et al., "Anti-body mediated delivery of viral epitopes to tumors harnesses CMV-specific T cells for cancer therapy", Nature Biotechnology, 2020, pp. 1-6.
Andreas M. Kaufmann et al., "Vaccination trial with HPV16 L1E7 chimeric virus-like particles in women suffering from high grade cervical intraepithelial neoplasia (CIN 2/3)", International Journal of Cancer, 121(12), Dec. 2007, pp. 2794-2800.
PCT International Search Report and Written Opinion dated Mar. 10, 2020, International Application No. PCT/US2019/068619, pp. 1-24.
Deepali G. Vartak et al., "Matrix metalloproteases: Underutilized targets for drug delivery," Journal of Drug Targeting, Jan. 2007, 15(1), pp. 1-20.
Marion Braun et al., "Virus-like particles induce robust human T-helper cell responses," European Journal of Immunology, 2012, 42: pp. 330-340.
Extended European Search Report dated Mar. 18, 2021, European Application No. 18820136.2, pp. 1-7.
R. Kirnbauer et al., "Virus-like particles of bovine papillomavirus type 4 in prophylactic and therapeutic immunization." Virology 219.1 (1996): 37-44.
Stefania Bellone et al., "Human papillomavirus type 16 (HPV-16) virus-like particle L1-specific CD8+ cytotoxic T lymphocytes (CTLs) are equally effective as E7-specific CD8+ CTLs in killing autologous HPV-16-positive tumor cells in cervical cancer patients: implications for L1 dendritic cell-based therapeutic vaccines." Journal of virology 83.13 (2009): 6779-6789.

\* cited by examiner

CHIMERIC VIRUS-LIKE PARTICLES AND USES THEREOF AS ANTIGEN-SPECIFIC REDIRECTORS OF IMMUNE RESPONSES

This application is a continuation of U.S. patent application Ser. No. 16/626,281 filed Dec. 23, 2019, which is a U.S. national stage application of international application no. PCT/US2018/038701 filed Jun. 21, 2018, which claims the benefit of priority U.S. provisional application No. 62/676,566 filed May 25, 2018 and U.S. provisional application No. 62/524,308 filed Jun. 23, 2017, incorporated herein in their entirety by reference.

FIELD OF THE INVENTION

This invention relates to chimeric virus-like particles (VLPs) assembled from a chimeric polypeptide comprising a papilloma virus (PV) L1 protein or L1/L2 protein comprising a CD8+ T cell epitope-containing peptide(s) derived from a human pathogen(s), compositions comprising such chimeric VLPs and therapeutic uses of the chimeric VLPs in the redirection and stimulation of both innate and adaptive immunity for the treatment of cancers.

BACKGROUND

According to the National Cancer Institute, the overall rate of cancer deaths continue to decrease: the overall cancer incidence rates have declined in men and have stabilized in women. The five year survival has also improved for most but not all common cancers. And yet it is estimated that in 2017 there will be an additional 1,688,780 new cancer cases diagnosed and 600,920 cancer deaths in the US alone.

Cytotoxic CD8+ T lymphocytes (often called cytotoxic T lymphocytes, or CTLs) can selectively kill cancer cells and thus antigen-specific immunotherapy based on tumor associated antigens has been pursued as a promising methodology to control tumors. Attempts have been made to use such immunotherapy to stimulate the immune system and specifically target and eliminate tumor cells. Such therapies are attractive in that they are target specific, and potentially less toxic without nonspecific autoimmunity. They are also considered less invasive or traumatic compared to surgery, radiation or chemotherapy. However, cancer vaccines based on tumor associated antigens have had to date limited success due to poor clinical immunogenicity, immune tolerance, and poor clinical outcome. Moreover, such methods typically require identifying a tumor associated antigen to specifically target the tumor. Furthermore, there is a growing appreciation that the tumor micro-environment can comprise immunosuppressive factors, e.g., checkpoint (CP) proteins, e.g., PD-1/PD-L1, CTLA-4/(B7-1/B7-2), CD86, GITR, LAG3, VISTA, TIGIT and CD137L, that can inhibit T cells from killing cancer cells. CP proteins can impair either the inductive or effector phase of the immune response induced by directed antigen immunotherapy efforts. To overcome such immunosuppression, immune CP inhibitors have been used to block CP proteins and rescue impaired tumor antigen specific T-cells in the tumor microenvironment making them better able to kill cancer cells. While ground breaking, the responder rate of CP inhibitors is about 30% at best, as their efficacy requires the existence of an anti-tumor specific immune response. Thus there is still a need for compositions and methods that produce or harness existing strong durable T-cell responses to inhibit tumor growth, progression, and metastasis.

BRIEF DESCRIPTION OF THE INVENTION

The present invention is directed to a chimeric virus-like particle (VLP) assembled from a polypeptide comprising a papilloma virus (PV) L1 protein, a recombinant PV L1 protein or a PV L1 protein and L2 protein. The chimeric VLP of this invention also comprises a target peptide(s). A target peptide as defined herein comprises a T cell epitope recognized by a pre-existing memory CD8+ T cell. In an embodiment of this invention the chimeric VLP of this invention comprises a target peptide(s) that is surface displayed. In some embodiments the target peptide is attached, or conjugated, to the surface of the VLP and in some embodiments the target peptide is inserted recombinantly into the L1 or L2 protein such that the target peptide is displayed on the surface of the assembled VLP. The target peptide comprises a T cell epitope from another human pathogen and in some embodiments the target peptide is not a peptide of a papilloma virus. In some embodiments the target peptide does not comprise a murine E7 epitope (aa49-57). The invention is also directed to compositions comprising the inventive chimeric VLPs, and methods for using the chimeric VLPs in the treatment of cancer.

In an aspect of the invention the target peptide is derived from a human pathogen, e.g., a virus, a bacteria, a fungus, or a parasite, and is not a tumor associated antigen. The virus includes without limitation, a vaccinia virus, varicella zoster virus, an adenovirus, an arbovirus, Epstein-barr virus, a coronavirus, a cytomegalovirus, a Coxsakie virus, a Herpes zoster virus, rubella, a hepatitis virus, e.g., hepatitis A virus or hepatitis B virus, or hepatitis C virus, herpes simplex virus type 1 or type 2, a JC virus, an influenza type A or type B, a measles virus, a mumps virus, a parainfluenza virus, a poliovirus, a variola (smallpox) virus, a rabies virus, a respiratory syncytial virus, a rhinovirus, a rotavirus, dengue virus, ebola virus, west nile virus, a yellow fever virus, or a zika virus.

In an aspect of this invention the VLP is assembled from L1 proteins of any member of the Papillomaviridae family. In an aspect of the invention the papilloma L1 protein is an L1 protein of an animal papilloma virus (e.g. Cotton Rabbit PV, Mouse PV, or Bovine PV) or a human PV (HPV), e.g., HPV 16, HPV18, HPV5, HPV31, etc. In an aspect of the invention the papilloma L1 protein is an L1 protein of a Bovine (BPV) or a HPV. In an aspect of this invention the VLP is a RG1-VLP. RG1-VLP is assembled from an HPV 16 L1 protein which is modified to present HPV16 L2 amino acids 17-36 (RG1 epitope) within the DE-surface loop of HPV16 L1 (Schellenbacher et al. 2013 *J. Invest Dermatol;* 133(12):2706-2713; Slupetzky et al., 2007 *Vaccine* 25:2001-10; Kondo et al. 2008 *J. Med. Virol* 80; 841-6; Schellenbacher et al. 2009 *J. Virol* 83:10085-95; Caldeira et al. 2010 *Vaccine* 28:4384-93.)

In an aspect of the invention the target peptide is attached to the VLP. In an aspect of the invention either the N-terminus or C-terminus of the target peptide is conjugated to an amino acid residue on the surface of the VLP. The surface residue may be for example a cysteine, a lysine or an arginine. Many methods for conjugating a peptide to a protein are known in the art, see e.g., *Bioconjugate Techniques,* 3rd Edition (2013) Author, Greg T. Hermanson, Ionescu et al. *Journal of Pharmaceutical Sciences,* January 2006, 95(1):70-79, and Jones et al., *Journal of the American Chemical Society,* 2012, 134:1847-1852, all incorporated herein by reference for disclosure of such methods.

In an aspect of this invention the VLP is assembled from papillomavirus L1 protein or L1 protein and L2 protein, then subjected to reducing conditions sufficient to reduce the disulfide bonds to sulfhydryl groups of cysteine residues in the VLP while maintaining the capsid-like icosahedron structure of the VLP and the target peptide is conjugated to the sulfhydryl group via a disulfide linkage or a maleimide linkage. In an embodiment of this invention the cysteine is on the surface of the VLP. In an aspect of this invention the target peptide is conjugated to a sulfhydryl group of a cysteine of the L1 protein of the VLP. In an aspect of this invention the target peptide is conjugated to a sulfhydryl group of a cysteine of the L2 protein of the VLP. In an aspect of the invention the cysteine is not part of a polyionic: cysteine, a polycationic:cysteine or a polyanionic:cysteine, sequence. In an aspect of this invention the VLP is assembled from papillomavirus L1 protein or L1 protein and L2 protein and the target peptide is conjugated to the sulfhydryl group of a cysteine of the assembled VLP via a disulfide linkage or a maleimide linkage wherein the conjugation reaction is performed under a nitrogen atmosphere. In an embodiment of this invention the cysteine is on the surface of the VLP.

In an aspect of this invention the VLP is assembled from papillomavirus L1 protein, or L1 protein and L2 protein and then subjected to environmental conditions of basic pH while maintaining the capsid-like icosahedron structure of the VLP and the target peptide with a maleimide group at the N-terminus is conjugated to a primary amine on a lysine and/or a guanidyl group on an arginine residue of the VLP via 1-4 addition reaction. In an embodiment of this invention the lysine and/or the arginine are on the surface of the VLP.

In an aspect of this invention the VLP is assembled from papillomavirus L1 protein, or L1 protein and L2 protein, then subjected environmental conditions of a basic pH, while maintaining the capsid-like icosahedron structure of the VLP, and the target peptide with a di-bromo or di-iodo maleimide group at its N-terminus is conjugated to a primary amine group on a lysine residue and/or a guanidyl group on an arginine residue of the VLP via 1-4 addition reaction. In an embodiment of this invention the lysine and/or the arginine are on the surface of the VLP.

In an aspect of this invention the VLP is assembled from papillomavirus L1 protein, or L1 protein and L2 protein, then subjected to environmental conditions of physiologic to basic pH, while maintaining the capsid-like icosahedron structure of the VLP, and the N-protected target peptide with N-hydroxysuccinimide ester group at the C-terminus is conjugated to a primary amine group on a lysine residue and/or a guanidyl group on an arginine residue on the VLP via amide formation. In an embodiment of this invention the lysine and/or the arginine are on the surface of the VLP.

In an aspect of the invention the target peptide is attached to a loop of the PV L1 protein, e.g., a BC, CD, DE, EF, FG, or HI loop. In an aspect of the invention the target peptide is attached to the DE loop, the H1 loop, or a helix B4 loop of an HPV L1 protein. In an aspect of the invention the target is attached to the helix B4 loop, e.g., between amino acids 430 and 433 of HPV16 L1, or attached to the DE loop, e.g., between amino acids 133/134 of bovine PV (BPV), or the equivalent amino acids 136/137 of a PV, including without limitation a HPV.

In an embodiment of the invention either the target peptide or the VLP does not comprises a polyionic:cysteine, polycationic:cysteine or polyanionic:cysteine, sequence for docking the target peptide to the VLP to form a chimeric VLP. In an embodiment of the invention neither the target peptide or the VLP comprises a polyionic:cysteine, polycationic:cysteine or polyanionic:cysteine, sequence for docking the target peptide to the VLP to form a chimeric VLP of this invention.

Target peptides might be conjugated to a VLPs via disulfide bonding, see Pejawar-Gaddy et al. *Cancer Immunol Immunother* (2010) 59(11):1685-1696 incorporated herein in its entirety by reference.

In an aspect of the invention the target peptide is inserted recombinantly into a loop of the PV L1 protein, e.g., a BC, CD, DE, EF, FG, or HI loop of the PV L1 protein. In an aspect of the invention the target peptide is inserted in the DE loop or a helix B4 loop of an HPV L1 protein. In an aspect of the invention the target is inserted into the helix B4 loop between amino acids 430 and 433 of HPV16 L1, or inserted into the DE loop between amino acids 133/134 of bovine PV (BPV), or the equivalent amino acids 136/137 of a HPV.

In an aspect of the invention a charged peptide, e.g., 9 glutamic acids or 9 arginine amino acids is inserted recombinantly into a loop of the PV L1 protein. A target peptide is then conjugated to the charged peptides in the loop. The loop may be, e.g., a BC, CD, DE, EF, FG, or HI loop of the PV L1 protein. In an aspect of the invention the target peptide is conjugated to a charged peptide in the DE loop or a helix B4 loop of an HPV L1 protein. In an aspect of the invention the target peptide is conjugated to a charged peptide that is inserted into the helix B4 loop between amino acids 430 and 433 of HPV16 L1, or into the DE loop between amino acids 133/134 of bovine PV (BPV), or the equivalent amino acids 136/137 of a HPV.

In an aspect of the invention VLPs are assembled first from a papillomavirus L1 protein, or L1 and L2 proteins, and a target peptide comprising a CD8+ T cell epitope derived from a human pathogen is then attached to the VLP to generate a chimeric VLP with a surface displayed target peptide. In an aspect of the invention the target peptide is attached to the L1 or L2 protein and then the VLP is assembled such that the target peptide is surface displayed. The target peptide may be attached to either the L1 protein or the L2 protein of the VLP or to both the L1 and L2 proteins of the VLP. The attachment of the target peptide to the VLP may be by conjugating the target peptide to the VLP via a disulfide, a maleimide or an amide linkage.

The chimeric VLP may also be generated recombinantly and assembled from a papilloma virus L1 protein or L1 and L2 proteins wherein the L1 protein or L2 protein has inserted therein a target peptide such that the target peptide is surface displayed on the assembled VLP.

In an embodiment of the invention the target peptide is attached to a VLP by a linker. In an embodiment of the invention the target peptide comprises, consists essentially of, or consists of, a CD8+ T cell epitope and a linker. In an aspect of the invention the linker comprises an amino acid sequence(s) that is recognized and cleaved by one or more enzymes expressed by a tumor cell or present in the tumor microenvironment. The cleavage site(s) may be positioned in the target peptide such that cleavage of the site(s) releases a peptide from the target peptide wherein the released peptide comprises, consists essentially of, or consists of the CD8+ T cell epitope. The released peptide is capable of binding with an MHC such that the complex is recognized by and activates the preexisting CTL specific for the CD8+ T cell epitope of the released peptide. The enzyme may be, e.g., furin, a matrix metalloproteinases (MMPs) e.g., MMP, 1, 2, 3, 7, 8, 9, 11, 13, 14, or 19, an ADAM (a disintegrin and metalloproteinase), e.g., ADAMS 8, 9, 10, 15, 17 or 28, a Cathepsin, e.g., Cathepsin B, D, D, G, or H, N. Elastase, Proteinase-3, Azurocidin, or ADAMTS-1, or an enzyme in the proteasome of a human tumor cell. The enzyme cleavage site may be for example, RX-K/R-R (SEQ ID NO: 209) where X can be any amino acid, e.g., RVKR (SEQ ID NO: 210) or an MMP-cleavable peptide substrate, e.g., Glu-Pro-Cit-Gly-Hof-Tyr-Leu (SEQ ID NO:211), or Gly-Pro-Leu-Gly-Ile-Ala-Gly-Gln **(SEQ ID NO: 212) or Pro-Val-Gly-Leu-Ile-Gly (SEQ ID NO: 213). In an aspect of the invention the cleavage site is not a furin cleavage site or a matrix metalloproteinases (MMPs) cleavage site. In an aspect of the invention the cleavage site is not a cleavage site for one or more of MMP, 1, 2, 3, 7, 8, 9, 11, 13, 14, or 19, an ADAM (a disintegrin and metalloproteinase), e.g., ADAMS 8, 9, 10, 15, 17 or 28, a Cathepsin, e.g., Cathepsin B, D, D, G, or H, N. Elastase, Proteinase-3, Azurocidin, or ADAMTS-1). In an aspect of the invention the target peptide does not comprise an enzyme cleavage site.

In an aspect of the invention the target peptide comprises a CD8+ T cell epitope of one or more human pathogens, e.g., a parasite, a bacterium, or a virus.

The target peptide derived from such pathogen is preferably one that comprises a CD8+ T cell epitope that binds to a Major Histocompatibility Complex (MHC) class I molecule. The MHC class I molecule may be, e.g., an MHC class I of a HLA-A, B or C family. The MHC class I molecule may be, e.g., an MHC class I molecule recited in Table 1 or Table 2. The MHC class I molecule may be, e.g., HLA-A*02:01, HLA-A*03:01/HLA-A*11:01, HLA-A*0201, HLA-A*020101, HLA-A*0203, HLA-A*0206, HLA-A2, HLA-A2.1, or HLA-A*02.

In an aspect of the invention the pathogen is a virus including without limitation, a vaccinia virus, varicella zoster virus, adenovirus, an arbovirus, Epstein-barr virus, a coronavirus, a cytomegalovirus, a Coxsakie virus, a Herpes zoster virus, herpes simplex virus type 1 or type 2, a JC virus, a rubella virus, a hepatitis virus, e.g., hepatitis A virus or hepatitis B virus or hepatitis C virus, an influenza virus, type A or type B, a measles virus, a mumps virus, a parainfluenza virus, a poliovirus, a variola (smallpox) virus, a rabies virus, a respiratory syncytial virus, a rhinovirus, a rotavirus, dengue virus, ebola virus, west nile virus, a yellow fever virus, or a zika virus. The CD8+ T cell epitope may be from a polio virus, a measles virus, an Epstein Barr virus, an influenza virus, a cytomegalovirus (CMV), or a hepatitis virus.

In an aspect of the invention the pathogen is a bacterium. Non-limiting examples of such bacterium include, a bordatella *pertussis, Chlamydia trachomatis, Clostridium tetani*, diphtheria, *hemophilus influenza*, meningococcus, pneumococcus, *Vibrio cholera, Mycobacterium tuberculosis*, BCG, typhoid, *E. coli*, salmonella, *Legionella pneumophila*, rickettsias, *Treponema pallidum pallidum*, streptococcus group A or group B, *Streptococcus pneumonia, Bacillus anthracis, Clostridium botulinum, Yersinia* sp, e.g., *Yersinia pestis*.

In an aspect of the invention the pathogen is a parasite. Non-limiting examples of such parasites include enamoeba *histolytica, Toxoplasma gondii*, a *trichinella* sp., e.g., *Trichinella spiralis*, a *trichomonas* sp., e.g., *Trichomonas vaginalis*, a *trypanosoma* sp., e.g., *Trypanosoma brucei gambiense, Trypanosoma brucei rhodesiense, Trypanosoma cruzi*.

The invention is also directed to methods of using the chimeric VLPs and compositions of this invention to inhibit tumor growth, proliferation, and metastasis.

In an embodiment of this invention, the chimeric VLPs of this invention as described herein find use in the detection of antigen presenting cells having MHC molecules capable of binding and displaying the target peptide's CD8+ T cell epitope, and in the detection of CD8+ T cells that recognize the CD8+ T cell epitope of the target peptide. For example, splenocytes from an animal with a pre-existing immune response can be co-cultured with chimeric VLPs of this invention and the co-cultured cells assessed for the re-activation of T cells utilizing, e.g., immunofluorescence staining and interferon-gamma CD8+ T-cell activation assays known in the art. Naked VLPs, i.e., VLPs without a target peptide may be used as negative controls.

An aspect of the invention described herein is a method for inhibiting the growth and/or progression and/or metastasis of tumor by taking advantage of the pre-existing immunity conferred by prior infections and/or vaccinations against various pathogens. The methods described herein capitalize on the fact that large populations of people are exposed to or immunized against various pathogens. Further, with respect to the latter records of their immunization and vaccinations are accessible. For example large populations of people during childhood are actively vaccinated against a variety of pathogens with vaccines well known in the art. In the methods described herein one of skill in the art can readily ascertain the vaccination/immunization history or infection history of a subject having a tumor and then administer an appropriate chimeric VLP, which displays a target peptide comprising a T cell epitope related to the vaccine to elicit the subject's existing CD8+ memory T cells.

The inventive method is advantageous over pre-existing methods because it does not require identifying a specific tumor associated antigen in order to target T cells to a specific tumor. Thus, the methods described herein can be applied to all tumors in a subject who was previously vaccinated against or infected with a pathogen to inhibit their growth, progression, and metastasis regardless of the tumor associated antigen the tumor cells express.

In an aspect of the invention, to determine which chimeric VLP(s) to administer to the subject, one ascertains if the subject has been actively immunized with a vaccine against a given pathogen, e.g., a virus, e.g., influenza a, hepatitis, measles or polio, a bacteria, e.g., meningococcus, a fungus, e.g. *Candida albicans* or a parasite. A chimeric VLP that comprises a target peptide that contains a CD8+ T cell epitope from the pathogen against which the subject has been immunized is then administered. In an aspect of the invention, to determine which VLP(s) to administer to the subject, one ascertains if the subject has been naturally infected with a given pathogen, e.g., a virus, e.g., influenza a, hepatitis, measles or polio, a bacteria, e.g., meningococcus, a fungus, e.g. *Candida albicans*, or a parasite. A chimeric VLP that comprises a target peptide that contains a CD8+ T cell epitope from such a pathogen is then administered to the subject. The CD8+ T cell epitope is one that binds a MHC class I molecule. Non-limiting examples of CD8+ T cell epitope that bind to particular MHC class I molecules are set forth in Table 1 and Table 2 (see Rickinson and Moss, Ann. Rev. Immunology (1997) 15:405-431, incorporated herein by reference). The method described herein may also comprise determining which MHC class I determinant(s) the subject expresses and then administering a chimeric VLP comprising the target peptide with the CD8+ T cell epitope known to form a complex with that MHC class I determinant(s).

An embodiment of the invention is a method for inhibiting or preventing the growth, progression and/or metastasis of a tumor or proliferation of cancer cells in a subject in need thereof comprising the steps of determining the tissue source of the tumor, determining if the subject has been vaccinated against or infected with a pathogen having a tropism for the tissue source, and administering to the subject a chimeric VLP that comprises a CD8+ T cell epitope of the pathogen or the antigenic component of the vaccine. In an aspect of the invention the chimeric VLPs are administered to the subject in an amount that is sufficient to stimulate CD8+ T cells that recognize the CD8+ epitope in complex with an MHC class I molecule and redirect their cytotoxic activity to the tumor. In an aspect of this invention the chimeric VLPs are administered in an amount sufficient to inhibit the growth, progression and/or metastasis of a tumor. The chimeric VLPs may also be administered to the subject in an amount that is sufficient to inhibit the proliferation of cancer cells and/or induce apoptosis of the cancer cells.

An embodiment of the invention is a method for inhibiting or preventing the growth, progression and/or metastasis of a tumor or proliferation of cancer cells in a subject in need thereof comprising determining if the subject has been actively vaccinated against or infected with a pathogen having a tropism for the tissue having a tumor mass, and administering to the subject a chimeric VLP that comprises a CD8+ T cell epitope of the pathogen or the antigenic component of that vaccine against which the subject has been immunized. In an aspect of the invention the chimeric VLPs are administered to the subject in an amount that is sufficient to stimulate CD8+ T cells, e.g., tissue resident memory T-cells in the tissue having the tumor mass, that recognize the CD8+ epitope in complex with an MHC class I molecule and redirect their cytotoxic activity to the tumor. In an embodiment of the invention the tumor mass and the tissue where the tumor resides are different tissue types, e.g., a hepatic tumor metastasis in lung tissue or a lung tumor metastasis in brain tissue.

An embodiment of the invention is a method for inhibiting or preventing the growth, progression and/or metastasis of a tumor or proliferation of cancer cells comprising the steps of determining if a subject having a tumor had been previously vaccinated against a pathogen, e.g., parasite, a bacterium or a virus, e.g., one or more of a measles virus, an influenza virus, a hepatitis virus, or a polio virus and then administering to such patient an effective amount of the chimeric VLP(s) comprising a surface-displayed target peptide derived from the pathogens for which the subject had been vaccinated. The target peptide comprises a CD8+ T cell epitope of the antigenic component contained in the vaccine. An embodiment of the methods of this invention includes the step of determining if a subject having a tumor had been previously infected with a pathogen, e.g., parasite, a bacterium or a virus, e.g., one or more of a measles virus, an influenza virus, a hepatitis virus, or a polio virus and then administering to such patient an effective amount of the chimeric VLP(s) comprising a surface-displayed peptide comprising a CD8+ T cell epitope derived from such pathogens. The chimeric VLPs are administered to the subject in an amount that is sufficient to inhibit the growth, progression and/or metastasis of a tumor. The chimeric VLPs may also be administered to the subject in an amount that is sufficient to inhibit the proliferation of cancer cells and/or induce apoptosis of the cancer cells. This method may further comprise determining whether or not the subject who has been vaccinated against a preselected pathogen has memory T cells against the pathogen, i.e., pre-existing CTLs that recognize a CD8+ T cell epitope of the pathogen. If the subject does not have such CTLs, the method further comprises a further "boosting" step that comprises re-vaccinating the subject against the pathogen. After the subject has been re-vaccinated, the chimeric VLP comprising a CD8+ T cell epitope of the pathogen is administered in an amount sufficient to bind the tumor thereby redirecting the CD8+ T cell-specific CTLs to the tumor with bound chimeric VPL. Methods for assaying a subject for activated CTLs specific for a given CD8+ T cell epitope are well known in the art.

Also an embodiment of the invention is a method for inhibiting or preventing the growth, progression and/or metastasis of a tumor, or proliferation of cancer cells, in a naïve subject, i.e., a subject who does not have preexisting CTLs specific to an epitope of a preselected pathogen. A naive subject includes, e.g., a subject who had not been previously actively vaccinated against, or naturally immunized/exposed to, the pathogen. The subjects cells may also be assayed for the presence of CTLs specific to epitopes of a preselected pathogen. Whether a subject has been vaccinated or exposed to a pathogen can be determined, e.g., by reviewing the subject's vaccination records or asking the subject whether he has been vaccinated or exposed to or contracted a particular disease. The method comprises actively vaccinating a naïve subject in need thereof with a vaccine against a preselected pathogen. After vaccinating the subject, a chimeric VLP of this invention displaying the CD8+ T cell epitope of the pathogen is administered to the subject in a sufficient amount for the chimeric VLP to bind to the tumor, thereby redirect the CD8+ T cell epitope-specific CTLs to the tumor cells with bound chimeric VLP. By redirecting the CTLs to the chimeric VLP-bound tumor cells, the growth, progression and/or metastasis of the tumor, or proliferation of cancer cells is inhibited or prevented. In an embodiment, the chimeric VLP is administered to the subject 1 week, 2 weeks or more after the subject is vaccinated to allow for activation of the CTLs prior to administration of the chimeric VLP. In an embodiment of the invention, the naïve subject is vaccinated against the preselected pathogen and then the subject is monitored for the presence of activated CTL cells specific for a CD8+ T cell epitope of the vaccine. After such activated CTLs are detected, the chimeric VLP comprising the CD8+ T cell epitope is administered to the subject. The chimeric VLP is administered in an amount sufficient to bind the tumor and redirect the CTLs specific for the CD8+ T cell epitope of the chimeric VLP to the bound tumors. The redirected CTLs then inhibit or prevent the growth, progression and/or metastasis of the tumor, or proliferation of cancer cells. The vaccine may be against any pathogen as described herein, e.g., measles, mumps, chicken pox or hepatitis B.

It has been reported that HPV capsids (VLP and psuedovirions (PsV)) have tumor tropism and directly bind and infect tumor cells, including, e.g., ovarian and lung cancer cells. See Kines et al. *International Journal of Cancer* (15 Feb. 2016) 138(4): 901-911 incorporated herein by reference. Kines reports that such binding may be heparan sulfate proteoglycan (HSPG) dependent. Without wishing to be bound by theory, it is contemplated that the chimeric VLPs described herein preferentially bind to tumor cells, e.g., they bind more to tumor cells than to non-tumor cells, and the presence of chimeric VLPs may result in a positive pro-inflammatory tumor microenvironment that attracts infiltrating CD8+ T-cells. At the same time, the VLPs may stimulate a response by adaptive memory T-cells that resulted from a previous vaccination or infection and that recognize the target peptide's CD8+ T cell epitope. It is contemplated that these strong responses are able to bypass immune tolerance, and render the tumor cells susceptible to this preexisting immunity thereby inhibiting the growth, progression and metastasis of the tumor.

The chimeric VLPs described herein or composition comprising the chimeric VLPs may be administered to a subject in need thereof intravenously, intramuscularly, subcutaneously, intraperitoneally, intranasally, intraocularly, intradermally, intratumorally, transmucosally, or as an aerosol.

In another embodiment of this invention the chimeric VLPs of this invention are administered to the subject having a tumor in conjunction with another anti-cancer therapy, e.g., radiotherapy, chemotherapy, immunotherapy or surgery. For example, the chimeric VLPs are administered to the subject having a tumor in conjunction with a checkpoint inhibitor. Checkpoint inhibitors known in the art and useful in the invention include without limitation, ipilimumab (Yervoy®), pembrolizumab (Keytruda®), and nivolumab (Opdivo®), Atezolizumab (Tecentriq), Avelumab (Bavencio), Durvalumab (Imfinzi). Administration and dosage schedules for checkpoint inhibitors are set forth in the prescribing information for each checkpoint inhibitor, incorporated herein by reference.

Chemotherapeutic agents are well known in the art and include, without limitation, aflibercept, asparaginase, bleomycin, busulfan, carmustine, chlorambucil, cladribine, cyclophosphamide, cytarabine, dacarbazine, daunorubicin, doxorubicin, etoposide, fludarabine, gemcitabine, hydroxyurea, idarubicin, ifosfamide, irinotecan, lomustine, mechlorethamine, melphalan, mercaptopurine, methotrexate, mitomycin, mitoxantrone, pentostatin, procarbazine, topotecan, vinblastine, vincristine, retinoic acid, oxaliplatin, carboplatin, 5-fluorouracil, teniposide, amasacrine, docetaxel, paclitaxel, vinorelbine, bortezomib, clofarabine, capecitabine, actinomycin D, epirubicin, vindesine, methotrexate, 6-thioguanine, tipifarnib, imatinib, erlotinib, sorafenib, sunitinib, dasatinib, nilotinib, lapatinib, gefitinib, temsirolimus, everolimus, rapamycin, bosutinib, pzopanib, axitinib, neratinib, vatalanib, pazopanib, midostaurin, enzastaurin, trastuzumab, cetuximab, panitumumab, rituximab, bevacizumab, mapatumumab, conatumumab, and lexatumumab. Methods for using such agents are also well known in the art.

Also an embodiment of this invention is a pharmaceutically acceptable composition comprising the chimeric VLPs of this invention, and one or more carriers or excipients. The composition may comprise, e.g., a single type of chimeric VLP or a plurality of chimeric VLPs such that at least two of the chimeric VLPs do not comprise the same target peptide.

Another aspect of the invention is a kit comprising the chimeric VLPs of the invention. The kit may comprise instructions for determining a subject's vaccination/immunization history and/or infection history and for administering an appropriate chimeric VLP in the kit to the subject. An appropriate chimeric VLP comprises a target peptide comprising a CD8+ T cell epitope of a pathogen for which the subject has been actively immunized or of a pathogen that had previously infected the subject. The instructions might also include instructions for determining the MHC class I molecule complement expressed by the subject, or expected be expressed by the subject based on their racial ancestry, and administering an appropriate chimeric VLP in the kit to the subject wherein the appropriate chimeric VLP comprises a CD8+ T cell epitope of the pathogen that binds to an MHC class I molecule expressed or expected to be expressed by the subject.

DETAILED DESCRIPTION OF THE INVENTION

Figure 1:
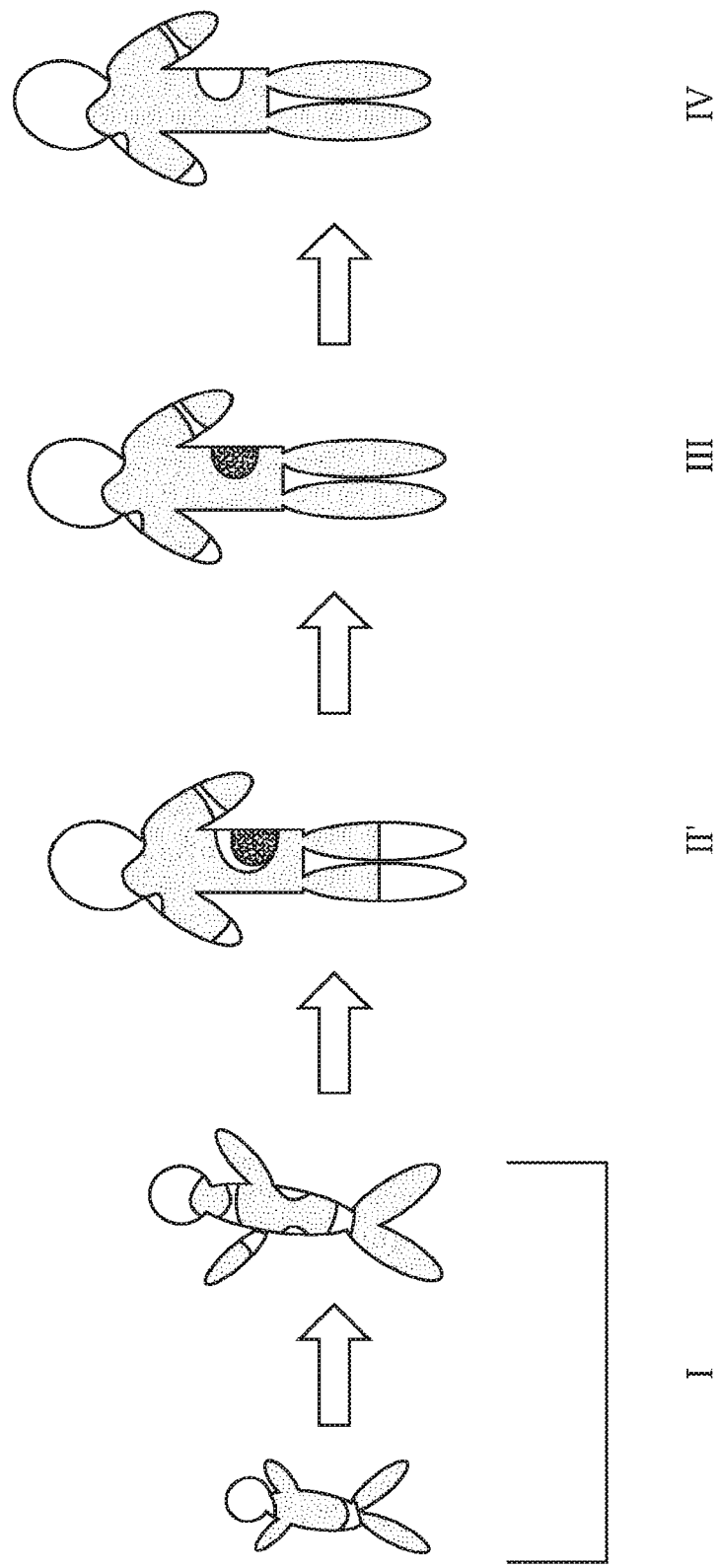
FIG. 1 depicts an embodiment of a method of the invention described herein. The chimeric VLPs with a target peptide comprising an immunogenic CD8+ T cell epitope recognized by preexisting immunity (e.g. MMR, chicken pox, polio) selectively bind to tumor cells such that immune tolerance is bypassed and preexisting immunity is used to control tumors that bind the chimeric VLPs: Subject as a child receives multiple approved vaccines, which produce strong immunity both T-cell and antibody responses (white dots) (I); As an adult the subject unfortunately develops cancer, the subject's vaccination history is assessed and the subject is administered a chimeric VLP(s) of this invention comprising a CD8+ T cell epitope of the pathogen against which the subject was vaccinated (III). The stimulated existing CD8+ T cells, the recall immune response, are redirected to attack the tumors that have bound the chimeric VLP (III) resulting in inhibition of growth, progression and/or metastasis of the cancer (IV). In one embodiment, CTL epitope can further be from a virus with natural tissue tropism to the organ of interest where the tumor resides.

Papillomaviruses are small, double-stranded, circular DNA tumor viruses. The papillomavirus virion shells contain the L1 major capsid protein and the L2 minor capsid protein. Expression of L1 protein alone or in combination with L2 protein in eukaryotic or prokaryotic expression systems is known to result in the assembly of capsomeres and VLPs. As used herein, the term "capsomere" is intended to mean a pentameric assembly of papillomavirus L1 polypeptides (including full-length L1 protein and fragments thereof). Native L1 capsid proteins self-assemble via intermolecular disulfide bonds to form pentamers (capsomeres).

The papillomavirus virion contains 72 pentamers (capsomeres) of L1 protein. Trus et al., 4 *Nat. Struct. Biol.* 413-20 (1997). The L1 protein is capable of self-assembly into capsid-like structures that are morphologically indistinguishable from native virions when expressed in eukaryotic cells. See Buck et al., 82 *J. Virol.* 5190-97 (2008) and Roy et al., 4 *Hum. Vaccin.* 5-12 (2008), both incorporated herein by reference. The L1 monomer contains 12 β-strands, 6 loops (BC, CD, DE, EF, FG, HI), and 5 helices (H1-H5). Most of the loops are highly exposed towards the outer surface of the capsid, attachment of a target peptide to one of these loops, by e.g., disulfide linkage, maleimide linkage, by "click" chemistry or by binding to a polyionic docking site, as described herein, in these areas will result in the target peptide being displayed on the outer surface of VLPs.

An embodiment of this invention is a chimeric VLP, comprising a papilloma virus (PV) L1 protein, or an PV L1 and PV L2 protein, and a surface-displayed target peptide. The the target peptide comprises, consists essentially of, or consists of, a CD8+ T cell epitope of a human pathogen, wherein the CD8+ T cell epitope is not a tumor associated antigen. In an aspect of this invention the target peptide is conjugated to a reduced sulfhydryl group of a cysteine of the VLP and optionally, the cysteine is not part of a polyionic: cysteine, polycationic:cysteine or polyanionic:cysteine, sequence. The VLP may comprise both papilloma L1 and L2 proteins. The target peptides may be conjugated to a reduced sulfhydryl group(s) of the L1 protein and/or the L2 protein via a disulfide linkage or a maleimide linkage. In an aspect of this invention the target peptide is conjugated to lysine and/or an arginine of the VLP via an amide linkage.

As used herein, the term "virus-like particle" or "VLP" refers to a particle comprised of a higher order assembly of capsomeres. VLPs are non-infectious and non-replicating, yet morphologically similar to native papillomavirus virion. One example of such a higher order assembly is a particle that has the visual appearance of a whole (72 capsomere) or substantially whole, empty papillomavirus capsid, which is about 50 to about 60 nm in diameter and has a T=7 icosahedral construction. Another example of such a higher order assembly is a particle of about 30 to about 35 nm in diameter, which is smaller than the size of a native papillomavirus virion and has a T=1 construction (containing 12 capsomeres). For purposes of the present invention, other higher order assemblies of capsomeres are also intended to be encompassed by the term VLP. In certain embodiments, the VLPs can replicate conformational epitopes of the native papillomavirus from which the L1 protein or polypeptide or L2 protein or polypeptide is derived. Methods for assembly and formation of human papillomavirus VLPs and capsomeres of the present invention are well known in the art. See, e.g., U.S. Pat. Nos. 6,165,471, 6,153,201, and 9,149,503, as well as WO 94/020137, all of which are incorporated herein in their entirety by reference.

The present invention relates to chimeric papillomavirus VLPs, compositions comprising the chimeric VLPs, methods for making the chimeric VLPs, and use of the chimeric VLPs in the treatment of tumors. A chimeric papillomavirus VLPs of this invention comprises a target peptide. In some embodiments the target peptide comprises a CD8+ T cell epitope, consists essentially of a CD8+ epitope, or consists of a CD8+ T cell epitope. In some embodiments the target peptide comprises, consists essentially of, or consists of, a CD8+ T cell epitope and a linker for attaching the target peptide to the VLP. The linker may comprise an enzyme cleavage site for releasing the CD8+ T cell epitope from the VLP. In an aspect of the invention the CD8+ T cell epitope is of a human pathogen, e.g., a parasite, a fungus, a bacteria or a virus. Non-limiting examples of a virus includes, a vaccinia virus, varicella zoster virus, a Herpes zoster virus, rubella, a hepatitis virus, e.g., hepatitis A virus or hepatitis B virus or hepatitis C virus, influenza, e.g., type A or type B, a measles virus, a mumps virus, a poliovirus, a variola (smallpox) virus, a rabies virus, dengue virus, ebola virus, west nile virus, a yellow fever virus, or a zika virus.

Non-limiting examples of a bacterium include, a bordatella *pertussis*, *Chlamydia trachomatis*, *Clostridium tetani*, diphtheria, *Hemophilus influenza*, meningococcus, pneumococcus, *Vibrio cholera*, *Mycobacterium tuberculosis*, BCG, typhoid, *E. coli*, *salmonella*, *Legionella pneumophila*, rickettsias, *Treponema pallidum pallidum*, streptococcus group A or group B, *Streptococcus pneumonia*, *Bacillus anthracis*, *Clostridium botulinum*, *Yersinia* sp, e.g., *Yersinia pestis*.

Non-limiting examples of a parasite include enamoeba *histolytica*, *Toxoplasma gondii*, a *trichinella* sp., e.g., *Trichinella spiralis*, a *trichomonas* sp., e.g., *Trichomonas vaginalis*, a *trypanosoma* sp., e.g., *Trypanosoma brucei gambiense*, *Trypanosoma brucei hodesiense*, *Trypanosoma cruzi*, or a *plasmodium*, e.g., *Plasmodium falciparum*, *Plasmodium vivax*, or *Plasmodium malariae*.

In an aspect of the invention the CD8+ T cell epitope is of a polio virus, a measles virus, a Epstein Barr virus, an influenza A virus or a cytomegalovirus (CMV) or a hepatitis B virus. In an aspect of the invention the CD8+ T cell epitope is a T cell epitope set forth in Table 1. In an aspect of the invention the CD8+ T cell epitope is:

KLWESPQEI, (SEQ ID NO: 6)

YVVYDHSGEAVK, (SEQ ID NO: 15)

FLPSDFFPSV, (SEQ ID NO: 69)

FLLTRILTI, (SEQ ID NO: 70)

WLSLLVPFV, (SEQ ID NO: 71)

GLSRYVARL, (SEQ ID NO: 72)

FLLSLGIHL, (SEQ ID NO: 73)

(K)GILGFVFTL(T)(V), (SEQ ID NO: 217)

-continued

KLSTRGVQIASNEN, (SEQ ID NO: 125)

RGLQRRRFVQNALNGNG, (SEQ ID NO: 131)

FMYSDFHFI, (SEQ ID NO: 136)

NLVPMVATV, (SEQ ID NO: 151)

VAIIEVDNEQPTTRAQKL, (SEQ ID NO: 152)

TRAQKLFAMWRITYKDTV, (SEQ ID NO: 153)

Any 9-mer sequence of
GACVAIIEVDNEQPTTRAQKLFAMWRITYKDTVQLRRKL, (SEQ ID NO: 154)

SVRDRLARL, (SEQ ID NO: 167)

LLDRVRFMGV, (SEQ ID NO: 217)

CLGGLLTMV, (SEQ ID NO: 196)
or

GLCTLVAML. (SEQ ID NO: 143)

SLPRSRTPI (SEQ ID NO: 218)
or

SAPLPSNRV. (SEQ ID NO: 219)

In an aspect of the invention the CD8+ T cell epitope of the target peptide binds to an MHC class I molecule. The MHC class I molecule may be from HLA-A, B, C families. The MHC class I molecule may be an MHC class I molecule recited in Table 1 or Table 2. The MHC class I molecule may be, e.g., HLA-A*02:01, HLA-A*03:01, HLA-A*11:01, HLA-A*0201, HLA-A*020101, HLA-A*0203, HLA-A*0206, HLA-A2, HLA-A2.1, or HLA-A*02.

In an aspect of the invention the target peptide is about 8 amino acid to about 50 amino acids in length, or about 8 amino acid to about 45 amino acids in length, or about 8 amino acid to about 40 amino acids in length, about 8 amino acid to about 35 amino acids in length, or about 8 amino acid to about 30 amino acids in length, about 8 amino acid to about 25 amino acids in length, about 8 amino acid to about 20 amino acids in length, is about 8 amino acid to about 15 amino acids in length. In an aspect of the invention the target peptide is about 13 amino acid to about 50 amino acids in length, or about 13 amino acid to about 45 amino acids in length, or about 13 amino acid to about 40 amino acids in length, about 13 amino acid to about 35 amino acids in length, or about 13 amino acid to about 30 amino acids in length, about 13 amino acid to about 25 amino acids in length, about 13 amino acid to about 20 amino acids in length, is about 13 amino acid to about 15 amino acids in length. In an aspect of the invention the CD8+ T cell epitope may be, e.g., 8, 9, 10, 11, 12, 13, 14, 15, 16 or 17 amino acids in length.

In an embodiment of the invention, the chimeric papillomavirus VLP comprises an L1 polypeptide and a target peptide. In other embodiments, the chimeric VLP can comprise an L1 polypeptide and an L2 polypeptide and a target peptide. The L1 polypeptide can be full-length L1 protein or an L1 polypeptide fragment. In specific embodiments, the full-length L1 protein or L1 polypeptide fragment is VLP assembly-competent; that is, the L1 polypeptide will self-assemble to form capsomeres that are competent for self-assembly into a higher order assemblies, thereby forming a VLP. In more specific embodiments, the VLPs comprise a fully assembled papillomavirus capsid, a structure of about 50 nm and composed of 72 capsomeres or 360 copies of L1 protein.

The L1 sequences are known for substantially all papillomavirus genotypes identified to date, and any of these L1 sequences or fragments can be employed in the present invention. Examples of L1 polypeptides include, without limitation, full-length L1 polypeptides (e.g., HPV16 L1 polypeptide, SEQ ID NO: 205), L1 truncations that lack the native C-terminus, L1 truncations that lack the native N-terminus, and L1 truncations that lack an internal domain. See Conway et al., 88(4) J. Dental Res. 307-17 (2009); Chen et al., 5 Mol. Cell. 557-67 (2000); and Paintsil et al., 223(1) Virology 238-44 (1996) all incorporated herein in their entirety by reference. The L1 protein may be for example a modified L1 protein, e.g., a modified HPV16 L1 protein wherein the HPV16 L2 amino acids 17-36 (RG1 epitope) are inserted within the DE-surface loop of HPV16 L1 (Schellenbacher et al. 2013 J. Invest Dermatol; 133(12):2706-2713; Slupetzky et al., 2007 Vaccine 25:2001-10; Kondo et al. 2008 J. Med. Virol 80; 841-6; Schellenbacher et al. 2009 J. Virol 83:10085-95; Caldeira et al. 2010 Vaccine 28:4384-93.)

The L2 polypeptide can be full-length L2 protein or an L2 polypeptide fragment. The L2 sequences are known for substantially all papillomavirus genotypes identified to date, and any of these L2 sequences or fragments can be employed in the present invention. Examples of L2 polypeptides include, without limitation, full-length L2 polypeptides (e.g., HPV16 L2 polypeptide, SEQ ID NO: 207), L2 truncations that lack the native C-terminus, L2 truncations that lack the native N-terminus, and L2 truncations that lack an internal domain.

The papillomavirus VLPs can be formed using the L1 and optionally L2 polypeptides from any animal papillomavirus, or derivatives or fragments thereof. Thus, any known (or hereafter identified) L1 and optional L2 sequences of human, bovine, equine, ovine, porcine, deer, canine, feline, rodent, rabbit, etc., papillomaviruses can be employed to prepare the VLPs or capsomeres of the present invention. See de Villiers et al., Virology 324: 17-27 (2004) for a near complete listing of papillomavirus genotypes and their relatedness, incorporated herein by reference.

In certain embodiments, the L1 and optionally L2 polypeptides that are used to form the VLPs are from a non-human papillomavirus or a human papillomavirus genotype other than HPV-6, HPV-11, HPV-16, and HPV-18. For example the L1 and/or L2 proteins may be from HPV 1, 2, 3, 4, 5, 6, 8, 9, 15, 17, 23, 27, 31, 33, 35, 38, 39, 45, 51, 52, 58, 66, 68, 70, 76, or 92.

In particular embodiments, a chimeric VLP (whether it comprises an L1 polypeptide or L1 and L2 polypeptides) comprises a region of negatively charged amino acids on a surface exposed area that is capable of binding to a target peptide comprising a region of positively charged amino acids. In further embodiments, the region of negatively charged amino acids may be flanked, on one or both sides, by one or more cysteine residues (referred to as polyanionic: cysteine or more specifically, polyglutamic acid:cysteine or polyaspartic acid:cysteine). In such cases, the conjugation of the VLP and target peptide would result from non-covalent binding between the complementary amino acid charges of the VLP and target peptide and a disulfide bond between the cysteines. In other embodiments, the cysteine(s) are one or more amino acids away from the region of charged amino acids such that any secondary/tertiary structure would bring the charged amino acid region in close proximity to the cysteine(s). See, e.g., U.S. Publication No. 2014/0050753 published Feb. 20, 2014 incorporated herein in their entirety by reference. In an embodiment of the invention the target peptide comprises of a CD8+ T cell epitope, e.g., the CD8+ T cell epitopes of Table 1 or Table 2, and a polyionic: cysteine for attaching the target peptide to a VLP comprising a complementary polyionic:cysteine sequence. In an embodiment of the invention the target peptide comprises, consists essentially of, or consists of a CD8+ T cell epitope and a polyionic:cysteine for attaching the target peptide to a VLP comprising a complementary polyionic:cysteine sequence and an enzyme cleavage site positioned between the terminal cysteine and the CD8+ T cell epitope. In an embodiment of the invention the target peptide comprises, consists essentially of, or consists of a terminal cysteine, a CD8+ T cell epitope, e.g., the CD8+ T cell epitopes of Table 1 or Table 2, and an enzyme cleavage site positioned between the terminal cysteine and the CD8+ T cell epitope.

Negatively charged amino acids that can be used in producing the chimeric VLP include, e.g., glutamic acid and aspartic acid. These amino acids can be used singly (e.g., polyglutamic acid) or in combination. In a specific embodiment, the region comprises glutamic acid. The number of negatively charged amino acids can vary, and can include about 4 to about 20 amino acids, about 6 to about 18 amino acids, about 8 to about 16 amino acids, and the like. In a specific embodiment, the region comprises about 8 negatively charged amino acids. In a more specific embodiment, the region comprises EEEEEEEEC (E8C) (SEQ ID NO: 214). In another embodiment, the region comprises CEEEEEEEEC (SEQ ID NO: 215). For a method for conjugating target peptides to a VLPs via disulfide bonding, see, e.g., Pejawar-Gaddy et al. *Cancer Immunol Immunother* (2010) 59(11):1685-1696 incorporated herein in its entirety by reference. Briefly the presence of a polyarginine-cysteine moiety on the target peptide allows docking of the peptide to the polyanionic site (EEEEEEEEC, E8C (SEQ ID NO: 214)) present in the various loops of the L1 particles. Covalent cross-linking between the two cysteine residues should render this association irreversible under oxidizing conditions. For the conjugation reactions, purified HPV particles are dialysed in conjugation buffer (20 mM Tris/HCl pH=7.5, 150 mM NaCl, 5% glycerol, 0.5 mM CaCl2) and then the peptide and the oxidizing reagents are added, allowing the reaction to proceed for 16 hrs at 4° C. At the end of the incubation, the reaction mixtures are applied to a size-exclusion column (Sephadex G-100, Pharmacia, volume 20 ml, flow rate 1 ml/min, 10 mM Tris/HCl (pH=7.4), 150 mM NaCl, 0.5 mM $CaCl_2$) to remove unconjugated peptide and exchange buffer. Conjugated particles that elute in the void volume are identified by the presence of the L1 protein on SDS-PAGE. The conjugated particles are analyzed by electron microscopy. One of ordinary skill in the art can, through routine experimentation, create a VLP that includes a polyionic region in a surface exposed area (e.g., one or more loops) and that is VLP assembly competent.

In alternative embodiments, the chimeric papillomavirus VLP is engineered to comprise a region of positively charged amino acids and one or more cysteines (polycationic:cysteine) on a surface exposed area that is capable of binding to a target peptide that comprises a region of negatively charged amino acids and one or more cysteines (polyanionic:cysteine).

In specific embodiments, a chimeric VLP comprises an L1 polypeptide (e.g., full length) where a polyanionic: cysteine amino acid region is inserted into one or more loops of the L1 polypeptide (e.g., HI loop). Such regions can, for example, be inserted into the amino acid sequence encoding a particular loop (with no deletion of corresponding L1 amino acids), inserted and replacement of L1 amino acids in the loop, or even an insertion and partial deletion of L1 amino acids in the particular loop). In specific embodiments, a chimeric VLP comprises an L2 polypeptide (e.g., full length) where a polyanionic:cysteine amino acid region is inserted therein. The insertion may be with no deletion of corresponding L2 amino acids or it may be inserted and amino acids may be deleted from the L2 polypeptide. One of skill in the art using routine experimentation can optimize the chimeric VLP for placement of the polyanionic amino acid sequences to suit particular target peptides.

Alternatively, for attachment of the target peptides to the VLP, the L1 and/or L2 proteins of the VLP may also be modified to comprise at least one first unnatural amino acid (also referred to herein as non-natural amino acid or non-canonical amino acid (nnAA)) at a site of interest and the two or more target peptides may be modified to comprise at least one second unnatural amino acid, wherein the first unnatural amino acid is different from, and reactive with the second unnatural amino acid. See e.g., U.S. Publication No. 2016/0206715 published Jul. 21, 2016 incorporated herein by reference. An example of one first unnatural amino acid is azidohomoalanine. An example of a second unnatural amino acid is propargyloxyphenylalanine. The azide functional group of azidohomoalanine incorporated into a capsid protein of a VLP may participate in a (3+2) cycloaddition click reaction with an alkyne functional group of propargyloxyphenylalanine incorporated into a target peptide, resulting in VLP crosslinked to a target peptide. Other unnatural amino acid-containing capsid proteins within the same VLP may similarly participate in the (3+2) cycloaddition click reaction to produce a VLP with two or more target peptides. In another embodiment, the chimeric VLP may display a target peptide and a CpG. In another embodiment, the chimeric VLP may display a target peptide and a nucleic acid or a modified nucleic acid. In another embodiment, the chimericVLP may display two or more target peptides and a CpG. In a separate embodiment, the chimeric VLP may display two or more target peptides and a nucleic acid or a modified nucleic acid.

In an embodiment of the invention, the VLP contains at least one or at least two unnatural amino acid per capsid monomer subunit. For example, at least one-twentieth of the total number of unnatural amino acids in a VLP may be used to attach a target peptide or nucleic acid to produce the chimeric VLP. In another embodiment, about one fourth of the total number of unnatural amino acids in a VLP may be used to attach a target peptide or nucleic acid. In a further embodiment, about one-third of the total number of unnatural amino acids in a VLP may be used to attach a target peptide or nucleic acid. In yet another embodiment, about one half of the total number of unnatural amino acids in a VLP may be used to attach a target peptide or nucleic acid.

In an aspect of this invention the VLP is assembled from papillomavirus L1 protein or L1 protein and L2 protein, then subjected to reducing conditions sufficient to reduce the sulfhydryl groups of cysteine residues on the surface of VLP while maintaining the capsid-like icosahedron structure of the VLP and the target peptide is conjugated to the sulfhydryl group via a disulfide linkage or a maleimide linkage. In an embodiment of this invention the cysteine is on the surface of the VLP. In an aspect of this invention the VLP is assembled from papillomavirus L1 protein or L1 protein and L2 protein and the target peptide is conjugated to the sulfhydryl group of a cysteine via a disulfide linkage or a maleimide linkage wherein the conjugation reaction is performed under a nitrogen atmosphere. In an embodiment of this invention the cysteine is on the surface of the VLP.

In an aspect of this invention the VLP is assembled from papillomavirus L1 protein, or L1 protein and L2 protein and then subjected to environmental conditions of basic pH while maintaining the capsid-like icosahedron structure of the VLP and the target peptide with a maleimide group at the N-terminus is conjugated to a primary amine on a lysine and/or a guanidyl group on an arginine residue of the VLP via 1-4 addition reaction. In an embodiment of this invention the lysine and/or the arginine are on the surface of the VLP.

In an aspect of this invention the VLP is assembled from papillomavirus L1 protein, or L1 protein and L2 protein, then subjected environmental conditions of a basic pH, while maintaining the capsid-like icosahedron structure of the VLP, and the target peptide with a di-bromo or di-iodo maleimide group at its N-terminus is conjugated to a primary amine group on a lysine residue and/or a guanidyl group on an arginine residue of the VLP via 1-4 addition reaction. In an embodiment of this invention the lysine and/or the arginine are on the surface of the VLP.

In an aspect of this invention the VLP is assembled from papillomavirus L1 protein, or L1 protein and L2 protein, then subjected to environmental conditions of a basic pH, while maintaining the capsid-like icosahedron structure of the VLP, and the target peptide with N-hydroxysuccinimide ester group at the C-terminus is conjugated to a primary amine group on a lysine residue and/or guanidyl group on an arginine residue via amide formation. In an embodiment of this invention the lysine and/or the arginine are on the surface of the VLP.

Rather than attaching the target peptide to the VLP via, e.g., binding of negatively and positively charged amino acids, or via maleimide based conjugation, a nucleic acid sequence encoding the target peptide may be inserted into the nucleic acid encoding the L1 protein and/or L2 protein such that upon expression, a fusion protein is produced wherein the target peptide is inserted into a loop of the L1 polypeptide and/or into the L2 protein and displayed on the surface of the VLP.

Also, in an embodiment of the invention, in the chimeric VLP, at least one-tenth of the viral coat proteins may display a target peptide. In another embodiment, at least one-fifth of the viral coat proteins may display a target peptide. In yet another embodiment, about half of the viral coat proteins may display a target peptide. In a further embodiment, about two-thirds of the viral coat proteins may display a target peptide. In yet another embodiment, nearly all of the viral coat proteins may display a target peptide.

In another embodiment of the invention, the VLP or target peptides may further include one or more agents from the group of: GM-CSF, IL-15, Pam3SK4, poly (I:C), LPS, flagellin, imiquimod, and CpG-X and MPL.

The genetic constructs encoding the L1 protein (e.g., full or partial length L1 polypeptide), and optionally the L2 protein (e.g., full or partial length L2 polypeptide) with or without a sequence encoding the target peptide, can be prepared according to standard recombinant procedures well known to those of ordinary skill in the art. DNA molecules encoding the various polypeptide components are ligated together to form an in-frame gene fusion that results in, for example, a single open reading frame that expresses, e.g., a polyionic papillomavirus capsid polypeptide (L1 or L1/L2), or a papillomavirus capsid polypeptide (L1 or L1/L2) comprising a target peptide. The DNA coding sequences, or open reading frames, encoding the whole or partial L1 and/or L1/L2 polypeptides can be ligated to appropriate regulatory elements that provide for expression (i.e., transcription and translation) of the protein encoded by the DNA molecule. These regulatory sequences, typically promoters, enhancer elements, leader sequences, transcription terminal signals, etc., are well known in the art.

In particular embodiments, the VLPs with or without the target peptide are formed in Sf-9 insect cells upon expression of the L1 protein using recombinant baculovirus. General methods for handling and preparing baculovirus vectors and baculovirus DNA, as well as insect cell culture procedures, are known to those of ordinary skill in the art. See, e.g., Volpers et al., 69 *J. Virol.* 3258-64 (1995); Kirnbauer et al., 67(12) *J. Virol.* 6929-36 (1993); Kool et al., 130 *Arch. Virol.* 1-16 (1993); Rose et al., 67(4) *J. Virol.* 1936-44 (1993); and US Pub. No. 20140050753 each incorporated herein in their entirety by reference.

When a prokaryotic host cell is selected for subsequent transformation, the promoter region used to construct the recombinant DNA molecule should be appropriate for the particular host. As is well known in the art, the DNA sequences of eukaryotic promoters, for expression in eukaryotic host cells, differ from those of prokaryotic promoters. Eukaryotic promoters and accompanying genetic signals may not be recognized in or may not function in a prokaryotic system, and, further, prokaryotic promoters are not recognized and do not function in eukaryotic cells.

Thus, the DNA molecules encoding the polypeptide products to be expressed in accordance with the present invention can be cloned into a suitable expression vector using standard cloning procedures known in the art, including restriction enzyme cleavage and ligation with DNA ligase as described by Sambrook et al., Molecular Cloning: A Laboratory Manual, Second Edition, Cold Spring Harbor Press, NY (2001), and Ausubel et al., Current Protocols in Molecular Biology, John Wiley & Sons, New York, N.Y. (2008), each of which is hereby incorporated by reference in its entirety. Recombinant molecules, including plasmids, can be introduced into cells via transformation, particularly transduction, conjugation, mobilization, or electroporation. Once these recombinant plasmids are introduced into unicellular cultures, including prokaryotic organisms and eukaryotic cells, the cells are grown in tissue culture and vectors can be replicated.

For the recombinant expression of the papillomavirus L1 protein (and optionally an L2 protein), and resulting VLP assembly, the recombinant vectors produced above are used to infect a host cell. Any number of vector-host combinations can be employed, including plant cell vectors (*Agrobacterium*) and plant cells, yeast vectors and yeast hosts, baculovirus vectors and insect host cells, vaccinia virus vectors and mammalian host cells, or plasmid vectors in *E. coli*. Additional mammalian expression vectors include those derived from adenovirus adeno-associated virus, nodavirus, and retroviruses.

In alternative embodiments, recombinant expression vectors and regulatory sequences suitable for expression of papillomavirus VLPs in yeast or mammalian cells are well known and can be used in the present invention. See, e.g., Buonamassa et al., 293(2) *Virology* 335-44 (2002); Sasagawa et al., 2016 *Virology* 126-95 (1995); Hagensee et al., 67(1) *J. Virol.* 315-22 (1993). See also, U.S. Pat. No. 7,112,330 and U.S. Patent Publication No. 2008016637, all of which are incorporated herein by reference.

Regardless of the host-vector system utilized for the recombinant expression and self-assembly of capsomeres and/or VLPs, these products can be isolated from the host cells, and then purified using known techniques. In one embodiment, chimeric papillomavirus VLPs can be purified by centrifugation in CsCl or sucrose gradients. See Sasagawa et al., 2016 Virology 126-95 (1995); Volpers et al., 69 *J. Virol.* 3258-64 (1995); Rose et al., 75 *J. Gen. Virol.* 2445-49 (1994); Kirnbauer et al., 67(12) *J. Virol.* 6929-36 (1993); Rose et al., 67(4) *J. Virol.* 1936-44 (1993). Substantially pure VLP preparations can be conjugated with a target peptide, and then used in the methods of this invention.

In an embodiment of the invention herein, the L1 protein and L2 protein are essentially the wild type versions, except for the attachment or insertion of the target peptide and the changes to the L1 and L2 sequences needed for the attachment. However, a skilled worker will recognize that variants of the L1 and the L2 protein can also be used, provided that the protein can tolerate the insertion or attachment of a suitable target peptide and can assemble into a VLP, or at least a pentamer (capsomer). Several examples of such variants have been described. For example, one can use a truncated L1, lacking up to 10 amino acids from its N-terminus or lacking up to 30 amino acids from its C-terminus. (See, e.g., Chen et al., *J Mol Bio* 2001 Mar. 16; 307(1):173-82, or Bishoop et al. (2007) *Journal of Biological Chemistry* 282, 31803-31811, both of which are incorporated by reference for their disclosure of making and using such truncated L1 proteins). In another embodiment, a small fusion to a peptide of about 60 amino acids can be used. (See, e.g., Virology 1997 Jul. 21; 234(1):93-111, which is incorporated by reference for its disclosure of such fusion peptides.) In another embodiment, hybrid L1 molecules can be used, in which one portion of the molecule from a first strain of PV is swapped into an L1 molecule from a second strain of PV. For example, certain functional portions of the L1 molecule, such as externally exposed "loops" of the protein, can be swapped between molecules from different strains of PV. For examples of such hybrid L1 proteins, see, e.g., Christensen et al., *Virology* 2001 Dec. 20: 291(2):324-34 or Oroczo et al. (2005) *J Virol* 79, 9503-9514, both of which are incorporated by reference for their disclosures of such hybrid L1 proteins. Other types of variants will be evident to a skilled worker. See, e.g., Carter et al., *J Virol* 2006 May; 80(10):4664-72; White et al. (1999) *J Virology* 73, 4882-4889; or Roden et al. (1997) *J Virol* 71, 6247-52, all of which are incorporated by reference herein for their disclosures of other types of suitable variants of L1. Another suitable example of a L1 protein for use in the chimeric VLPs of this invention is an HPV 16 L1 protein which is modified to present HPV16 L2 amino acids 17-36 (RG1 epitope) within the DE-surface loop of HPV16 L1 (Schellenbacher et al. 2013 *J. Invest Dermatol;* 133(12):2706-2713; Slupetzky et al., 2007 *Vaccine* 25:2001-10; Kondo et al. 2008 *J. Med. Virol* 80; 841-6; Schellenbacher et al. 2009 *J. Virol* 83:10085-95; Caldeira et al. 2010 *Vaccine* 28:4384-93 all incorporated herein in the entirety by reference).

A target peptide can be engineered into or onto an L1 or L2 protein at any of a variety of sites of the protein, provided that the insert is displayed on the surface of the VLP and that the insertion does not interfere with the ability of the protein to assemble into a VLP. Crystallization of L1 HPV16 VLP has revealed the atomic structure of the viral capsid, in particular the hypervariable surface loops that contain the immunodominant and conformation-dependent epitopes that are recognized by neutralizing antibodies and determine the viral serotype (Chen et al. (2000) *Molecular Cell* 5, 557-567, incorporated herein by reference). Accordingly, suitable sites for insertion or attachment of a target peptide into the L1 protein will be evident to a skilled worker.

The target peptide may be inserted in or attached to any of loops BC, CD, DE, EF, FG, HI of a papillomavirus L1 polypeptide. In one embodiment of the invention, the target peptide is attached to or inserted into the DE loop of L1, e.g. between amino acids 133 and 134 of BPV1, between amino acids 136 and 137 of HPV16 L1, or between equivalent sites of L1 molecules from other papillomaviruses. In other embodiments of the invention the target peptide is attached or inserted into the helix B4 loop (e.g. between amino acids 430 and 433 of HPV16 L1).

The L1 protein into which an target peptide is attached or inserted can be from any of a variety of types (strains/ genotypes) of papillomavirus (PV) for example human PV (e.g., HPV 1, 2, 3, 4, 5, 6, 8, 9, 11, 15, 16, 17, 18, 23, 27, 31, 33, 35, 38, 39, 45, 51, 52, 58, 66, 68, 70, 76, or 92), bovine PV (e.g., BPV1, BPV2, BPV4, BPV6), or canine oral PV (COPY).

As used herein, the term "antigen" is a molecule capable of being bound by a T-cell receptor. An antigen is additionally capable of inducing a humoral response and/or a cellular immune response leading to the stimulation of B- and/or T-lymphocytes, and preferably with regard to the invention derived herein the antigen stimulates CD8+ T lymphocytes when in complex with an MHC class I molecule. The structural aspect of an antigen that gives rise to a biological response is referred to herein as an "antigenic determinant" or "epitope" and are synonymous. B-lymphocytes respond to foreign antigenic determinants via antibody production, whereas T-lymphocytes are the mediator of cellular immunity. Thus, antigenic determinants or epitopes are those parts of an antigen that are recognized by antibodies, or in the context of an MHC, by T-cell receptors. An antigenic determinant or epitope need not be a contiguous/consecutive sequence or segment of protein and may include various sequences that are not immediately adjacent to one another.

With regard to a particular amino acid sequence, an "epitope" is a set of amino acid residues that is involved in recognition by a particular immunoglobulin, or in the context of T-cells, those residues necessary for recognition by T-cell receptor proteins and/or MHC receptors. The amino acid residues of an epitope need not be contiguous/consecutive. In an immune system setting, in vivo or in vitro, an epitope is the collective features of a molecule, such as primary, secondary and tertiary peptide structure, and charge, that together form a site recognized by an immunoglobulin, T-cell receptor, or HLA molecule.

As used herein "T-cell epitope" means a feature of a peptide or protein which in association with an MHC molecule on the surface of a cell is recognized by a T-cell receptor in the initiation of an immunologic response to the peptide comprising that antigen. Recognition of a T-cell epitope by a T-cell is generally believed to be via a mechanism wherein T-cells recognize peptide fragments of antigens which are bound to MHC class I or class II molecules expressed on antigen-presenting cells. In some embodiments of the present invention, the target peptides comprising the T cell epitope and the chimeric VLPs described herein find use in the detection of antigen presenting cells having MHC molecules capable of binding and displaying the T cell epitopes of the target peptides. A T cell epitope typically requires a short peptide that is bound to a class I or II MHC molecule, forming a ternary complex (MHC class I alpha chain, beta-2-microglobulin, and peptide) that can be recognized by a T cell bearing a matching T-cell molecule binding to the MHC/peptide complex with appropriate affinity. Peptides binding to MHC class I molecules are typically 8-14 amino acids in length, and most typically 9 amino acids in length.

As used herein, "HPV" and "human papillomavirus" refer to the members of the family Papillomavirus that are capable of infecting humans. There are two major groups of HPVs defined by their tropism (genital/mucosal and cutaneous groups), each of which contains multiple virus "types" or "strains/genotypes" (e.g., HPV 16, HPV 18, HPV 31, HPV 32, etc.).

According to the World Health Organization, "a vaccine is a biological preparation that improves immunity to a particular disease. A vaccine typically contains an agent that resembles a disease-causing microorganism, and is often made from weakened or killed forms of the microbe, its toxins or one of its surface proteins. The agent stimulates the body's immune system to recognize the agent as foreign, destroy it, and "remember" it, so that the immune system can more easily recognize and destroy any of these microorganisms that it later encounters." See www.who.int/topics/vaccines/en/.

The term "VLP vaccine" refers to a formulation which contains 1, 2, 3, 4, 5, or more chimeric VLP of the present invention. Compositions comprising the chimeric VLP of this invention will typically be in a form that is capable of being administered to a subject to redirect existing immunity and inhibit the proliferation, growth, and/or metastasis of a tumor. Typically, a VLP vaccine comprises a conventional saline or buffered aqueous solution medium in which the composition of the present invention is suspended or dissolved, although administration of dry powder, for example by inhalation, and even formulation with an additional adjuvant, such as alum, is also contemplated. The composition of the present invention can be used to inhibit the proliferation, growth, and/or metastasis of a tumor. Upon introduction into a host, a chimeric VLP-containing composition of the invention (e.g., a VLP vaccine) is able to provoke an immune response including, but not limited to, the production of cytokines and/or the activation of cytotoxic T cells, antigen presenting cells, helper T cells, dendritic cells and/or other cellular responses.

As used herein, "therapeutic" compositions are compositions that are designed and administered to patients having a tumor. Therapeutic compositions (e.g., therapeutic chimeric VLP-containing compositions) are used to treat benign or malignant tumors. In some embodiments of this invention, the chimeric VLPs are administered to a subject who previously had a tumor and is currently apparently tumor/cancer free to inhibit the recurrence of the tumor/cancer.

The terms "inhibiting," "reducing," or "prevention," or any variation of these terms, when used in the claims and/or the specification includes any measurable decrease or complete inhibition to achieve a desired result, such as inhibiting, reducing, or preventing tumor growth, proliferation and/or metastasis.

Throughout this application, the term "about" is used to indicate that a value includes the standard deviation of error for the device or method being employed to determine the value.

A "subject," or "subject in need thereof" as used herein, includes any animal that has a tumor/cancer or has had a tumor/cancer. Suitable subjects (patients) include laboratory animals (such as mouse, rat, rabbit, guinea pig or pig), farm animals (such as cattle), sporting animals (such as dogs or horses), domestic animals or pets (such as a horse, dog or cat), non-human primates, and humans.

The terms "protein," "polypeptide," and "peptide," as used herein, are not restricted to any particular number of amino acids; these terms are sometimes used interchangeably herein. The properties and amino acid sequences of the proteins of the invention, and of the nucleic acids encoding them, are well-known and can be determined routinely, as well as downloaded from various known databases. See, e.g., the NCBI GenBank databases. Some sequences are provided herein. However, some sequence information is routinely updated (e.g. to correct mistakes in the previous entries), so updated (corrected) information about the proteins and nucleic acids encoding them is included in this application. Information provided in the sequence databases discussed herein is incorporated by reference in the present application.

As used herein, the term "chimeric VLP" is intended to denote VLPs that comprise a target peptide. This term is not intended to confer any meaning concerning the specific manner in which the target peptide is bound or attached together to the VLP or the specific manner in which the target peptide is inserted into the VLP. In an embodiment of the invention the target peptide is conjugated to the VLP via a disulfide linkage, maleimide, or amide linkage.

The term "HPV" and "human papillomavirus" refer to the members of the family Papillomavirus that are capable of infecting humans. There are two major groups of HPVs defined by their tropism (genital/mucosal and cutaneous groups), each of which contains multiple virus "types" or "strains" (e.g., HPV5, HPV 16, HPV 18, HPV 31, HPV 32, etc.).

"Checkpoint inhibitor" is a type of drug that blocks certain proteins, "checkpoint proteins", that are made by some types of immune system cells, such as T cells, and some cancer cells. Checkpoint proteins help keep immune responses in check and can keep T cells from killing cancer cells. When checkpoint proteins are inhibited, the brakes on the immune system are released and T cells are better able to kill cancer cells. Examples of checkpoint proteins found on T cells or cancer cells include PD-1/PD-L1 and CTLA-4/B7-1/B7-2, CD86, GITR, LAG3, VISTA, TIGIT and CD137L. Examples of checkpoint inhibitors include without limitation, ipilimumab (Yervoy®), pembrolizumab (KEYTRUDA®), and nivolumab (OPDIVO®), Atezolizumab (TECENTRIQ®), Avelumab (BAVENCIO®), Durvalumab (IMFINZI®).

"MHC" or "major histocompatibility complex" is a group of genes that code for proteins found on the surfaces of cells that help the immune system recognize foreign substances. MHC proteins are found in all higher vertebrates. There are two main types of MHC molecules, MHC class I and MHC class II. In humans there are three different genetic loci that encode MHC class I molecules (the MHC-molecules of the human are also designated human leukocyte antigens (HLA)): HLA-A, HLA-B, and HLA-C. HLA-A*01, HLA-A*02, and HLA-A*11 are examples of different MHC class I alleles that can be expressed from these loci.

It is contemplated that one or more members of a list provided herein may be specifically excluded from or included in a claimed invention.

Methods for making VLP are known in the art, see e.g., U.S. Pat. Nos. 9,149,503 and 9,580,474, which are incorporated herein by reference. One aspect of the invention is a method for making a chimeric VLP (or a polypeptide component thereof) of the invention. In one aspect of the invention, T cell epitopes are synthesized using conventional methods as modified for the particular amino acid sequences. Such techniques include, e.g., methods well known to those skilled in the art of peptide synthesis, e.g., solution phase synthesis (see Finn et al. in *Proteins*, $3^{rd}$ Ed., Neurath and Hill (Eds), Academic Press, NY, 2, 105-253, 1976), or solid phase synthesis (see Barany et al. In: The Peptides, Gross and Meienhofer (Eds.), Academic Press, NY, 3-284, 1979), or stepwise solid phase synthesis as reported by Merrifield et al. (1963) *J. Am. Chem. Soc.* 85, 2149-2154), the contents of each of which are incorporated herein by reference. Other references to peptide synthesis techniques include peptides synthesized by the Fmoc-polyamide mode of solid-phase peptide synthesis as disclosed by Lu et al. (1981) *J. Org. Chem.* 46, 3433, peptides synthesized using an Fmoc/tBu procedure (Atherton et al. In: Solid Phase Peptide Synthesis: A Practical Approach, IRL Press, Oxford, 1989). Fmoc amino acids can be obtained from various vendors, e.g., Chem-Impex International (Wood Dale, Ill., USA), Merck Biosciences (Nottingham, UK), and Bachem UK Ltd. (St. Helens, UK). The synthesized peptide may be attached to the VLP using methods known in the art. In an embodiment of this invention the method for making the chimeric VLP described herein comprises assembling a VLP from the papilloma virus L1 protein by methods known in the art, subjecting the VLP to reducing conditions sufficient to reduce the VLP but while still maintaining the capsid like icosahedron structure of a VLP, and conjugating a target peptide to the VLP thereby forming the chimeric VLP. The target peptide may be conjugated to the reduced or activated VLP via a disulfide, a maleimide or an amide linkage. For example, in an embodiment of this invention the target peptide is conjugated to a sulfhydryl group of a cysteine on either an L1 or L2 protein or both the L1 and L2 proteins of the chimeric VLP via a disulfide linkage or a maleimide linkage. The target peptide may be conjugated to a sulfhydryl groups of a cysteine on either an L1 or L2 protein or both the L1 and L2 proteins of the chimeric VLP via a disulfide linkage or a maleimide linkage. The reduced cysteines may be on the surface of the VLP. In an embodiment of this invention the L1 or L2 proteins of the VLP may comprise an average of one target peptide, two target peptides, three target peptides, four target peptides, or five target peptides per L1 or L2 protein. In an embodiment of this invention an average of three to five target peptides are conjugated to each L1 or L2 protein of the chimeric VLP. In an embodiment of this invention at least 30% of the surface cysteines of the VLP comprise target peptide. In an embodiment of this invention about 35%, 40%, 45%, 50%, 55%, 60%, 65%, 70%, 75%, 80%, 85%, 90%, 95%, 97%, 99% or 100% of the surface cysteines of the VLP comprise a target peptide. In an embodiment of this invention about 30% to 50% of the surface cysteines of the VLP comprise target peptide.

In an embodiment of the invention the target peptide may be conjugated to a lysine or an arginine on either the L1 or L2 protein or both the L1 and L2 proteins of the chimeric VLP via an amide linkage. The lysines and/or arginines conjugated to the target peptide may be on the surface of the VLP. In an embodiment of this invention at least 30% of the surface lysines and/or surface arginines of the VLP comprise target peptide. In an embodiment of this invention about 35%, 40%, 45%, 50%, 55%, 60%, 65%, 70%, 75%, 80%, 85%, 90%, 95%, 97%, 99% or 100% of the surface lysines and/or surface arginines of the VLP comprise a target peptide. In an embodiment of this invention about 30% to 50% of the surface lysines and/or surface arginines of the VLP comprise a target peptide.

In an embodiment of this invention about 30% to 50% of the surface lysines and surface cysteines of the VLP are conjugated to a target peptide. In an embodiment of this invention at least 30% of the surface lysines and/or surface cysteines of the VLP are conjugated to a target peptide. In an aspect of this invention the surface cysteines and surface lysines are conjugated to the target peptide such that about 35%, 40%, 45%, 50%, 55%, 60%, 65%, 70%, 75%, 80%, 85%, 90%, 95%, 97%, 99% of the surface cysteines and lysines are conjugated to the target peptide. The lysines and cysteines may be conjugated to target peptides having the same CD8+ T cell epitope or to target peptides having different CD8+ T cell epitope such that the VLP is conjugated to multiple target peptides having different CD8+ T cell epitopes.

In an embodiment of this invention about 30% to 50% of the surface arginines and surface cysteines of the VLP are conjugated to a target peptide. In an embodiment of this invention at least 30% of the surface arginines and/or surface arginines of the VLP are conjugated to a target peptide. In an aspect of this invention the surface cysteines and surface arginines are conjugated to the target peptide such that about 35%, 40%, 45%, 50%, 55%, 60%, 65%, 70%, 75%, 80%, 85%, 90%, 95%, 97%, 99% or 100% of the surface cysteines and surface arginines are conjugated to the target peptide. The arginines and cysteines may be conjugated to target peptides having the same CD8+ T cell epitope or to target peptides having different CD8+ T cell epitope such that the VLP is conjugated to multiple target peptides having different CD8+ T cell epitopes.

In an embodiment of this invention all the target peptides conjugated to the VLP comprise the same CD8+ T cell epitope. In another embodiment of this invention the VLP is conjugated to multiple target peptides wherein the target peptides comprising different CD8+ T cell epitopes. The CD8+ T cell epitopes may be of the same pathogen or different pathogens.

Also an embodiment of this invention is a composition comprising a population of chimeric VLPs described herein and a pharmaceutically acceptable excipient. The population of chimeric VLPs may be a population of identical chimeric VLPs or a population of non-identical chimeric VLPs.

Alternatively, a polypeptide, e.g., a target peptide, and the L1 or L2 protein of the invention, can be prepared recombinantly. The present invention provides recombinant cloning and expression vectors containing DNA, as well as host cell containing the recombinant vectors. Expression vectors comprising DNA may be used to prepare the polypeptides, e.g. the target peptides and the L1 and L2 proteins, encoded by a DNA. A method for producing polypeptides comprises culturing host cells transformed with a recombinant expression vector encoding the polypeptide, under conditions that promote expression of the polypeptide, then recovering the expressed polypeptides from the culture. The skilled artisan will recognize that the procedure for purifying the expressed polypeptides will vary according to such factors as the type of host cells employed, and whether the polypeptide is membrane-bound or a soluble form that is secreted from the host cell. Polypeptides of the invention can include various leader sequences that direct trafficking or assist in purification.

Any suitable expression system may be employed. The vectors include a DNA encoding a polypeptide, e.g., target peptide, a L1 or L2 protein, or polypeptides comprising the L1 or L2 protein and a target peptide of the invention, operably linked to suitable transcriptional or translational regulatory nucleotide sequences, such as those derived from a mammalian, microbial, viral, or insect gene. Examples of regulatory sequences include transcriptional promoters, operators, or enhancers, an mRNA ribosomal binding site, and appropriate sequences which control transcription and translation initiation and termination. Nucleotide sequences are operably linked when the regulatory sequence functionally relates to the DNA sequence. Thus, a promoter nucleotide sequence is operably linked to a DNA sequence if the promoter nucleotide sequence controls the transcription of the DNA sequence. An origin of replication that confers the ability to replicate in the desired host cells, and a selection gene by which transformants are identified, are generally incorporated into the expression vector.

Suitable host cells for expression of polypeptides include prokaryotes, yeast or higher eukaryotic cells. Mammalian or insect cells are suitable for use as host cells. Appropriate cloning and expression vectors for use with bacterial, fungal, yeast, and mammalian cellular hosts are described, for example, in Pouwels et al In: Cloning Vectors: A Laboratory Manual, Elsevier, N.Y., 1985. Cell-free translation systems could also be employed to produce polypeptides using RNAs derived from DNA constructs disclosed herein. In general, molecular biology methods referred to herein are well-known in the art and are described, e.g., in Sambrook et al., Molecular Cloning: A Laboratory Manual, current edition, Cold Spring Harbor Laboratory, Cold Spring Harbor, N.Y., and Ausubel et al., Current Protocols in Molecular Biology, John Wiley & sons, New York, N.Y.

Methods for allowing polypeptides to assemble into VLPs are well-known and conventional, as are methods for purifying them for use in subjects. For suitable conditions for self-assembly, see, e.g., the methods described in the Examples herein, or in Kirnbauer et al. (1993) *J Virol* 67, 6929-6936; Volpers et al. (1994) *Virology* 200, 504-512; or Chen et al., *J Mol Biol* 2001 Mar. 16; 307(1):173-82, all of which are incorporated by reference for the descriptions of such methods.

The methods of the present invention include treatment of existing tumors with an effective amount of the inventive chimeric VLPs. The methods of this invention comprise administering the chimeric VLPs of this invention to a subject in need thereof in an amount sufficient to inhibit tumor growth, progression or metastasis. In an embodiment of the methods of this invention the chimeric VLP is administered to a subject in need thereof in an amount sufficient to stimulate cytokine production, and/or cellular immunity, particularly innate immunity, including stimulating the cytotoxic activity of macrophages and natural killer cells. In aspects of this invention a subject in need thereof is a subject who has previously been treated for a tumor and is currently deemed cancer-free or disease-free in accordance with medical standards.

An aspect of the invention is a method for treating a cancer in a subject in need thereof by administering a chimeric VLP of this invention to the subject wherein the CD8+ epitope of the target peptide is of a pathogen that has a tropism for the tissue that is the source of the cancer (the "source tissue"). The method comprises determining the source tissue, determining if the subject has been actively vaccinated against, or infected with, a pathogen that has a tropism for the source tissue, and then administering to the subject an effective amount of a chimeric VLP of this invention wherein the CD8+ epitope of the target peptide is of the antigenic determinant in the vaccine previously administered to the subject or the pathogen that infected the subject.

It is known in the art that some viruses display a tropism for particular type of tissue. For example: viruses that display a tropism for brain tissue include without limitation, JC virus, measles, LCM virus, arbovirus and rabies; viruses that display a tropism for eye tissue include without limitation herpes simplex virus, adenovirus, and cytomegalovirus; viruses that display a tropism for nasal tissue include without limitation, rhinoviruses, parinfluenza viruses, and respiratory syncytial virus; viruses that display a tropism for oral tissue, e.g., oral mucosa, gingiva, salivary glands, pharynx, include without limitation, herpes simplex virus type I and type II, mumps virus, Epstein barr virus, and cytomegalovirus; viruses that display a tropism for lung tissue include without limitation, influenza virus type A and type B, parainfluenza virus, respiratory syncytial virus, adenovirus, and SARS coronavirus; viruses that display a tropism for nerve tissue, e.g., the spinal cord, include without limitation poliovirus and HTLV-1; viruses that display a tropism for heart tissue, include without limitation, Coxsackie B virus; viruses that display a tropism for liver tissue, include without limitation, hepatitis viruses types A, B and C; viruses that display a tropism for gastrointestinal tissue, e.g., stomach, and large and small intestine, include without limitation, adenovirus, rotavirus, norovirus, astrovirus, and coronavirus; viruses that display a tropism for pancreatic tissue, include without limitation, coxsackie B virus; viruses that display a tropism for skin tissue, include without limitation, varicella zoster virus, herpes simplex virus 6, smallpox virus, molluscum contagiousum, papilloma viruses, parvovirus B19, rubella, measles and coxsackie A virus; and viruses that display a tropism for genital tissue, include without limitation, herpes simplex type 2, papillomaviruses, human immunodeficiency virus (HIV).

An aspect of this invention is a method for treating a lung cancer comprising determining if a subject has been actively vaccinated against a pathogen that infects lung cells, e.g., an influenza virus, e.g., influenza virus type A or type B, then administering an effective amount of a chimeric VLP of this invention wherein the CD8+ T cell epitope of the target peptide is of the antigenic determinants of the pathogen contained in the vaccine and which T cell epitope forms a complex with an MHC molecule class I of the subject. In an aspect of a method of this invention for treating a lung cancer includes determining if a subject has been infected with pathogen that infects lung cells, e.g., an influenza virus, e.g., influenza virus type A or type B, then administering an effective amount of a chimeric VLP of this invention wherein the CD8+ T cell epitope of the target peptide is of that pathogen and which T cell epitope forms a complex with an MHC class I molecule of the subject.

An aspect of the invention is a method for treating an oral cancer, which are part of the group of cancers commonly referred to as head and neck cancers, by administering a chimeric VLP of this invention wherein the CD8+ epitope of the target peptide is of a pathogen that has a tropism for oral tissue, e.g., a mumps virus, Epstein barr virus, cytomegalovirus, or a herpes simplex virus type 1. The method comprises determining if a subject in need thereof has been actively vaccinated against, or infected with, e.g., a mumps virus, Epstein barr virus, cytomegalovirus, or a herpes simplex virus type 1, and if the subject has been vaccinated or infected previously then administering to the subject a chimeric VLP of this invention wherein the CD8+ epitope of the target peptide is of a mumps virus or a measles virus or of the antigenic component of the vaccine the subject had received, or of the pathogen, i.e., mumps, measles, Epstein barr virus, cytomegalovirus, or a herpes simplex virus type 1, that had previously infected the subject.

An aspect of this invention is a method for stimulating the cytotoxic activity of macrophages and natural killer cells by administering to a subject in need thereof an effective amount of a chimeric VLP of this invention. The macrophages and natural killer cells may be those present in the tumor microenvironment. In an aspect of this invention, the chimeric VLPs are administered to the subject in an amount effective to stimulate the cytotoxic activity of macrophages and natural killer cells already present in the tumor microenvironment. In an aspect of this invention, the chimeric VLPs are administered to the subject in an amount effective to attract macrophages and natural killer cells to the tumor microenvironment.

In an aspect of this invention, the chimeric VLPs are administered to the subject in an amount effective to bind sufficient numbers of antibodies to the target peptide to attract and stimulate macrophages, neutrophils and natural killer cells.

An aspect of this invention is a method for redirecting the cytotoxic activity of an existing memory CD8+ T cell to a tumor cell or tumor microenvironment by administering to a subject in need thereof an effective amount of the chimeric VLP of this invention. Preferably, the T cell epitope of the target peptide of the chimeric VLP is from a pathogen for which the subject has been actively vaccinated or from a pathogen that has previously infected the subject and the subject has memory CD8+ T cells that recognize the T cell epitope in complex with an MHC class I molecule on the tumor cells. In an aspect of this invention the effective amount of the chimeric VLP is an amount sufficient to attract the memory CD8+ T cell to the tumor microenvironment. In an aspect of this invention the effective amount of the chimeric VLP is an amount sufficient to stimulate the memory CD8+ T cell present in the tumor microenvironment.

An aspect of this invention is a method for introducing a target peptide as described herein into a tumor microenvironment by administering to a subject in need thereof a chimeric VLP of this invention. In an aspect of this invention the CD8+ T cell epitope of the target peptide is released from the VLP into the tumor microenvironment in an amount sufficient to stimulate memory CD8+ T cells in the microenvironment. In an aspect of this invention the chimeric VLP and/or target peptide of the chimeric VLP is susceptible to cleavage by a proteolytic enzyme in the tumor microenvironment and the position of the target cleavage site in the chimeric VLP or the target peptide is such that cleavage of the target site releases all or a portion of target peptide comprising the CD8+ T cell epitope from the chimeric VLP into the tumor microenvironment. In an aspect of this invention the cleavage site is recognized by a furin, a matrix metalloproteinases (MMPs) e.g., MMP, 1, 2, 3, 7, 8, 9, 11, 13, 14, or 19, an ADAM (a disintegrin and metalloproteinase), e.g., ADAMS 8, 9, 10, 15, 17 or 28, a Cathepsin, e.g., Cathepsin B, D, D, G, or H, N. Elastase, Proteinase-3, Azurocidin, or ADAMTS-1. Sufficient amounts of the chimeric VLP are readily determined by the skilled artisan and it will be appreciated that the amount will depend on, e.g., the characteristics of the subject, e.g., age, weight, gender, medical condition of the subject, and the characteristics of the tumor, e.g., type, volume, and developmental status.

In an aspect of this invention the chimeric VLP and/or target peptide of the chimeric VLP is susceptible to cleavage by a proteolytic enzyme within the tumor cell and the position of the target cleavage site in the VLP or target peptide is such that cleavage of the target site releases all or a portion of target peptide comprising the CD8+ T cell epitope from the chimeric VLP, which complexes with an MHC class I molecule of the tumor cell. Sufficient amounts of the chimeric VLP are readily determined by the skilled artisan and it will be appreciated that the amount will depend on, e.g., the characteristics of the subject, e.g., age, weight, gender, medical condition of the subject, and the characteristics of the tumor, e.g., type, volume, and developmental status.

In an aspect of the invention, to select an appropriate chimeric VLP(s) of this invention to administer to the subject in need thereof, one ascertains if the subject has been actively vaccinated against a given pathogen, e.g., a parasite, a bacterium, or virus, e.g., measles or polio, and then selects and administers to the subject a chimeric VLP of this invention wherein the CD8+ T cell epitope of the target peptide is from the pathogen against which the subject has been immunized. One may ascertain if a subject has been actively vaccinated against a particular pathogen by reviewing the subjects' medical records or interviewing the subject.

In an aspect of the invention, to select an appropriate chimeric VLP(s) to administer to the subject in need thereof, one ascertains if the subject has been previously infected with a given pathogen, e.g., a parasite, a bacterium, or virus, e.g., measles or polio, and resolved the infection, and then selects and administers to the subject a chimeric VLP wherein the CD8+ T cell epitope of the target peptide is a CD8+ T cell epitope from such pathogen. One may ascertain if a subject has been infected with a particular pathogen by reviewing the subjects' medical records or interviewing the subject. Non-limiting examples of CD8+ T cell epitopes that bind to particular MHC class I molecules are set forth in Table 1 and Table 2. The method may also comprise determining which MHC class I determinant(s) the subject's cells express and then administering a chimeric VLP of this invention wherein the CD8+ T cell epitope of the target peptide is a CD8+ T cell epitope of the antigenic component of the pathogen in the vaccine or of the pathogen that previously infected the subject that forms a complex with the subject's MHC class I determinant(s).

Furthermore, in some embodiments, the chimeric VLPs described herein are administered in conjunction with other cancer treatment therapies, e.g., radiotherapy, chemotherapy, surgery, and/or immunotherapy. In some aspects of this invention, the chimeric VLPs described herein are administered in conjunction with checkpoint inhibitors. The chimeric VLPs of the present invention and other therapies or therapeutic agents can be administered simultaneously or sequentially by the same or different routes of administration. The determination of the identity and amount of therapeutic agent(s) for use in the methods of the present invention can be readily made by ordinarily skilled medical practitioners using standard techniques known in the art.

VLPs have adjuvant properties. In some embodiments, the immunogenicity of the chimeric VLP compositions of this invention can be enhanced by the use of additional non-specific stimulators of the immune response, known as adjuvants. Suitable adjuvants include all acceptable immunostimulatory compounds, such as cytokines, toxins, or synthetic compositions such as alum.

Adjuvants include, but are not limited to, oil-in-water emulsions, water-in-oil emulsions, mineral salts, polynucleotides, and natural substances. Specific adjuvants that may be used include IL-1, IL-2, IL-4, IL-7, IL-12, γ-interferon, GM-CSF, BCG, aluminum salts, such as aluminum hydroxide or other aluminum compound, MDP compounds, such as thur-MDP and nor-MDP, CGP (MTP-PE), lipid A, and monophosphoryl lipid A (MPL), or inactivated microbial agents. RIBI, which contains three components extracted from bacteria, MPL, trehalose dimycolate (TDM), and cell wall skeleton (CWS) in a 2% squalene/Tween 80 emulsion. MHC antigens may even be used. Others adjuvants or methods are exemplified in U.S. Pat. Nos. 6,814,971, 5,084,269, 6,656,462, each of which is incorporated herein by reference).

Various methods of achieving adjuvant affect for the chimeric VLP compositions includes use of agents such as aluminum hydroxide or phosphate (alum), commonly used as about 0.05 to about 0.1% solution in phosphate buffered saline, admixture with synthetic polymers of sugars (CARBOPOL®) used as an about 0.25% solution, aggregation of a protein in the composition by heat treatment with temperatures ranging between about 70° C. to about 101° C. for a 30-second to 2-minute period, respectively. Aggregation by reactivating with pepsin-treated (Fab) antibodies to albumin; mixture with bacterial cells (e.g., *C. parvum*), endotoxins or lipopolysaccharide components of Gram-negative bacteria; emulsion in physiologically acceptable oil vehicles (e.g., mannide mono-oleate (Aracel A)); or emulsion with a 20% solution of a perfluorocarbon (FLUOSOL-DA®) used as a block substitute may also be employed to produce an adjuvant effect. A typical adjuvant is complete Freund's adjuvant (containing killed *Mycobacterium tuberculosis*), incomplete Freund's adjuvants, and aluminum hydroxide.

For administration to humans, a variety of suitable adjuvants will be evident to a skilled worker. These include, e.g., Alum-MPL as adjuvant, or the comparable formulation, ASO4, which is used in the approved HPV vaccine CERVARIX®, AS03, AS02, MF59, montanide, saponin-based adjuvants such as GPI-0100, CpG-based adjuvants, or imiquimod. In embodiments of the invention, an adjuvant is physically coupled to the VLP, or encapsulated by the VLP, rather than simply mixed with them.

In addition to adjuvants, it may be desirable to co-administer biologic response modifiers (BRM) to enhance immune responses. BRMs have been shown to upregulate T cell immunity or downregulate suppresser cell activity. Such BRMs include, but are not limited to, Cimetidine (CIM; 1200 mg/d) (Smith/Kline, PA); or low-dose Cyclophosphamide (CYP; 300 mg/m$^2$) (Johnson/Mead, NJ) and cytokines such as γ-interferon, IL-2, or IL-12 or genes encoding proteins involved in immune helper functions, such as B-7. In embodiments of the invention, these genes are encapsulated by the VLP to facilitate their delivery into a subject.

The preparation of compositions that contain polypeptide or peptide sequence(s) as active ingredients is generally well understood in the art, as exemplified by U.S. Pat. Nos. 4,608,251; 4,601,903; 4,599,231; 4,599,230; 4,596,792; and 4,578,770, all of which are incorporated herein by reference. Typically, such compositions are prepared as injectables either as liquid solutions or suspensions: solid forms suitable for solution in or suspension in liquid prior to injection may also be prepared. The preparation may also be emulsified. The active immunogenic ingredient is often mixed with excipients that are pharmaceutically acceptable and compatible with the active ingredient. Suitable excipients are, for example, water, saline, dextrose, glycerol, ethanol, or the like and combinations thereof. In addition, if desired, the compositions may contain amounts of auxiliary substances such as wetting or emulsifying agents, pH buffering agents, or adjuvants that enhance the effectiveness of the vaccines.

In specific embodiments, vaccines are formulated with a combination of substances, as described in U.S. Pat. Nos. 6,793,923 and 6,733,754, which are incorporated herein by reference.

The compositions comprising the chimeric VLPs of the present invention are in biologically compatible form suitable for administration in vivo to subjects. The pharmaceutical compositions further comprise a pharmaceutically acceptable carrier. The term "pharmaceutically acceptable" means approved by a regulatory agency of the Federal or a state government or listed in the U.S. Pharmacopeia or other generally recognized pharmacopeia for use in animals, and more particularly, in humans. The term "carrier" refers to a diluent, adjuvant, excipient, or vehicle with which the VLP is administered. Such pharmaceutical carriers can be sterile liquids, such as water and oils, including those of petroleum, animal, vegetable or synthetic origin, including but not limited to peanut oil, soybean oil, mineral oil, sesame oil and the like. Water may be a carrier when the pharmaceutical composition is administered orally. Saline and aqueous dextrose may be carriers when the pharmaceutical composition is administered intravenously. Saline solutions and aqueous dextrose and glycerol solutions may be employed as liquid carriers for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried slim milk, glycerol, propylene, glycol, water, ethanol and the like. The pharmaceutical composition may also contain minor amounts of wetting or emulsifying agents, or pH buffering agents.

The pharmaceutical compositions comprising the chimeric VLPs of the present invention can take the form of solutions, suspensions, emulsions, tablets, pills, capsules, powders, sustained-release formulations and the like. Oral formulation may include standard carriers such as pharmaceutical grades of mannitol, lactose, starch, magnesium stearate, sodium saccharine, cellulose, magnesium carbonate, etc. In a specific embodiment, a pharmaceutical composition comprises an effective amount of a chimeric VLP of the present invention together with a suitable amount of a pharmaceutically acceptable carrier so as to provide the form for proper administration to the patient. The formulation should suit the mode of administration.

The pharmaceutical compositions of the present invention may be administered by any particular route of administration including, but not limited to intravenous, intramuscular, intrarticular, intrabronchial, intraabdominal, intracapsular, intracartilaginous, intracavitary, intracelial, intracelebellar, intracerebroventricular, intracolic, intracervical, intragastric, intrahepatic, intramyocardial, intraosteal, intraosseous, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, oral, parenteral, subcutaneous, vaginal, rectal, buccal, sublingual, intranasal, iontophoretic means, or transdermal means. Most suitable routes are intravenous injection or oral administration. In particular embodiments, the compositions are administered at or near the target area, e.g., intratumoral injection.

For parenteral administration in an aqueous solution, for example, the solution should be suitably buffered, if necessary, and the liquid diluent first rendered isotonic with sufficient saline or glucose. These particular aqueous solutions are especially suitable for intravenous, intramuscular, intratumoral, subcutaneous, and intraperitoneal administration. In this connection, sterile aqueous media which can be employed will be known to those of skill in the art in light of the present disclosure. For example, one dosage could be dissolved in isotonic NaCl solution and either added to hypodermoclysis fluid or injected at the proposed site of infusion (see for example, Remington's Pharmaceutical Sciences, 1990). Some variation in dosage will necessarily occur depending on the condition of the subject. The person responsible for administration will, in any event, determine the appropriate dose for the individual subject.

The chimeric VLP-containing compositions of this invention may be administered by inhalation. In certain embodiments a composition can be administered as an aerosol. As used herein the term "aerosol" or "aerosolized composition" refers to a suspension of solid or liquid particles in a gas. The terms may be used generally to refer to a composition that has been vaporized, nebulized, or otherwise converted from a solid or liquid form to an inhalable form including suspended solid or liquid drug particles. Such aerosols can be used to deliver a composition via the respiratory system. As used herein, "respiratory system" refers to the system of organs in the body responsible for the intake of oxygen and the expiration of carbon dioxide. The system generally includes all the air passages from the nose to the pulmonary alveoli. In mammals it is generally considered to include the lungs, bronchi, bronchioles, trachea, nasal passages, and diaphragm. For purposes of the present disclosure, delivery of a composition to the respiratory system indicates that a drug is delivered to one or more of the air passages of the respiratory system, in particular to the lungs.

Additional formulations which are suitable for other modes of administration include suppositories (for anal or vaginal application) and, in some cases, oral formulations. For suppositories, traditional binders and carriers may include, for example, polyalkalene glycols or triglycerides: such suppositories may be formed from mixtures containing the active ingredient in the range of about 0.5% to about 10%, preferably about 1% to about 2%. Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders and contain about 10% to about 95% of active ingredient, preferably about 25% to about 70%.

The chimeric VLP compositions may be formulated into a vaccine as neutral or salt forms. Pharmaceutically-acceptable salts include the acid addition salts (formed with the free amino groups of the peptide) and those that are formed with inorganic acids such as, for example, hydrochloric or phosphoric acids, or such organic acids as acetic, oxalic, tartaric, mandelic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The pharmaceutical compositions of the present invention can also include an effective amount of an additional adjuvant. As noted herein, papillomavirus VLPs have adjuvant properties. Suitable additional adjuvants include, but are not limited to, Freund's complete or incomplete, mineral gels such as aluminum hydroxide, surface active substances such as lysolecithin, pluronic polyols, polyanions, peptides, oil emulsions, dinitrophenol, and potentially useful human adjuvants such as Bacille Calmette-Guerin, Carynebacterium parvum, and non-toxic Cholera toxin.

Under ordinary conditions of storage and use, these preparations contain a preservative to prevent the growth of microorganisms. In all cases the pharmaceutical form must be sterile and must be fluid to the extent that it may be easily injected. It also should be stable under the conditions of manufacture and storage and must be preserved against the contaminating action of microorganisms, such as bacteria and fungi.

The carrier also can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion, and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the chimeric VLPs in the required amount in the appropriate solvent with various ingredients enumerated above, as required may be followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques, which yield a powder of the active ingredient, plus any additional desired ingredient from a previously sterile-filtered solution thereof.

Different aspects of the present invention involve administering an effective amount of a composition comprising the chimeric VLPs to a subject in need thereof. In some embodiments of the present invention, a chimeric VLP comprising a target peptide comprising a CD8+ T cell epitope is administered to the patient to treat a tumor or prevent the recurrence of such tumor. Such compositions will generally be dissolved or dispersed in a pharmaceutically acceptable carrier or aqueous medium.

In the methods of this invention the tumor may be a small lung cell cancer, hepatocellular carcinoma, liver cancer, hepatocellular carcinoma, melanoma, metastatic melanoma, adrenal cancer, anal cancer, aplastic anemia, bile duct cancer, bladder cancer, bone cancer, brain/CNS cancer, breast cancer, cancer of unknown primary origin, Castleman disease, cervical cancer, colon/rectum cancer, endometrial cancer, esophagus cancer, Ewing family of tumors, eye cancer, gallbladder cancer, gastrointestinal carcinoid tumors, gastrointestinal stromal tumor (gist), gestational trophoblastic disease, Hodgkin disease, Kaposi sarcoma, kidney cancer, laryngeal and hypopharyngeal cancer, leukemia, liver cancer, lung cancer, lymphoma, malignant mesothelioma, multiple myeloma, myelodysplastic syndrome, nasal cavity and paranasal sinus cancer, nasopharyngeal cancer. neuroblastoma, oral cavity and oropharyngeal cancer, osteosarcoma, ovarian cancer, pancreatic cancer, penile cancer, pituitary tumors, prostate cancer, retinoblastoma, rhabdomyosarcoma, salivary gland cancer, sarcoma, skin cancer, stomach cancer, testicular cancer, thymus cancer, thyroid cancer, uterine sarcoma, vaginal cancer. vulvar cancer, Waldenstrom Macroglobulinemia, Wilms Tumor, non-Hodgkin lymphoma, Hodgkin lymphoma, Burkitt's lymphoma, lymphoblastic lymphomas, mantle cell lymphoma (MCL), multiple myeloma (MM), small lymphocytic lymphoma (SLL), splenic marginal zone lymphoma, marginal zone lymphoma (extra-nodal or nodal), mixed cell type diffuse aggressive lymphomas of adults, large cell type diffuse aggressive lymphomas of adults, large cell immunoblastic diffuse aggressive lymphomas of adults, small non-cleaved cell diffuse aggressive lymphomas of adults, or follicular lymphoma, head and neck cancer, endometrial or uterine carcinoma, non-small cell lung cancer, osteosarcoma, glioblastoma, or metastatic cancer. In a preferred embodiment, the cancer is a breast cancer, a cervical cancer, an ovarian cancer, a pancreatic cancer or melanoma, e.g., B16F10 melanoma.

Accordingly, particular embodiments of the methods of the present invention relate to the administration of effective amounts of compositions comprising the chimeric VLPs of this invention. As used herein, the term "effective," means adequate to accomplish a desired, expected, or intended result. More particularly, an "effective amount" refers to an amount of a composition of the present invention (e.g., a chimeric papillomavirus VLP comprising a target antigen), either alone or in combination with another therapeutic agent (e.g., papillomavirus VLP comprising native L1 protein, a chemotherapeutic agent, or a checkpoint inhibitor), necessary to provide the desired therapeutic effect, e.g., an amount that is effective to inhibit tumor growth, progression or metastasis, or prevent, alleviate, treat or ameliorate symptoms of disease, e.g., cancer, or prolong the survival of the subject being treated. Those of ordinary skill in the art appreciate that the exact amount required will vary from subject to subject, depending on age, general condition of the subject, the severity of the condition being treated, the particular compound and/or composition administered, and the like. An appropriate "therapeutically effective amount" or "prophylactically effective amount" in any individual case can be determined by one of ordinary skill in the art by reference to the pertinent texts and literature and/or by using routine experimentation. It is understood that reference to a pharmaceutical composition (e.g., a vaccine), its formulation, administration, and the like, can refer to, depending on the context, a chimeric papillomavirus VLP comprising a target peptide, a papillomavirus VLP comprising native L1 protein, or mixtures of the foregoing including mixtures of chimeric VLPs comprising different target peptides. The term "unit dose" or "dosage" refers to physically discrete units suitable for use in a subject, each unit containing a predetermined quantity of the composition calculated to produce the desired responses discussed above in association with its administration, i.e., the appropriate route and regimen. The quantity to be administered, both according to number of treatments and unit dose, depends on the result desired.

Administration of the compositions according to the present invention will typically be via any common route. This includes, but is not limited intravenous, intradermal, intratumoral, subcutaneous, intramuscular, intraperitoneal, respiratory, nasal, oral/ingested, buccal, sublingual or orthotopic administration. In certain embodiments, a VLP-containing composition may be inhaled (e.g., U.S. Pat. No. 6,651,655, which is specifically incorporated by reference). The chimeric VLP-containing compositions of this invention may also be administered directly to the tumor or in the proximity of the tumor such that the VLPs are introduced into the tumor microenvironment. Such compositions would normally be administered as pharmaceutically acceptable compositions that include physiologically acceptable carriers, buffers or other excipients. The dosage of the composition will depend on the route of administration and will vary according to, e.g., the size and health of the subject and the severity of the condition.

In general, the chimeric VLP-containing compositions of this invention may be used alone or in concert with other therapeutic agents at appropriate dosages defined by routine testing in order to obtain optimal efficacy while minimizing any potential toxicity. Other therapeutic agents include e.g. without limitation, chemotherapeutic agents and checkpoint inhibitors. The dosage regimen utilizing a pharmaceutical composition of the present invention may be selected in accordance with a variety of factors including type, species, age, weight, gender, medical condition of the patient; the severity of the condition to be treated; intended goal of treatment (alleviation of symptoms versus cure); the route of administration; the renal and hepatic function of the patient; and the particular pharmaceutical composition employed, and the potency, stability, and toxicity of the particular composition. A physician of ordinary skill can readily determine and prescribe the effective amount of the pharmaceutical composition (and potentially other agents including therapeutic agents) required to prevent, counter, or arrest the progress of the condition, e.g., the tumor/cancer.

Optimal precision in achieving concentrations of the therapeutic regimen within the range that yields maximum efficacy with minimal toxicity may require a regimen based on the kinetics of the pharmaceutical composition's availability to one or more target sites. Distribution, equilibrium, and elimination of a pharmaceutical composition may be considered when determining the optimal concentration for a treatment regimen. The dosages of a pharmaceutical composition disclosed herein may be adjusted when combined to achieve desired effects. On the other hand, dosages of the pharmaceutical composition and various therapeutic agents may be independently optimized and combined to achieve a synergistic result wherein the pathology is reduced more than it would be if either was used alone.

In particular, toxicity and therapeutic efficacy of the pharmaceutical composition may be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effect is the therapeutic index and it may be expressed as the ratio $LD_{50}/ED_{50}$. Pharmaceutical compositions exhibiting large therapeutic indices are preferred except when cytotoxicity of the composition is the activity or therapeutic outcome that is desired. Although pharmaceutical compositions that exhibit toxic side effects may be used, a delivery system can target such compositions to the site of affected tissue in order to minimize potential damage to uninfected cells and, thereby, reduce side effects. Generally, the pharmaceutical compositions of the present invention may be administered in a manner that maximizes efficacy and minimizes toxicity.

In many instances, it will be desirable to have multiple administrations of the VLP-containing composition, usually at most, at least, or not exceeding 1, 2, 3, 4, 5, 6, 7, 8, 9, 10, 11, 12, 13, 14, 15, or more vaccinations including all ranges there between. The vaccinations will normally be at 1, 2, 3, 4, 5, 6, to 5, 6, 7, 8, 9, 10, 11, to 12 week/month/year intervals, including all values and ranges there between, more usually from three to five week intervals.

Data obtained from cell culture assays and animal studies may be used in formulating a range of dosages for use in humans. The dosages of such compositions lie preferably within a range of circulating concentrations that include the $ED_{50}$ with little or no toxicity. The dosage may vary within this range depending upon the dosage form employed and the route of administration utilized. For any composition used in the methods of the invention, the therapeutically effective dose may be estimated initially from cell culture assays. A dose may be formulated in animal models to achieve a circulating plasma concentration range that includes the $IC_{50}$ (the concentration of the test composition that achieves a half-maximal inhibition of symptoms) as determined in cell culture. Such information may be used to accurately determine useful doses in humans. Levels in plasma may be measured, for example, by high performance liquid chromatography.

Upon formulation, solutions will be administered in a manner compatible with the dosage formulation and in such amount as is therapeutically or prophylactically effective. The formulations are easily administered in a variety of dosage forms, such as the type of injectable solutions described herein.

Another aspect of the invention is a kit for treatment according to the present invention. In one embodiment, the kit comprises a vial and optionally a package insert with administration instructions, the vial comprises a chimeric VLP-containing composition for administration according to the methods of the present invention.

Any of the compositions described herein may be included in a kit. In a non-limiting example, reagents for preparing a VLP and/or administering a VLP, by vaccination with VLP can be included in a kit. The kit may further include reagents for assessing the activity of the VLP both in vitro and in vivo. The kits will thus comprise, in suitable container, a VLP composition. In certain aspects, the kit can include reagents and/or devices for administration, e.g., syringe, inhaler or nebulizer. It may also include one or more buffers, compounds, or devices for preparing the composition for administration.

The components of the kits may be packaged either in aqueous media or in lyophilized form. The container means of the kits will generally include at least one vial, test tube, flask, bottle, syringe or other container means, into which a component may be placed, and preferably, suitably aliquoted. Where there is more than one component in the kit, the kit also will generally contain a second, third or other additional container into which the additional components may be separately placed. However, various combinations of components may be comprised in a vial. The kits of the present invention also will typically include a means for containing the containers in close confinement for commercial sale. Such containers may include injection or blow molded plastic containers into which the desired vials are retained.

When the components of the kit are provided in one and/or more liquid solutions, the liquid solution is an aqueous solution, with a sterile aqueous solution being particularly preferred. However, the components of the kit may be provided as dried powder(s). When reagents and/or components are provided as a dry powder, the powder can be reconstituted by the addition of a suitable solvent. It is envisioned that the solvent may also be provided in another container. A kit may also include instructions for employing the kit components as well the use of any other reagent not included in the kit. Instructions may include variations that can be implemented. It is contemplated that such reagents are embodiments of kits of the invention.

Such kits, however, are not limited to the particular items identified above and may include any reagent used for the preparation and/or administration of a chimeric VLP composition of the invention.

Among other uses, kits of the invention can be used in experimental applications. A skilled worker will recognize components of kits suitable for carrying out a method of the invention.

The following examples are offered by way of illustration and not by way of limitation, It is understood that various modifications can be made without departing from the spirit of the invention, and would be readily known to the skilled artisan.

EXAMPLES

Example I. Production of VLPs

A. Baculovirus Expression of HPV L1 Proteins and production of VLPs HPV particles (VLPs) are produced by methods known in the art. Briefly, HPV particles are produced in insect cells from a recombinant baculovirus expressing the papillomavirus major capsid L1 protein. *Trichoplusia ni* (High Five™) cells or *Spodoptera frugiperda* (SF9 cells) are infected with high-titer recombinant baculovirus in Express Five or SF900-III medium under serum-free conditions serum free medium. After 96 h incubation at 27° C., cells are harvested, and the cell pellet is resuspended in extraction buffer (20 mM phosphate buffer pH 6.5, 0.5 M NaCl, 10 mM $MgCl_2$) containing protease inhibitors. Particles are released by freeze-thawing. Nucleic acids are digested by incubation in the presence of a high salt active nuclease. The lysate is clarified by centrifugation at 8,000×g for 30 min and delipidated by Vertrel extraction. The clarified lysate is loaded onto a cushion of 40% sucrose and centrifuged in a SW-28 rotor at 27,000 rpm for 90 min at 4° C. The pellet is resuspended in 20 mM phosphate buffer pH 6.5, 1 M NaCl, 10 mM DTT and 0.03% Tween 80, and stored at 4° C. Purity of the nanoparticle preparation is determined by SDS-PAGE and morphology of particles by electron microscopy (EM). Typical preparations are >90% pure and appear as fully assembled capsid-like 50 nm particles by EM.

HPV particles are also produced in mammalian cells by methods known in the art. Briefly, codon-optimized papillomavirus L1 only or L1 and L2 capsid genes are co-transfected into 293TT cells (human embryonic kidney cells that were transfected with the SV40 Large-T antigen (Pastrana et al., 2004)). The cells co-transfected with the L1 and/or L1/L2 expression vector are maintained for 24 h and are then harvested Briefly, HPV particles are released from 293TT cells by detergent lysis. The cell lysate is incubated overnight at 37° C. The matured HPV particles is solubilized by addition of sodium chloride to the lysate and the lysate is clarified by low speed centrifugation. The capsids are separated from cell debris and detergent by high salt extraction followed by ultracentrifugation through an Optiprep (iodixanol) step gradient according to manufacturer's instructions. Purity of the preparation is determined by SDS-PAGE and morphology of particles by electron microscopy (EM). Typical preparations are >90% pure and appear as fully assembled capsid-like 50 nm particles by EM.

HPV particles are also produced via transfection of papillomavirus L1 only or L1 and L2 capsid genes into 293EXPI cells. The cells co-transfected with the L1 and/or L1/L2 expression vector are maintained for 72 hrs and are then harvested. HPV particles are released from 293EXPI cells by detergent lysis and the lysate is incubated overnight at 37° C. with a mild detergent (e.g. Brij58 or Triton X-100). The particles in the overnight incubated lysate are then solubilized by addition of sodium chloride. The lysate is then clarified by low-speed centrifugation. Capsids are separated from cell debris and detergent by high salt extraction followed by ultracentrifugation through an Optiprep (iodixanol) step gradient according to manufacturer's instructions. Purity of the nanoparticle preparation is determined by SDS-PAGE and morphology of particles by electron microscopy (EM). Typical preparations are >90% pure and appear as fully assembled capsid-like 50 nm particles by EM B. Attachment of Target Peptide to HPV VLP Chimeric VLPs comprising target peptides comprising an terminal cysteine, one of the CD8+ T cell epitopes having the sequence FMYSDFHFI (SEQ ID NO: 136) (influenza), or GILGFVFTL SEQ ID NO: 119 (influenza), or KLWESPQEI (SEQ ID NO: 6) (measles), or FLPSDFFPSV (SEQ ID NO: 69) (HepB), or SLPRSRTPI (SEQ ID NO: 218) (chicken pox virus) or SAPLPSNRV (SEQ ID NO: 219) (chicken pox virus) and an enzyme cleavage site (e.g., RRRR or RVKR) between the cysteine and the T cell epitope, (e.g. C—RRRR-epitope), are prepared by conjugating the target peptides to the HPV16(K)-L1 VLPs of Example 1.A via maleimide conjugation. Briefly the HPV VLP, in 50 mM NaHCO$_3$ pH 8.4 at 14 mM in L1 protein concentration, are mixed with a commercial heterobifunctional cross-linker 4-(N-maleimidomethyl)-cyclohexane-1-carboxylate (sSMCC) (Pierce Endogen, Rockfort, IL) to a final sSMCC/L1 protein (mol/mol) ratio of about 100. The reaction proceeds for 1 h at 2-8° C. and is then desalted by dialysis against a pH 6.2 buffer containing 10 mM Histidine, 0.5 M NaCl, 0.015% polysorbate 80 to generate sSMCC activated HPV VLPs. The maleimide equivalents are determined by the DTNB assay (See, Fan et al., *Vaccine* (2004) Vol. 22: 2993-3003; Ionescu et al. *J. Pharmaceutical Sciences*, Vol. 95(1): 70-79 (January 2006)). The target peptides are dissolved in N2-sparged buffer and each is mixed with sSMCC-activated HPV VLPs to a thio/maleimide (mom/mol) ratio of about 3. The reaction proceeds for about 15 h at 2-8° C. Both samples are then treated with β-mercaptoethanol to quench any excess maleimide. Finally, the samples are dialyzed (Dispodialyser MWCO 300000 Spectrum Industries Inc., Rancho Dominguez, CA) against 0.5 M NaCl and 0.015% polysorbate 80.

Example 2. VLP Induction of Cytokines by BMDC and Macrophages

Chimeric HPV VLPs (20 µg) of Example 1 comprising the target peptides, or HPV VLPs (20 µg) without a target peptide, or phosphate buffered saline (PBS, 200) are added into in vitro cultures of bone-marrow derived dendritic cells (BMDCs, $10^6$ cells/well) and primary macrophages. The BMDCs and macrophages that are harvested from C57BL6 mice. After 24 hours of culture at 37° C. the supernatants are harvested from the cell cultures and the cytokine profiles are quantified using a mouse 32plex luminex Assay.

Results: BMDCs and macrophages exposed to VLPs with or without the target peptides produce elevated levels of pro-inflammatory cytokines in vitro as compared to control BMDCs and macrophages exposed to PBS only.

Example 3. VLP Induction of Cytokine Production by BMDCs Co-Cultured with T Cells BMDCs are co-cultured for 48 h at 37° C. with highly purified, syngeneic T cells (ratio 1:1) in the presence of the chimeric VLPs comprising the target peptides that are produced as described in Example 1 above (10 µg/ml), HPV16 (K)-L1 VLPs (10 µg/ml) or rIFN-γ (1000 U/ml). As controls, BMDCs are cultured in medium alone or are cultured in the presence of the chimeric VLPs of Example 1 (10 µg/ml), HPV16(K)-L1 VLPs (10 µg/ml), or rIFN-γ in the absence of T cells. Each culture condition is performed at least in duplicate. IL-12p70 production is determined for each culture condition using standard procedures.

Example 4. VLPs Bind Tumor Cells In Vivo

A. Method: Mice with or without SHIN-3 DSR ovarian tumors are administered an intraperitoneal injection of $1\times10^8$ IU of the HPV16-Luc (luciferase) pseudovirus (PsV) (prepared as described in Buck et al. *Journal of Virology*, (2004), 78:751-757 or Hung et al. *PLoS One* (2012); 7(7): e40983 incorporated herein by reference) in 100 µl PBS or PBS with 1% i-carrageenan (carrageenan inhibits HPV binding to cells). Forty-eight hours later, luciferin substrate is administered and bioluminescence is measured. A region of interest is drawn around the peritoneal cavity and the average radiance is calculated. All data are representative of n=5/group.

Results: HPV16-Luc PsV bind to SHIN-3 DSR ovarian tumors in vivo.

B. Method: Human ovarian tumors passaged only in immune-compromised animals are subcutaneously implanted into mice. When the tumors are between 7 and 15 mm in diameter, animals receive an intratumoral injection of 50 µl PBS or 50 µl of HPV16-Luc PsV (~1 µg/u1). Animals without tumors receive a subcutaneous injection in their hind flank of 50 µl PBS or 50 µl HPV16-Luc PsV (~1 µg/ul). Luminescence images are recorded the day after the HPV-16/LucPsV injection. An integration time of 2 min is used for luminescence image acquisition. Luminescence values are reported as average radiance.

Results: HPV16-Luc PsV bind and infect established xenograft human ovarian tumors but not healthy tissue in vivo.

Example 5. VLPs Immuno-Modulation of Tumor Micro-Environment

Method: On each of days 1 to 8, 100 µg of HPV VLPs of Example 1 with or without a target peptide are administered into mice bearing tumors. As a control, tumor bearing mice are administered 1000 of PBS on each day for 8 days.

Twenty-four hours after the last injection (day 9) mice are sacrificed and tumors are harvested and homogenized. Supernatants are collected and subjected to cytokine profiling using mouse 32plex luminex Assay.

Results: Tumors of mice treated with the VLPs of Example 1 exhibit elevated levels of pro-inflammatory cytokines and chemo-attractants as compared to tumors of mice treated with PBS.

Example 6. VLPs Immuno-Modulation of Tumor Micro-Environment

Method: On each of days 1 to 8, the HPV VLP and each of the chimeric VLPs of Example 1 (100 µg) are administered to groups of mice bearing tumors. As a control, tumor bearing mice are administered 1000 of PBS on each of days 1-8.

Twenty-four hours later (day 9), mice are sacrificed and tumors are harvested and dissociated into single cell suspension. Red blood cells are removed from the suspension using RBC lysis buffer. Flow cytometry is performed using BD Facscaliber with anti-mouse antibodies specific for CD45, MHC II, CD86, CD11b, F4/80 and Ly6G and the cell composition of the tumors are compared.

Results: Administration of the VLPs of Example 1 with or without target peptide induce dramatic changes in tumor immune cell composition as compared to tumors from mice treated with PBS.

Example 7. VLPs Immunotherapy Induces Systemic Durable Anti-Tumor Immunity

Method: The HPV VLP and each of the chimeric VLPs of Example 1 (100 µg) were directly injected into B16F10 melanomas in a mouse. The tumors necrotic centers rapidly form within the tumors and, some of the treated mice eliminate the tumors altogether.

Mice that completely eliminate the tumor are re-challenged by injecting B16F10 cells into their contralateral flanks 4 weeks after complete disappearance of their primary tumors is confirmed. Mice previously cured of primary B16F10 flank tumors by intratumoral injection of chimeric VLPs exhibit an increase in resistance to secondary rechallenge. This indicates that direct injection of primary tumors with chimeric VLPs nanoparticles induces a protective systemic immune response against B16F10 tumors.

Results: The chimeric VLPs with a target peptide induce systemic durable anti-tumor immunity

Example 8. Chimeric VLPs are Able to Re-Direct Unrelated T-Cell Immunity to Tumor and Foster Clearance Method: The murine ID8 ovarian cancer cell line overexpressing luciferase will be co-cultured with OT-1 CD8+ T-cells that are specific to the ovalbumin peptide epitope SIINFEKL (SEQ ID NO: 220). The VLPs with or without a SIINFEKL (SEQ ID NO: 220)-containing target peptide will then be added to the co-cultures.

Result: It is contemplated that no cell death (in the form of diminished luciferase signal) will occur with the VLPs without the target peptide co-cultured with OT-1 CD8+ T-cells and murine ID8 ovarian cancer cell line. In contrast, it is contemplated that tumor cell death in the form of diminished luciferase signal will be observed in the ID8/OT-1 T cell co-cultures that received chimeric VLPs comprising the SIINFEKL (SEQ ID NO: 220)-containing target peptide ("OVA-chimeric VLP").

In vivo Method: C57/BL6 mice 10 weeks of age having ovarian tumors are generated by injection of ID8 murine ovarian cancer cell line into the mice. One hundred µg of OVA-chimeric VLP is i.p injected into each mouse. Controls are (a) mice i.p injected with 100 µg/mouse of the VLP of Example 1 without a target peptide and (b) mice i.p injected with 100 µg/mouse of the chimeric VLPs of Example 1. The VLPs are administered to the mice every week for four weeks and $2.5 \times 10^6$ CD8+ T cells of OT-1 above, are injected intraperitoneally twice, i.e., once every other week, into the mice. All mice are observed for survival. A small fraction of the mice in each group are sacrificed 1 week after the last treatment with the VLPs. Ovarian tumors are harvested for measurement for gross histology and infiltrating T-cells.

Results. The tumors of mice treated with the OVA-chimeric VLP are contemplated to have smaller tumor mass than the tumors of mice treated with VLP without the target peptide and the tumors of mice treated with chimeric VLP of Example 1. Tumor infiltrating lymphocytes are assessed for CD8+ T cells specific for SIINFEKL (SEQ ID NO: 220) by using SIINFEKL (SEQ ID NO: 220)-loaded H-2Kb tetramer staining. The percentage of SIINFEKL (SEQ ID NO: 220) specific CD8+ T cells in total TILs (mean±SD) are also analyzed.

Example 9. Chimeric VLPs Able to Re-Direct Unrelated Human Childhood Vaccine T-Cell Immunity to Tumor Groups of HLA-A*0201 (AAD) transgenic C57BL/6 mice are injected subcutaneously three times with one-tenth of a dose of the chimeric VLPs of Example 1 at one week intervals. Mice are euthanized a week following the last immunization and splenocytes are collected to be analyzed for HLA-A2-restricted, childhood vaccine antigen specific responses using the FMYSDFHF (SEQ ID NO: 136), KLWESPQEI (SEQ ID NO: 6), or FLPSDFFPSV (SEQ ID NO: 69), or SLPRSRTPI (SEQ ID NO: 218) or SAPLPSNRV (SEQ ID NO: 219) peptides via immunofluorescence staining and interferon-gamma CD*+ T-cell activation assays. Following the end of vaccination schedule, splenocytes are co-cultured with the chimeric VLPs of Example 1 comprising target peptide containing a FMYSDFHF (SEQ ID NO: 136), KLWESPQEI (SEQ ID NO: 6), or FLPSDFFPSV (SEQ ID NO: 69), or SLPRSRTPI (SEQ ID NO: 218) or SAPLPSNRV (SEQ ID NO: 219) and are assessed for the re-activation of T cells utilizing immunofluorescence staining and interferon-gamma CD*+ T-cell activation assays. Naked VLPs, i.e., VLPs that do not comprise target peptides are used as controls. Binding and anti-tumor effect of VLPs are tested via luminescence imaging to measure in vitro cytotoxicity. Several luciferase-expressing HLA-A2-positive tumor lines such as ID8/A2 (ovarian), B16/A2 (melanoma), TC-1/A2 (cervical cancer) are co-cultured with splenocytes from HLA-A*0201 (AAD) transgenic mice vaccinated with the chimeric VLPs. As these tumor cell lines are not antigenically related to CD8+ T cell epitope of the target peptides, no tumor-killing is observed. Likewise, the addition of naked VLPs has no or little tumor killing effect.

Results: It is contemplated that addition of the chimeric VLPs of Example 1 comprising the target peptides comprising FMYSDFHF (SEQ ID NO: 136), KLWESPQEI (SEQ ID NO: 6), or FLPSDFFPSV (SEQ ID NO: 69), SLPRSRTPI (SEQ ID NO: 218) or SAPLPSNRV (SEQ ID NO: 219) into this co-culture renders the tumors susceptible to killing by the cytotoxic T-cells in the splenocyte culture

Example 10. Chimeric VLPs are Able to Re-Direct Unrelated Human Childhood Vaccine T-Cell Immunity to Tumor for Clearance Methods: Establishment of tumors: HLA-A*0201 (AAD) transgenic mice are intraperitoneally (IP) injected with luciferase-expressing ID8/A2 tumor cells.

Generation of the childhood vaccine response: following tumor cell injection, the HLA-A*0201 (AAD) transgenic mice are actively immunized with one-tenth of the a human childhood vaccine for influenza virus, measles, hepatitis B or chicken pox with one-week intervals as described in Example 8. The antigenic component of the vaccines comprise the CD8+ T cell epitope FMYSDFHFI (SEQ ID NO: 136) (influenza), or GILGFVFTL SEQ ID NO: 119 (influenza), or KLWESPQEI (SEQ ID NO: 6) (measles), or FLPSDFFPSV (SEQ ID NO: 69) (HepB), or SLPRSRTPI (SEQ ID NO: 218) (chicken pox virus) or SAPLPSNRV (SEQ ID NO: 219) (chicken pox virus). A subset of each group of mice is separated and euthanized to characterize and ensure the establishment of pre-existing immunity to the childhood vaccine as described in Example 8.

Treatment and analysis of anti-tumor effects: Tumor-bearing mice are injected intraperitoneally with the chimeric VLPs, or naked VLPs (without a target peptide) (100 µg/mouse) weekly for 3 times. Non-treated mice serve as controls. Tumor growth is monitored by luminescence imaging Results: It is contemplated that tumor-bearing mice treated with the chimeric VLPs display therapeutic antitumor effects exceeding the effects of obtained for mice administered the naked VLP and the control mice. Specifically, it is comtemplated that the chimeric VLPs are able to redirect the CD8+ T cells specific for the T cell epitope of the target peptide to the tumor and inhibit the growth of the tumor and in some instances eliminate the tumor, while the control mice i.p. injected with the naked VLPs or receiving no VLPs at all, do not redirect the CD8+ T cells specific for the T cell epitopes of the chimeric VLPs. It is contemplated that the control mice i.p. injected with the naked VLPs or receiving no VLPs at all inhibit the growth of the tumor and eliminate the tumor far less than is achieved with chimeric VLPs with the target peptide.

Example 11. Design and Synthesis of Epitope-Conjugated VLPs

Figure 2:
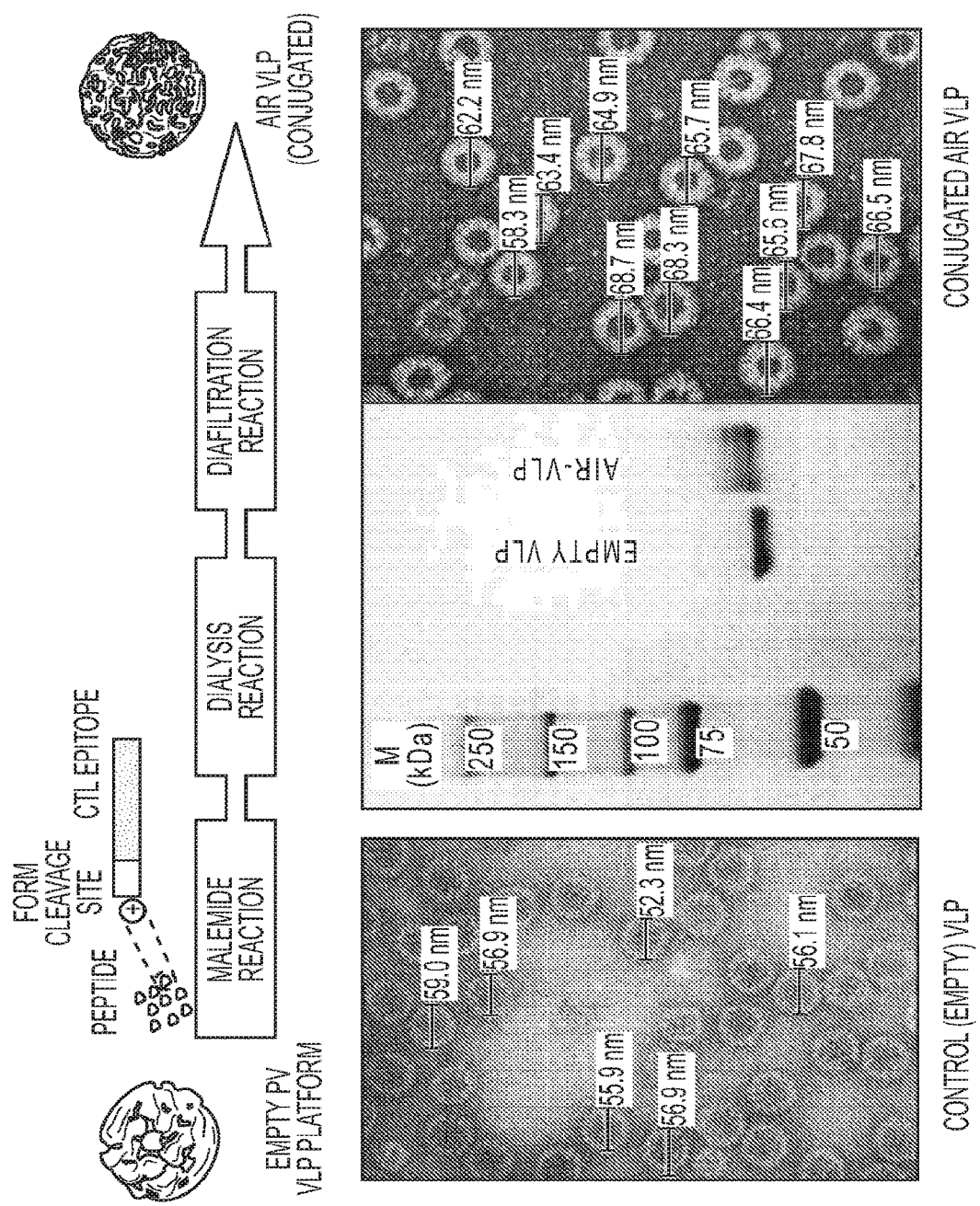
FIG. 2 depicts a TEM showing conjugated VLPs are slightly larger (60-70 nM) compared to the empty non-conjugated VLPs (50 nM).
Figure 3:
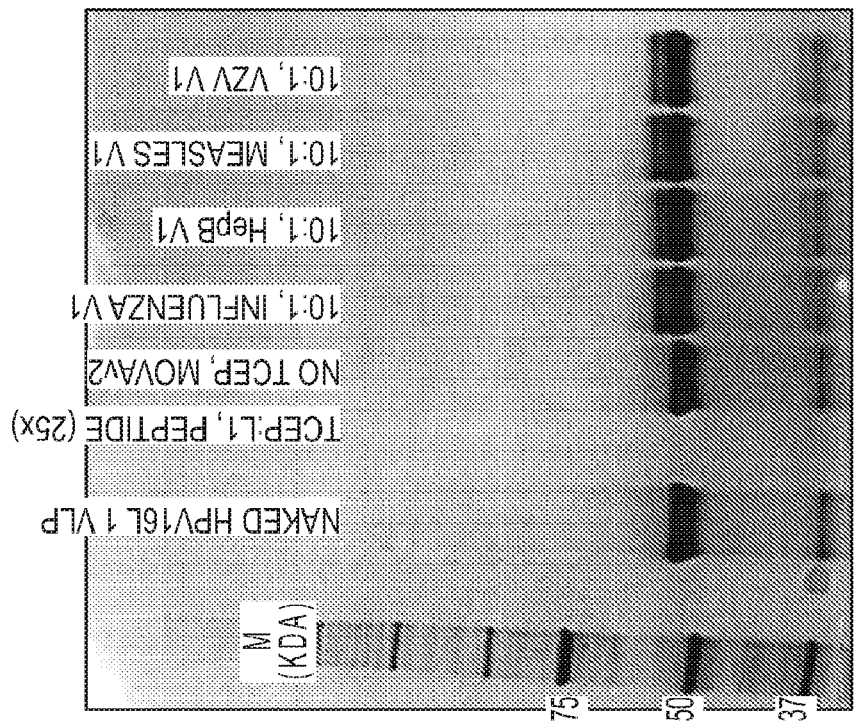
FIG. 3 depicts an SDS PAGE analysis of HPV 16 RG-1 VLPs (left panel) or wild type HPV 16 L1 VLPs (right panel) conjugated to epitopes derived from influenza, hepatitis B, measles and chicken pox viruses.
Figure 3:
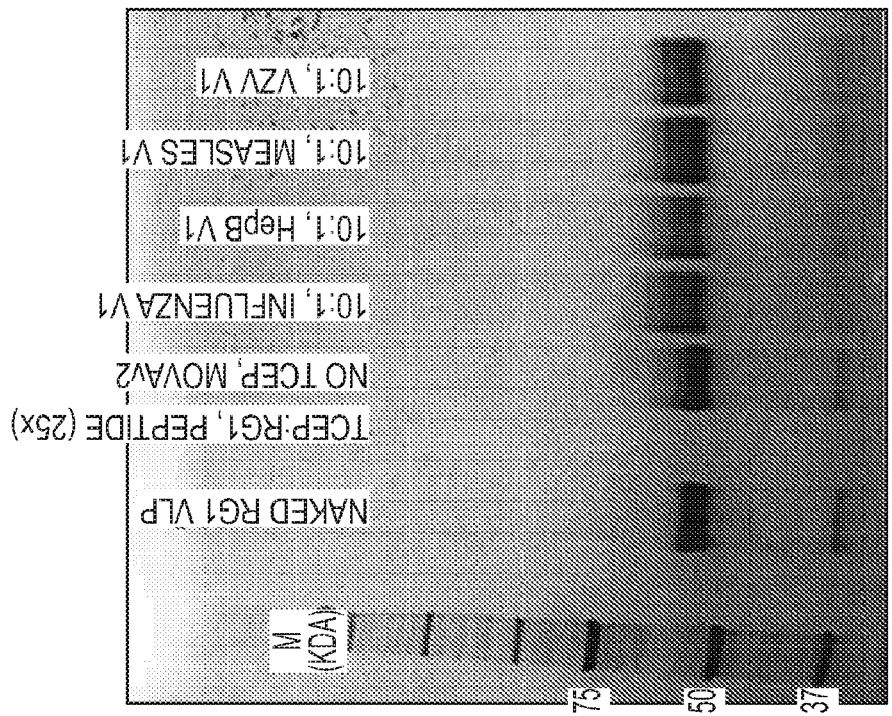

VLPs were produced in *Trichoplusia ni* (High Five™) cells essentially as described in Example 1. Briefly, VLPs were produced in *Trichoplusia ni* (High Five™) cells infected with a recombinant baculovirus expressing our chimeric papillomavirus L1 gene. The VLPs were purified using a 40% sucrose centrifugation, followed by another round of purification on a CsCl step gradient. The purity of the VLP preparation was determined by SDS-PAGE and morphology of particles were assessed by Transmission Electron Microscopy (TEM). Typical preparations were >90% pure and appeared as fully assembled capsid-like 50 nm particles by TEM (FIG. 2, left panel TEM). The target peptide (FMYSDFHFI (SEQ ID NO: 136) (influenza), or GILGFVFTL SEQ ID NO: 119 (influenza), or KLWESPQEI (SEQ ID NO: 6) (measles), or FLPSDFFPSV (SEQ ID NO: 69) (HepB), or SLPRSRTPI (SEQ ID NO: 218) (chicken pox virus) or SAPLPSNRV (SEQ ID NO: 219) (chicken pox virus)) were synthesized to >85% purity as polycationic (N-terminal malemide-Arg4RVKR-Epitope) 17mer peptides aka MAL-peptide. For conjugation, the empty unconjugated VLPs were subjected to reducing conditions with 50 mM sodium phosphate pH 6.5, 500 mM NaCl, 2 mM EDTA reaction buffer with TCEP (68 µM, final) (TCEP:VLP protein (mol:mol)=10:1). The mixture (volume=625 µl) was gently stirred every 15 mins for 1 hour at 21° C. After 1 hr reduction, MAL-peptide (170 µM, 625 µl) in reaction buffer was added into the TCEP-pretreated VLPs to a ratio of peptide:RG-1 protein (mol:mol)=25:1. The mixture was gently stirred at ~250 rpm at 21° C. for 1 hour before immediately proceeding to a purification process. Following conjugation, the composition comprising the conjugated VLPs were dialyzed in PBS pH 7, 500 mM NaCl, which was followed by a diafiltration step to remove excess peptide. The conjugated VLPs ("AIR VLPs") were analyzed by TEM. The TEM results of multiple AIR VLP batches were consistent showing slightly larger VLPs (60-70 nM) compared to the empty non-conjugated VLPs (50 nM). This result coupled with an SDS-PAGE analysis of the AIR-VLPs shows a high amount of peptide bound to the conjugated VLP. This conjugation process can be performed on different VLPs and was performed to form HPV 16 RG-1 VLPs and wildtype HPV16 VLPs conjugated to many different kinds of childhood vaccine epitopes as seen in FIG. 3. FIG. 3 is an SDS PAGE analysis of HPV 16 RG-1 VLPs (left panel) or wild type HPV 16 L1 VLPs (right panel) conjugated to epitopes dervived from influenza, hepatitis B, measles and chicken pox viruses.

Example 12. Tumor-Specific Binding by Different VLPs

To confirm the broad tumor binding ability of the chimeric VLPs described herein, we treated murine cervical cancer (TC-1), ovarian cancer (ID8), breast cancer (4T1), and melanoma cancer (B16) cell lines with 0.3 µg/ml of chimeric VLPs in vitro for 24 hours, stained the cells for the presence of tumor-bound VLPs, and then analyzed the stained cells by flow cytometry analysis.

Figure 4:
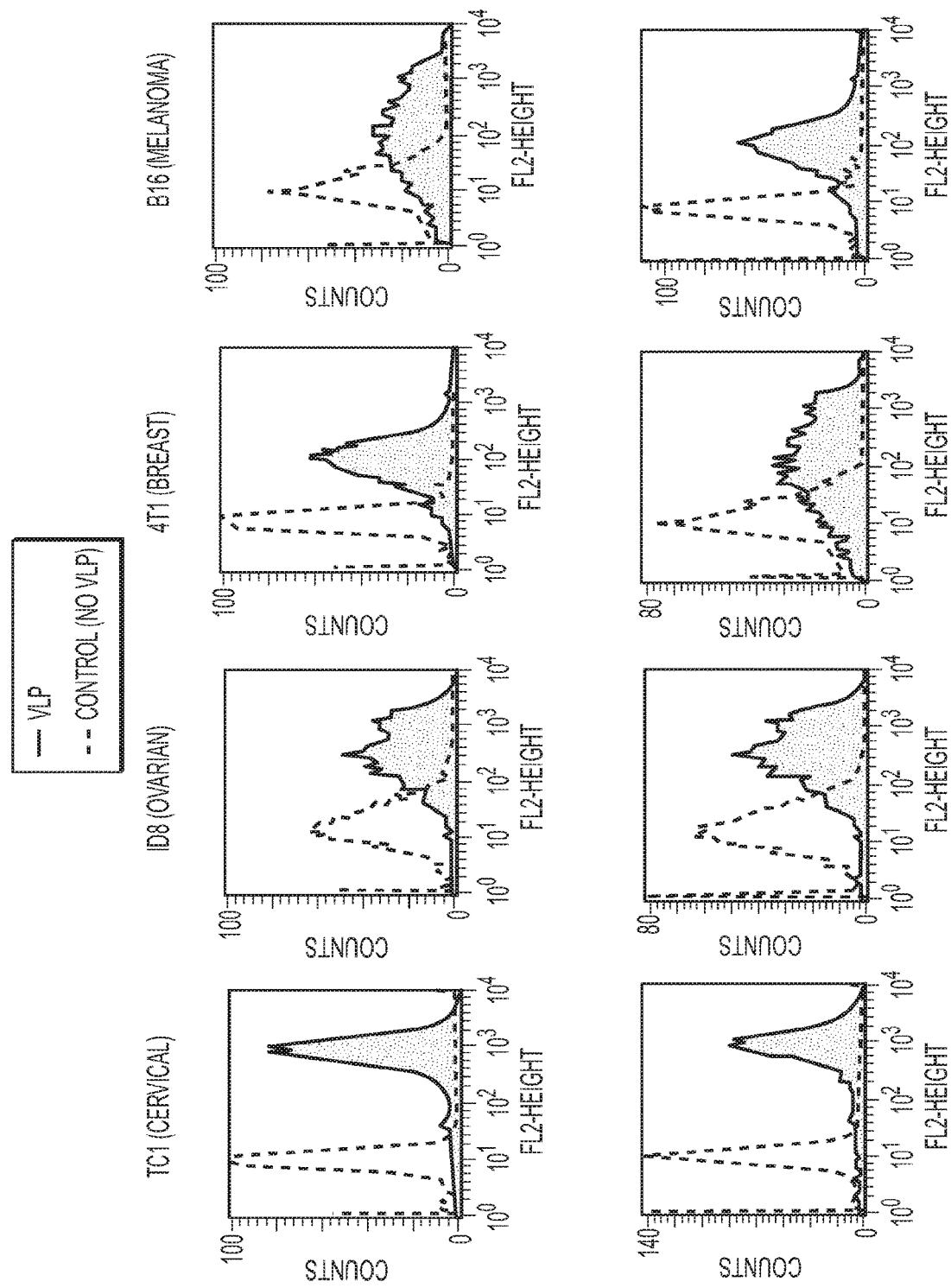
FIG. 4 depicts the results of a flow cytometry analysis of VLP binding to tumor cells. The shift in the cell population demonstrates VLP binding to all tested tumor cell lines. Top row shows the results of empty HPV16 RG-1 VLPs binding to the various tumor cell lines and the bottom row show the results of bovine papilloma virus (BPV) VLP having a peptide inserted recombinantly in one of the L1 loops).

FIG. 4 depicts a shift in the cell population demonstrating VLP binding to all tested tumor cell lines. FIG. 4, top row shows the results of empty HPV16 RG-1 VLPs binding to the various tumor cell lines and the bottom row show the results of bovine papilloma virus (BPV) VLP having a peptide inserted recombinantly in one of the L1 loops).

Figure 5:
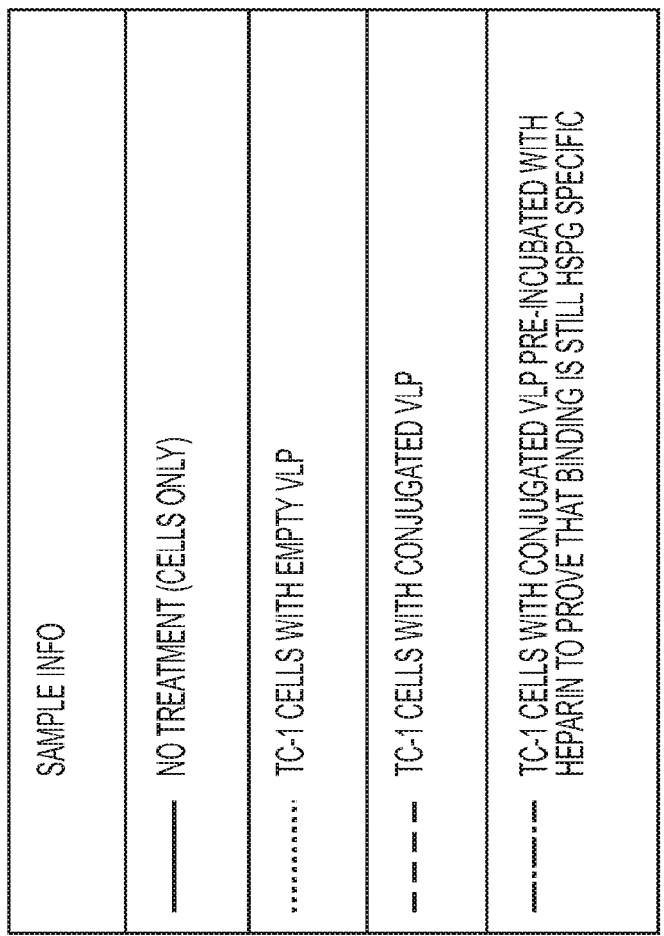
FIG. 5 depicts the results of a flow cytometry analysis of chimeric VLP comprising a target peptide. The results demonstrate the tumor binding ability of chimeric VLPs was not compromised by conjugating peptides on the VLP surface.
Figure 5:
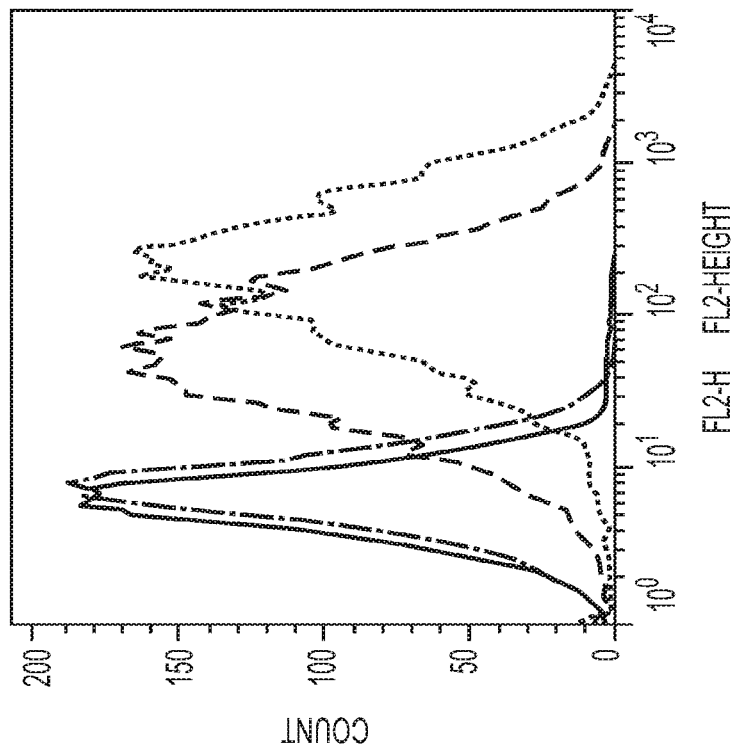

To demonstrate that the tumor binding ability of VLPs was not compromised by conjugating peptides on the VLP surface, we repeated the tumor binding studies described above with the conjugated VLPs. Consistent with results obtained with non-conjugated VLPs, the conjugated AIR-VLPs maintained their ability to bind to tumor cells (see FIG. 5).

Figure 6:
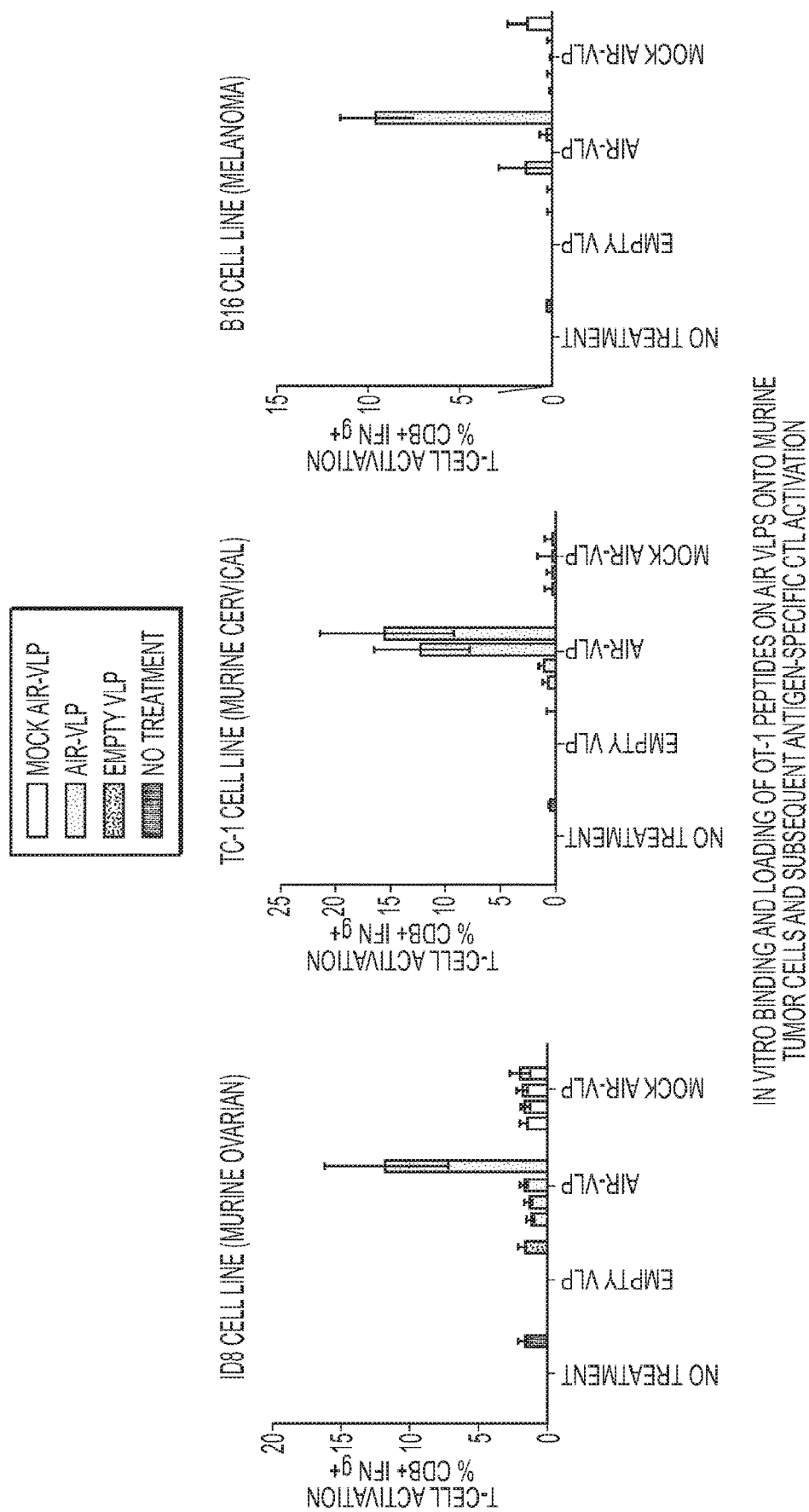
FIG. 6 demonstrates OT-1 specific CTL activation as assessed via surface CD8 and intracellular IFN-γ staining followed by flow cytometry analysis.

Example 13. Antigen-Specific Antitumor Immune Redirection by Conjugated VLP Leads to in Vitro Binding, Loading of CD8+ Epitope and Antitumor Killing by Coated Epitope-Specific CTLs To evaluate the feasibility of the conjugated VLPs described herein as an antitumor immune redirector, we first used the model antigen OVA (SIINFEKL, SEQ ID NO: 220). We conjugated this murine H2-KB restricted OVA epitope (SIINFEKL, SEQ ID NO: 220) with a furin cleavage site to a HPV 16 RG-1 VLP to generate a chimeric VLP (AIR-VLP). Tumor cells were then incubated with varying amounts (concentration 1.00 pM to 0.02 nM) of AIR-VLPs, or Control VLPs, such as empty, non-conjugated, VLPs or Mock AIR VLPs (a composition of non-conjugated VLPs and peptides not conjugated to the VLPs) in vitro for 24 hours and then incubated the treated tumor cells with $1\times10^5$ OT1-specific CTLs. OT-1 specific CTL activation was assessed via surface CD8 and intracellular IFN-γ staining followed by flow cytometry analysis. Significantly more CD8+ IFN-γ+ T cells were detected following incubation with AIR-VLPs treated tumor cells, indicated that the AIR-VLP treatment successfully coated non-OVA-expressing tumor cells with OVA peptides, resulting in subsequent recognition by and activation of OT-1-specific CTLs (see FIG. 6).

To evaluate the feasibility of the VLPs conjugated to a viral CD8+ epitope as an antitumor immune redirector, we conjugated the murine H2-DB restricted HPV16-E7 epitope (aa49-57) to a bovine papillomavirus VLP with a furin cleavage site to generate chimeric VLP-R-E7. We then incubated ID8 tumor cells with 0.3 µg/ml of empty non-conjugated VLPs or chimeric VLP-R-E7 in vitro for 24 hours and then incubated the treated tumor cells with $2 \times 10^5$ E7aa49-57-specific CTLs.

Figure 7:
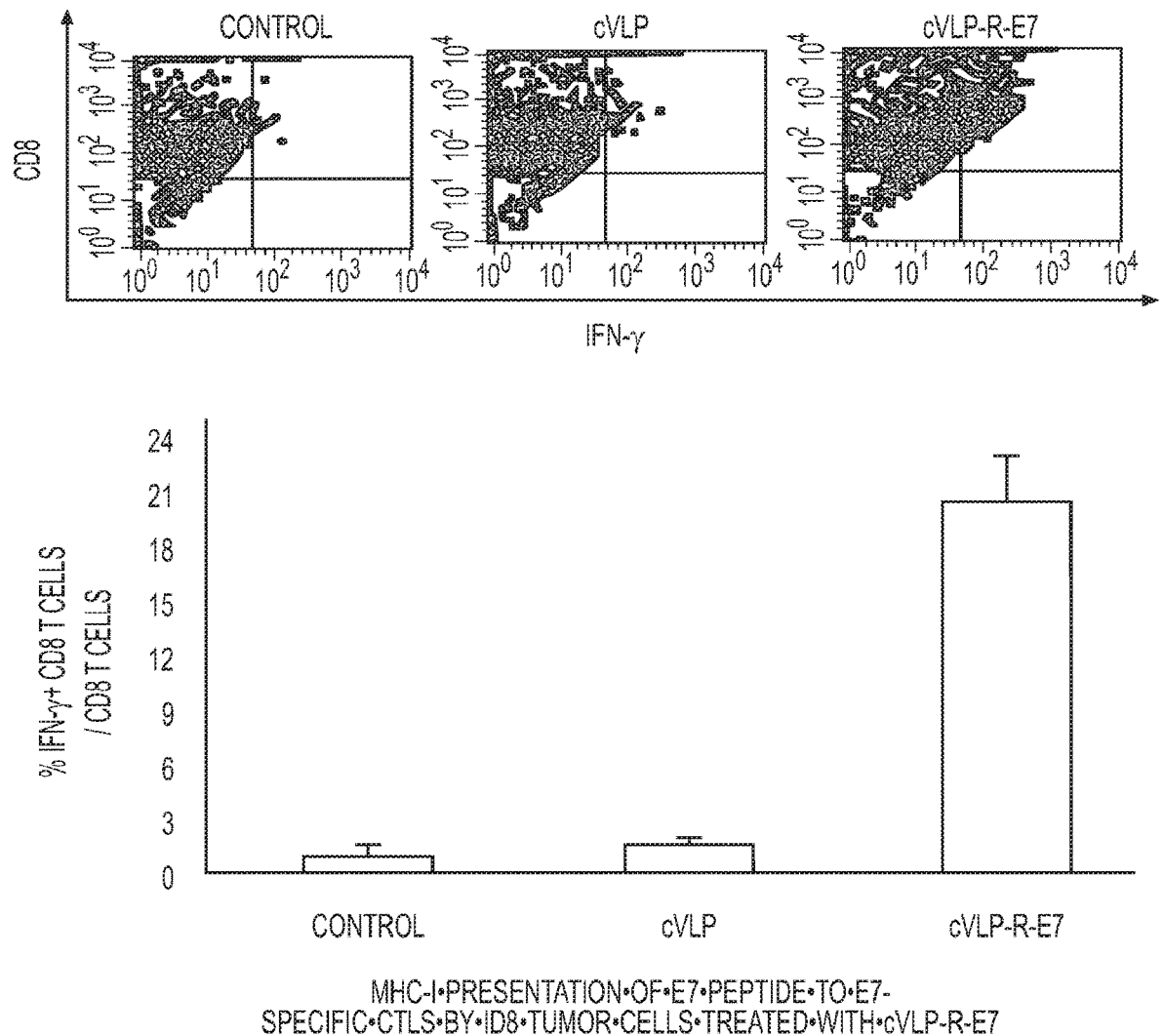
FIG. 7 demonstrates E7-specific CTL activation as assessed via surface CD8 and intracellular IFN-γ staining followed by flow cytometry analysis.

E7-specific CTL activation was assessed via surface CD8 and intracellular IFN-γ staining followed by flow cytometry analysis. Significantly more CD8+ IFN-γ+ T cells were detected following incubation with chimeric VLP-R-E7 treated ID8 tumor cells indicating that chimeric VLP-R-E7 treatment successfully coated non-E7-expressing ID8 tumor cells with E7 peptides, resulting in subsequent recognition by and activation of E7-specific CTLs (See FIG. 7).

Figure 8:
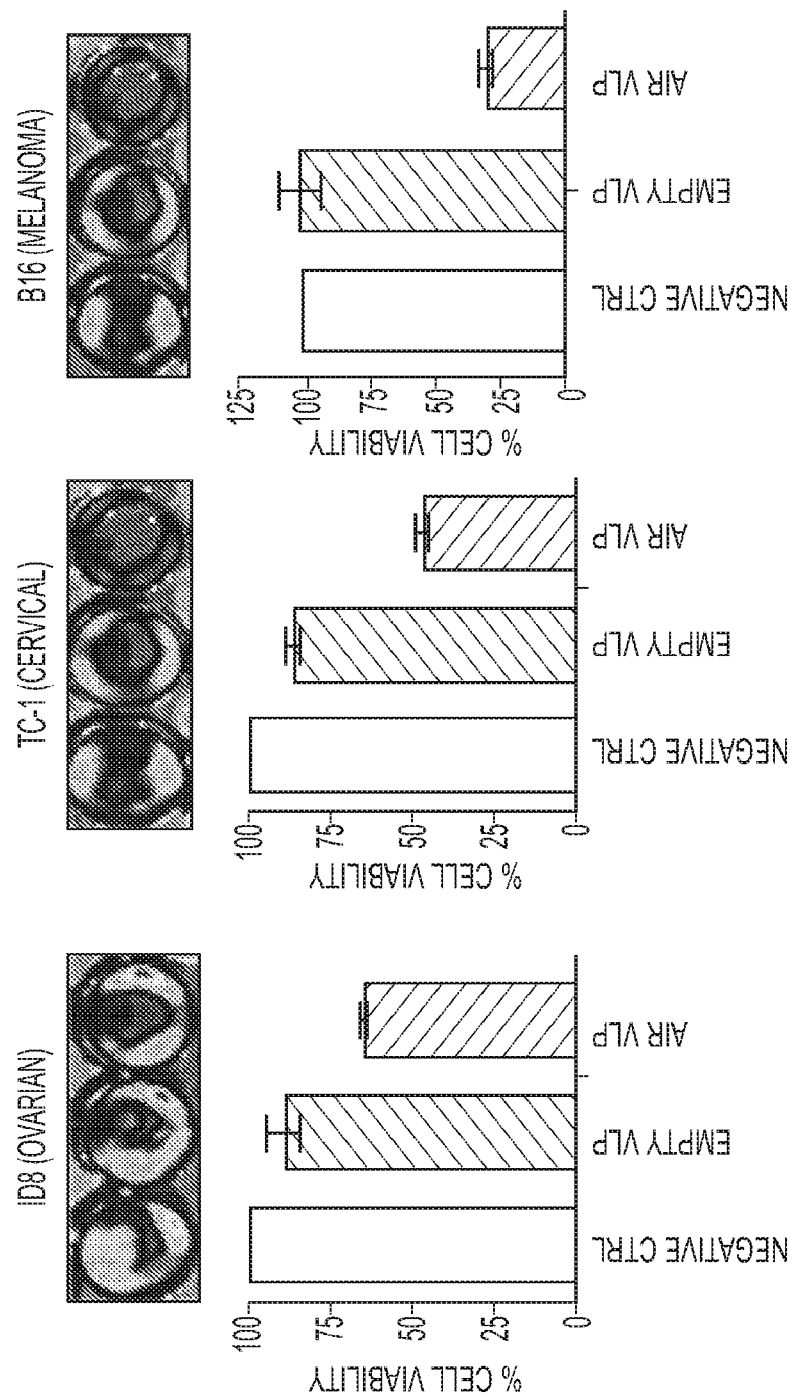
FIG. 8 depicts the results of bioluminescence imaging based on the luciferase expression by live ID8/luc cells. These cells typically are not recognized by OVA-specific CD8+ T-cells. The results demonstrate incubation with AIR-VLPs (chimeric VLP comprising a OVA target peptide), but not empty non-conjugated VLPs resulted in the tumor cells becoming recognized by OVA-specific CD8+ T cells. Incubation with the AIR-VLPs led to the greatest amount of tumor cell death mediated by OVA-specific CD8+ T cell killing, demonstrated by a significant decrease in luminescence activity.

To demonstrate that chimeric VLP-induced immune redirection can lead to cytotoxic killing of the coated tumor cells, we demonstrated that AIR-VLPs binding to the tumor cells resulted in CTL release which rendered the tumor cells more susceptible to killing by OVA-specific CD8+ T cells. As shown in FIG. 8, incubating AIR-VLPs, but not empty non-conjugated VLPs led to the greatest amount of tumor cell death mediated by OVA-specific CD8+ T cell killing, demonstrated by a significant decrease in luminescence activity (see FIG. 8).

Figure 9:
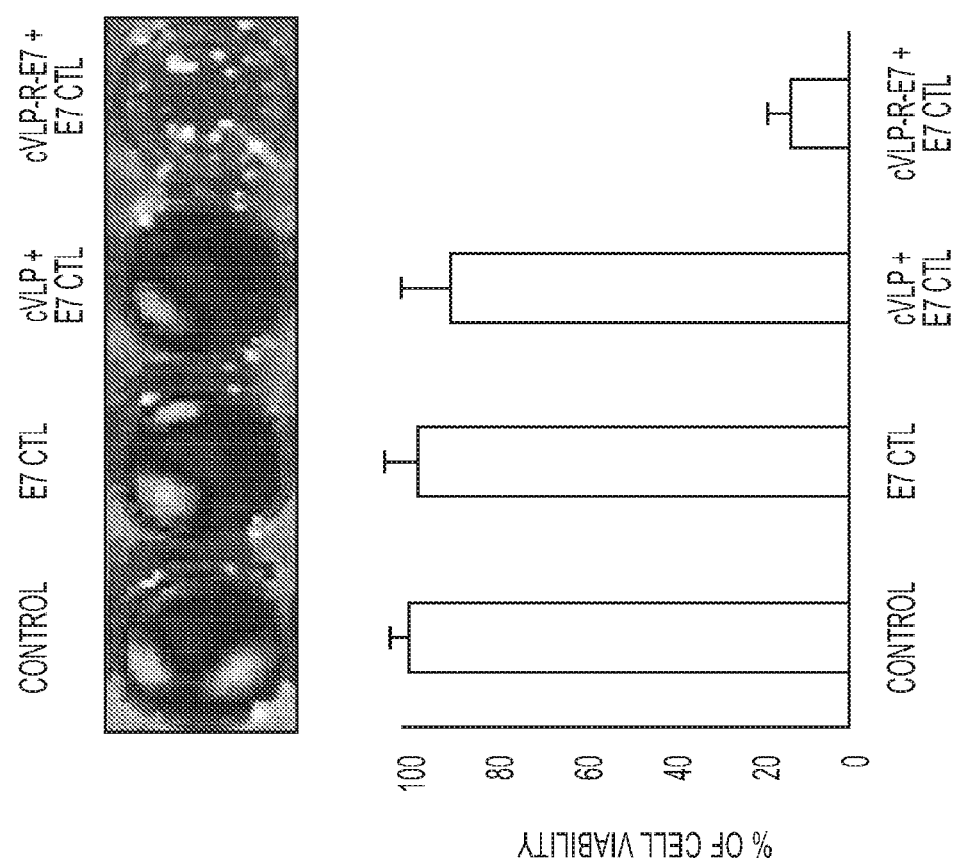
FIG. 9 depicts the results of bioluminescence imaging based on the luciferase expression by live ID8/luc cells. These cells typically are not recognized by E7aa49-57-specific CTLs. ID8/luc tumor cells were treated with 0.3 μg/ml of empty non-conjugated VLPs or chimeric VLP-R-E7 (bovine papillomavirus VLPs conjugated to the murine H2-DB restricted HPV16-E7 epitope (aa49-57), a tumor associated antigen) and then incubated E7aa49-57-specific CTLs. A significantly lower luciferase activity was observed for ID8 tumor cells treated with chimeric VLP-R-E7 and incubated with E7-specific CTLs, indicating a significant reduction in ID8 tumor cell viability following the treatment.

ID8/luc tumor cells were treated with 0.3 μg/ml of empty non-conjugated VLPs or chimeric VLP-R-E7 in vitro for 24 hours and then incubated the treated tumor cells with $2 \times 10^4$ E7aa49-57-specific CTLs. We then assessed tumor cell viability via bioluminescence imaging based on the luciferase expression by live ID8/luc cells. A significantly lower luciferase activity was observed for ID8 tumor cells treated with chimeric VLP-R-E7 and incubated with E7-specific CTLs, indicating a significant reduction in ID8 tumor cell viability following the treatment. Together, this data demonstrates the ability of chimeric VLPs conjugated with a target peptide to coat tumor cells and load surface MHC-I of the tumor cells with the target peptide, resulting in subsequent killing of coated tumor cells by activated CTLs (see FIG. 9).

TABLE I

| Epitope Sequence | SEQ ID NO | Virus Type | MHC allele | Viral Protien | Reference (PMID/ Pat. no.) | Species |
| --- | --- | --- | --- | --- | --- | --- |
| SMLNSQAIDNLRA | 1 | Measles | A*02:01 | Fusion Protien | 26579122 | Human |
| LMIDRPYVL1 | 2 | Measles | A*02:01 | Hemaggutinin | 26579122 | Human |
| VIINDDQGLFKV | 3 | Measles | A*02:01 | Matrix | 26579122 | Human |
| KIIDNTEQL | 4 | Measles | A*02:01 | Matrix | 26579122 | Human |
| RLSDNGYYTV | 5 | Measles | A*02:01 | Matrix | 26579122 | Human |
| KLWESPQEI | 6 | Measles | A*02:01 | C-protein | 26579122 | Human |
| KLIDGFFPA | 7 | Measles | A*02:01 | polymerase | 26579122 | Human |
| SMYRVFEV | 8 | Measles | A*02:01 | Hemaggutinin | 26579122 | Human |
| KVSPYLFTV | 9 | Measles | A*02:01 | Hemaggutinin | 26579122 | Human |
| SLMPEETLHQV | 10 | Measles | A*02:01 | polymerase | 26579122 | Human |
| RQAGQEMILAV | 11 | Measles | A*02:01/B*15:01 | Fusion Protien | 26579122 | Human |
| GSAPISMGFR | 12 | Measles | A*03:01 | PVC gene | 26579122 | Human |
| GMYGGTYLVEK2 | 13 | Measles | A*03:01 | Hemaggutinin | 26579122 | Human |
| AVRDLERAMTTLK | 14 | Measles | A*03:01 | C-protein | 26579122 | Human |
| YVYDHSGEAVK | 15 | Measles | A*03:01/A*11:01 | PVC gene | 26579122 | Human |
| AIYTAEIHK | 16 | Measles | A*03:01/A*11:01 | Hemaggutinin | 26579122 | Human |
| GPRQAQVSF(L) | 17 | Measles | B*07:02 | Nucleocapsid | 26579122 | Human |
| YPALGLHEF | 18 | Measles | B*07:02/B*35:01 | Nucleocapsid | 26579122 | Human |
| RPGLKPDL | 19 | Measles | B*07:02 | Fusion Protien | 26579122 | Human |
| IPYQGSGKGVSF | 20 | Measles | B*07:02/B*35:01 | Hemaggutinin | 26579122 | Human |
| KPNLSSKRSEL | 21 | Measles | B*07:02 | Hemaggutinin | 26579122 | Human |
| RPIYGLEV | 22 | Measles | B*07:03 | polymerase | 26579122 | Human |
| DALLRLQAM | 23 | Measles | B*08:01 | Nucleocapsid | 26579122 | Human |
| FPKLGKTL | 24 | Measles | B*08:01 | PVC gene | 26579122 | Human |
| LLKEATEL | 25 | Measles | B*08:01 | Matrix | 26579122 | Human |
| IPPMKNLAL | 26 | Measles | B*08:01 | Hemaggutinin | 26579122 | Human |
| DIKEKVINL | 27 | Measles | B*08:01 | polymerase | 26579122 | Human |

TABLE I-continued

| Epitope Sequence | SEQ ID NO | Virus Type | MHC allele | Viral Protien | Reference (PMID/ Pat. no.) | Species |
|---|---|---|---|---|---|---|
| HILAKSTAL | 28 | Measles | B*08:01 | polymerase | 26579122 | Human |
| YLKDKALA | 29 | Measles | B*08:01 | polymerase | 26579122 | Human |
| GLNEKLVFY | 30 | Measles | B*15:01 | Matrix | 26579122 | Human |
| RITHVDTESY | 31 | Measles | B*15:01 | Fusion Protien | 26579122 | Human |
| LLKKGNSLY | 32 | Measles | B*15:01 | polymerase | 26579122 | Human |
| SKESQHVY | 33 | Measles | B*15:01 | polymerase | 26579122 | Human |
| AQRLNEIY | 34 | Measles | B*15:01 | polymerase | 26579122 | Human |
| SQQGMFHAY | 35 | Measles | B*15:01 | polymerase | 26579122 | Human |
| SMIDLVTKF | 36 | Measles | B*15:01 | polymerase | 26579122 | Human |
| IVSSHFFVY6 | 37 | Measles | B*15:01 | polymerase | 26579122 | Human |
| EPIGSLAIEEAM | 38 | Measles | B*35:01 | PVC gene | 26579122 | Human |
| EPIRDALNAM | 39 | Measles | B*35:01 | Fusion Protien | 26579122 | Human |
| APVFHMTNY | 40 | Measles | B*35:01 | Hemaggutinin | 26579122 | Human |
| SAVRIATVY | 41 | Measles | B*35:01 | polymerase | 26579122 | Human |
| MPEETLHQVM | 42 | Measles | B*35:01 | polymerase | 26579122 | Human |
| LPAPIGGMNY | 43 | Measles | B*35:01 | polymerase | 26579122 | Human |
| AEGGEIHEL | 44 | Measles | B*40:01 | PVC gene | 26579122 | Human |
| AEVDGDVKL | 45 | Measles | B*40:01 | Hemaggutinin | 26579122 | Human |
| LETRTTNQFL | 46 | Measles | B*40:01 | Hemaggutinin | 26579122 | Human |
| KESQHVYYL | 47 | Measles | B*40:01 | polymerase | 26579122 | Human |
| YESGVRIASL | 48 | Measles | B*40:01 | polymerase | 26579122 | Human |
| QEISRHQALGY | 49 | Measles | B*44:02 | PVC gene | 26579122 | Human |
| KEIKETGRLF | 50 | Measles | B*44:02 | polymerase | 26579122 | Human |
| AENLISNGIGKY | 51 | Measles | B*44:02 | polymerase | 26579122 | Human |
| AVRDLERAM | 52 | Measles | C*03:04 | PVC gene | 26579122 | Human |
| FRSVNAVAF | 53 | Measles | C*07:02 | Matrix | 26579122 | Human |
| ARVPHAYSL | 54 | Measles | C*07:02 | polymerase | 26579122 | Human |
| TDTPIVYNDRNL(LD) | 55 | Measles | Unknown | Nucleocapsid | 26579122 | Human |
| KKQINRQN | 56 | Measles | Unknown | PVC gene | 26579122 | Human |
| DTGVDTRIW | 57 | Measles | Unknown | PVC gene | 26579122 | Human |
| DQGLFKVL | 58 | Measles | Unknown | Matrix | 26579122 | Human |
| GKIIDNTEQL | 59 | Measles | Unknown | Matrix | 26579122 | Human |
| GRLVPQVRVID | 60 | Measles | Unknown | Matrix | 26579122 | Human |
| GPPISLERLDVGTN | 61 | Measles | Unknown | Fusion Protien | 26579122 | Human |
| APVFHMTNYLEQPVS(N) | 62 | Measles | Unknown | Hemaggutinin | 26579122 | Human |
| PTTIRGQFS | 63 | Measles | Unknown | Hemaggutinin | 26579122 | Human |
| HYREVNLVY | 64 | Measles | Unknown | polymerase | 26579122 | Human |
| (K)KVDTNFIY(QQ) | 65 | Measles | Unknown | polymerase | 26579122 | Human |

TABLE I-continued

| Epitope Sequence | SEQ ID NO | Virus Type | MHC allele | Viral Protien | Reference (PMID/ Pat. no.) | Species |
|---|---|---|---|---|---|---|
| LSEIKGVIVHRLEGV | 66 | Measles | H-2K | Fusion Protien | 9129158 | mice |
| LDRLVRLIG | 67 | Measles | H-2K | Nucleocapsid | 9129158 | mice |
| RRYPDAVYL | 68 | Measles | HLA-B27/ HLA-A2.1/Kb | Fusion Protien | 10998329 | HLA-A2.1Kb transgenic mice/ humans |
| FLPSDFFPSV | 69 | Hep B | | Core protein | 10751335 | Human |
| FLLTRILTI | 70 | Hep B | | ENV | 10751335 | Human |
| WLSLLVPFV | 71 | Hep B | | ENV | 10751335 | Human |
| GLSRYVARL | 72 | Hep B | | POL | 10751335 | Human |
| FLLSLGIHL | 73 | Hep B | | POL | 10751335 | Human |
| MDIDPYKEFGATVELLSFLP | 74 | Hep B | | Nucleocapsid | US4882145A | Human |
| RDLLDTASALYREALESPEHCSPHH | 75 | Hep B | | Nucleocapsid | US4882145A | Human |
| TWVGVNLEDPASRDLVVSYVNTNMG | 76 | Hep B | | Nucleocapsid | US4882145A | Human |
| VVSYVNTNMGLKFRQL | 77 | Hep B | | Nucleocapsid | US4882145A | Human |
| VVSYVNTNMGLK | 78 | Hep B | | Nucleocapsid | US4882145A | Human |
| LLWFHISCLTFGRETVIEYLV | 79 | Hep B | | Nucleocapsid | US4882145A | Human |
| LLWFHISCLTF | 80 | Hep B | | Nucleocapsid | US4882145A | Human |
| VSFGVWIRTPPA, | 81 | Hep B | | Nucleocapsid | US4882145A | Human |
| VSFGVWIRTPPAYRPPNAPIL | 82 | Hep B | | Nucleocapsid | US4882145A | Human |
| PPAYRPPNAPIL | 83 | Hep B | | Nucleocapsid | US4882145A | Human |
| WIRTPPAYRPPN | 84 | Hep B | | Nucleocapsid | US4882145A | Human |
| LLAQFTSAI | 85 | Hep B | | POL | US20030099634 | Human |
| ALMPLYAC | 86 | Hep B | | POL | US20030099634 | Human |
| KLHLYSHPI | 87 | Hep B | | POL | US20030099634 | Human |
| YLHTLWKAGI | 88 | Hep B | | POL | US20030099634 | Human |
| YLHTLWKAGV | 89 | Hep B | | POL | US20030099634 | Human |
| LLVPFVQWFV | 90 | Hep B | | ENV | US20030099634 | Human |
| ILLLCLIFLL | 91 | Hep B | | ENV | US20030099634 | Human |
| VLLDYQGML | 92 | Hep B | | ENV | US20030099634 | Human |
| LLPIFFCLWV | 93 | Hep B | | ENV | US20030099634 | Human |
| VLQAGFFLL | 94 | Hep B | | ENV | US20030099634 | Human |
| PLLPIFFCL | 95 | Hep B | | ENV | US20030099634 | Human |
| ILSTLPETTV | 96 | Hep B | | Nucleocapsid | US20030099634 | Human |
| NCTCIPIPSSYAFGKFLTGY | 97 | Hep B | | ENV | WO1993003764A1 | Human |
| ASARFSYLSLLVPFVGYFVG | 98 | Hep B | | ENV | WO1993003764A1 | Human |
| LSPTVYLSVIYMMYYYGPSL | 99 | Hep B | | ENV | WO1993003764A1 | Human |
| TNMGLKFRLLYFHISCLYF | 100 | Hep B | | Core protein | WO1993003764A1 | Human |

TABLE I-continued

| Epitope Sequence | SEQ ID NO | Virus Type | MHC allele | Viral Protien | Reference (PMID/ Pat. no.) | Species |
|---|---|---|---|---|---|---|
| AAFEDLRVLSFIRG | 101 | Influenza A | HLA-B37 | NP | | Human |
| AGFIENGWEGMVDGWYGFRH QNSEGTGQAADLKS | 102 | Influenza A | | HA | | HUMAN |
| AIMDKNIIL | 103 | | HLA-A*0201; HLA-A*020101; HLA-A2.1 | NS1 | | HUMAN; MOUSE |
| ASCMGLIY | 104 | Influenza A | HLA-B*35; HLA-B*3501 | M1 | | HUMAN |
| ASGRVTVSTKRSQQTV | 105 | Influenza A | | HA | | HUMAN |
| ASQGTKRSYEQMETDGERQNA TE | 106 | Influenza A | | NP | | HUMAN |
| ATGMRNVPEKQTRGIFGAIAGF IENGWEGMVD | 107 | Influenza A | | HA | | HUMAN |
| CTELKLSDY | 108 | Influenza A | HLA-A*0101; HLAA1 | NP | | HUMAN |
| CVNGSCFTV | 109 | Influenza A | HLA-A*0201 | NA | | HUMAN; MOUSE |
| CYPYDVPDYASLRSLV | 110 | Influenza A | | | | |
| CYPYDVPDYASLRSLVASS | 111 | Influenza A | | | | |
| CYPYDVPDYASLRSLVASSGTLE FINEDFNWT | 112 | Influenza A | | HA | | HUMAN |
| DPRMCSLMQGSTLP | 113 | Influenza A | | NP | | HUMAN |
| DYASLRSLVASSGTLEFINEGFN WTGVTQNGGSSAC | 114 | Influenza A | | HA | | HUMAN |
| EDLTFLARSAL | 115 | Influenza A | | NP | | HUMAN |
| ELRSRYWAI | 116 | Influenza A | HLA-B8 | NP | | HUMAN |
| ENQHTIDLTDSEMNKLFEKTRK QLRENAEDMGNGCF | 117 | Influenza A | | HA | | HUMAN |
| FEDLRVLS | 118 | Influenza A | HLA-B37 | NP | | HUMAN |
| GILGFVFTL | 119 | Influenza A | HLA-A*0201; HLA-A*020101; HLA-A*0203; HLA-A*0206; HLA-A2; HLA-A2.1 | M1 | U.S. 15/421,758 | HUMAN; MOUSE |
| GILGFVFTLT | 120 | Influenza A | HLA-A*0201; HLA-A2 | M1 | | HUMAN; MOUSE |
| GILGFVFTLTV | 121 | Influenza A | HLA-A2; HLA-AW69 | | | HUMAN |
| GKNTDLEVLMEWLKTRPILS | 122 | Influenza A | HLA-A2 | M1 | | HUMAN |
| HHPSTDRDQTSLYVRASGRVTV STKRSQQTVTPNI | 123 | Influenza A | | HA | | HUMAN |
| KGILGFVFTLTV | 124 | Influenza A | HLA-A*02; HLA-A*0201; HLA-A2 | M1 | | HUMAN; MOUSE |
| KLSTRGVQIASNEN | 125 | Influenza A | | NP | | HUMAN |
| LKGKFQTAAQRAMMDQVRES | 126 | Influenza A | | NP | | HUMAN |
| LPRRSGAAGAAVKG | 127 | Influenza A | | NP | | HUMAN |
| LRVLSFIRGTKVSPRGKLSTRG | 128 | Influenza A | | NP | | HUMAN |

TABLE I-continued

| Epitope Sequence | SEQ ID NO | Virus Type | MHC allele | Viral Protien | Reference (PMID/ Pat. no.) | Species |
|---|---|---|---|---|---|---|
| LTKGILGFVFTLTVPSERG | 129 | Influenza A | HLA-A2.1 | M1 | | HUMAN |
| PSFDMSNEGSYFFGDNAEEYDN | 130 | Influenza A | | NP | | HUMAN |
| RGLQRRRFVQNALNGNG | 131 | Influenza A | HLA-A2 | M1 | | HUMAN |
| RRSGAAGAAVK | 132 | Influenza A | HLA-B27 | NP | | HUMAN |
| RYWAIRTR | 133 | Influenza A | HLA-B*2705 | NP | | HUMAN |
| SRYWAIRTR | 134 | Influenza A | HLA-B*08;HLAB*2703; HLAB*2705; HLAB*27052/KB; HLAB27 | NP | | HUMAN; MOUSE |
| VSDGGPNLY | 135 | Influenza A | HLA-A*0101; HLAA1; MAMU-A*02 | PB1 | | HUMAN |
| FMYSDFHFI | 136 | Influenza A | HLA-A*0201; HLA-A*0202; HLA-A*0206 | PA | | HUMAN |
| ILGFVFTLTV | 137 | Influenza A | HLA-A*0201; HLAA*020101; HLAA*0203 | M1 | | HUMAN; MOUSE |
| NMLSTVLGV | 138 | Influenza A | HLA-A*0201; HLAA*0206; HLAA*6802 | PB1 | | HUMAN |
| RMVLASTTAK | 139 | Influenza A | HLA-A*0301; HLAA*11; HLA-A11 | M1 | | HUMAN |
| SIIPSGPLK | 140 | Influenza A | HLA-A*3101; HLAA11 | M1 | | HUMAN |
| SLENFRAYV | 141 | Influenza A | HLA-A*0201; HLAA*0203; HLAA*6802 | PA | | HUMAN |
| LTKGILGFVFTLTVPSERGL | 142 | Influenza A | HLA-A2 | M1 | 3029268 | HUMAN |
| GLCTLVAML | 143 | Epstein Barr Virus | HLA-A2 | | 9143694 | HUMAN |
| ARNLVPMVATVQGQ | 144 | CMV | HLA-A2 | pp65 | | HUMAN |
| RKTPRVTGGGAMAGA | 145 | CMV | HLA-B7 | pp65 | 8892876 | HUMAN |
| QEFFWDANDIYRIFA | 146 | CMV | HAL-B8 | pp65 | 8892876 | HUMAN |
| ARNLVPMVATVQGQN | 147 | CMV | HLA-A2 | pp65 | 8892876 | HUMAN |
| YYTSAFVFPTKD | 148 | CMV | HLA-B35 | pp65 | 8892876 | HUMAN |
| VFPTKDVALRH | 149 | CMV | HLA-B35 | pp65 | 8892876 | HUMAN |
| DDVWTSGSDSDEELV) | 150 | CMV | HLA-B35 | pp65 | 8892876 | HUMAN |
| NLVPMVATV | 151 | CMV | HLA-A2 | pp65 | | HUMAN |
| VAIIEVDNEQPTTRAQKL | 152 | Polio | | VP1 | 7679749 | |
| TRAQKLFAMWRITYKDTV | 153 | Polio | | VP1 | 7679749 | |
| GACVAIIEVDNEQPTTRAQKLFA MWRITYKDTVQLRRKL | 154 | Polio | ANY 9MER WITHIN THIS SEQUENCE | VP1 | 7679749 | |

TABLE 2

EBV-encoded CTL Epitopes*

| EBV antigen | Epitope co-ordinates | Epitope sequence | HLA restriction Class I | SEQ ID NO | EBV type specificity |
|---|---|---|---|---|---|
| *Latent cycle antigens* | | | | | |
| EBNA1 | 407-417 | HPVGEADYFEY | B35.01 | 155 | nt |
| EBNA2 | 42-51 | DTPLIPLTIF | ?A2/B51 | 156 | Type 1 |
| EBNA3A | 158-166 | QAKWRLQTL | B8 | 157 | Type 1 |
|  | 176-184 | AYSSWMYSY | A30.02 | 158 | Type 1 & 2 |
|  | 246-253 | RYSIFFDY | A24 | 159 | Type 1 |
|  | 325-333 | FLRGRAYGL | B8 | 160 | Type 1 |
|  | 379-387 | RPPIFIRRL | B7 | 161 | Type 1 |
|  | 406-414 | LEKARGSTY | B62 | 162 | Type 1 |
|  | 450-458 | HLAAQGMAY | ? | 163 | Type 1 |
|  | 458-466 | YPLHEQHGM | B35.01 | 164 | Type 1 |
|  | 491-499 | VFSDGRVAC | A29 | 165 | Type 1 |
|  | 502-510 | VPAPAGPIV | B7 | 166 | Type 1 |
|  | 596-604 | SVRDRLARL | A2 | 167 | Type 1 & 2 |
|  | 603-611 | RLRAEAQVK | A3 | 168 | Type 1 & 2 |
| EBNA3B | 101-115 | NPTQAPVIQLVHAVY | A11 | 169 | Type 1 |
|  | 149-157 | HRCQAIRKK | B27.05 | 170 | nt |
|  | 217-225 | TYSAGIVQI | A24.02 | 171 | Type 1 |
|  | 244-254 | RRARSLSAERY | B27.02 | 172 | Type 1 |
|  | 399-408 | AVFDRKSDAK | A11 | 173 | Type 1 |
|  | 416-424 | IVTDFSVIK | A11 | 174 | Type 1 |
|  | 481-495 | LPGPQVTAVLLHEES | A11 | 175 | Type 1 |
|  | 488-496 | AVLLHEESM | B35.01 | 176 | Type 1 |
|  | 551-563 | DEPASTEPVHDQLL | A11 | 177 | Type 1 |
|  | 657-666 | VEITPYKPTW | B44 | 178 | Type 1 |
|  | 831-839 | GQGGSPTAM | B62 | 179 | Type 1 |
| EBNA3C | 163-171 | EGGVGWRHW | B44.03 | 180 | Type 1 & 2 |
|  | 213-222 | QNGALAINTF | B62 | 181 | Type 2 |
|  | 249-258 | LRGKWQRRYR | B27.05 | 182 | Type 1 |
|  | 258-266 | RRIYDLIEL | B27.02/.04/.05 | 183 | Type 1 |
|  | 271-278 | HHIWQNLL | B39 | 184 | Type 1 & 2 |
|  | 281-290 | EENLLDFVRF | B44.02 | 185 | Type 1 & 2 |
|  | 284-293 | LLDFVRFMGV | A2.01 | 186 | Type 1 & 2 |
|  | 335-343 | KEHVIQNAF | B44.02 | 187 | Type 1 |
|  | 343-351 | FRKAQIQGL | B27.05 | 188 | Type 1 |
|  | 881-889 | QPRAPIRPI | B7 | 189 | Type 1 & 2 |
| EBNA-LP | | Occasional responses identified, no epitopes defined | | | |
| LMP1 | | Occasional responses identified, no epitopes defined | | | |
| LMP2 | 131-139 | PYLFWLAAI | A23 | 190 | Type 1 & 2 |
|  | 200-208 | IEDPPFNSL | B60 | 191 | Type 1 & 2 |
|  | 236-244 | RRRWRRLTV | B27.04 | 192 | Type 1 & 2 |
|  | 329-337 | LLWTLVVLL | A2.01 | 193 | Type 1 & 2 |
|  | 340-350 | SSCSSCPLSKI | A11 | 194 | Type 1 & 2 |
|  | 419-427 | TYGPVFMCL | A24 | 195 | Type 1 & 2 |
|  | 426-434 | CLGGLLTMV | A2.01 | 196 | Type 1 & 2 |
|  | 442-451 | VMSNTLLSAW | A25 | 197 | Type 1 & 2 |
|  | 453-461 | LTAGFLIFL | A2.06 | 198 | Type 1 & 2 |
| BZLF1 | 190-197 | RAKFKQLL | B8 | 199 | nt |
|  | 186-201 | RKCCRAKFKQLLQHYR | C6 | 200 | nt |
| BMLF1 | 265-273 | KDTWLDARM | ? | 201 | nt |
|  | 280-288 | GLCTLVAML | A2.01 | 143 | nt |
|  | 397-405 | DEVEFLGHY | B18 | 202 | nt |
| BMRF1 | 86-100 | FRNLAYGRTCVLGKE | C3 | 203 | nt |
|  | 268-276 | YRSGIIAVV | C6 | 204 | nt |

*Source: Rickson and Moss *Annu. Rev. Immunol.* (1997) 15: 405-31 incorporated herein in its entirety by reference.

HPV16 (114K) L1 Protein Sequence
SEQ ID NO: 205

Met Ser Leu Trp Leu Pro Ser Glu Ala Thr Val Tyr Leu Pro Pro Val
1               5                   10                  15

Pro Val Ser Lys Val Val Ser Thr Asp Glu Tyr Val Ala Arg Thr Asn
            20                  25                  30

Ile Tyr Tyr His Ala Gly Thr Ser Arg Leu Leu Ala Val Gly His Pro
        35                  40                  45

Tyr Phe Pro Ile Lys Lys Pro Asn Asn Asn Lys Ile Leu Val Pro Lys
    50                  55                  60

Val Ser Gly Leu Gln Tyr Arg Val Phe Arg Ile His Leu Pro Asp Pro
65              70                  75                  80

Asn Lys Phe Gly Phe Pro Asp Thr Ser Phe Tyr Asn Pro Asp Thr Gln
                85                  90                  95

Arg Leu Val Trp Ala Cys Val Gly Val Glu Val Gly Arg Gly Gln Pro
                100                 105                 110

Leu Gly Val Gly Ile Ser Gly His Pro Leu Leu Asn Lys Leu Asp Asp
            115                 120                 125

Thr Glu Asn Ala Ser Ala Tyr Ala Ala Asn Ala Gly Val Asp Asn Arg
    130                 135                 140

Glu Cys Ile Ser Met Asp Tyr Lys Gln Thr Gln Leu Cys Leu Ile Gly
145                 150                 155                 160

Cys Lys Pro Pro Ile Gly Glu His Trp Gly Lys Gly Ser Pro Cys Thr
                165                 170                 175

Asn Val Ala Val Asn Pro Gly Asp Cys Pro Pro Leu Glu Leu Ile Asn
            180                 185                 190

Thr Val Ile Gln Asp Gly Asp Met Val Asp Thr Gly Phe Gly Ala Met
        195                 200                 205

Asp Phe Thr Thr Leu Gln Ala Asn Lys Ser Glu Val Pro Leu Asp Ile
    210                 215                 220

Cys Thr Ser Ile Cys Lys Tyr Pro Asp Tyr Ile Lys Met Val Ser Glu
225                 230                 235                 240

Pro Tyr Gly Asp Ser Leu Phe Phe Tyr Leu Arg Arg Glu Gln Met Phe
                245                 250                 255

Val Arg His Leu Phe Asn Arg Ala Gly Thr Val Gly Glu Asn Val Pro
            260                 265                 270

Asp Asp Leu Tyr Ile Lys Gly Ser Gly Ser Thr Ala Asn Leu Ala Ser
        275                 280                 285

Ser Asn Tyr Phe Pro Thr Pro Ser Gly Ser Met Val Thr Ser Asp Ala
    290                 295                 300

Gln Ile Phe Asn Lys Pro Tyr Trp Leu Gln Arg Ala Gln Gly His Asn
305                 310                 315                 320

Asn Gly Ile Cys Trp Gly Asn Gln Leu Phe Val Thr Val Val Asp Thr
                325                 330                 335

Thr Arg Ser Thr Asn Met Ser Leu Cys Ala Ala Ile Ser Thr Ser Glu
            340                 345                 350

Thr Thr Tyr Lys Asn Thr Asn Phe Lys Glu Tyr Leu Arg His Gly Glu
        355                 360                 365

Glu Tyr Asp Leu Gln Phe Ile Phe Gln Leu Cys Lys Ile Thr Leu Thr
    370                 375                 380

Ala Asp Val Met Thr Tyr Ile His Ser Met Asn Ser Thr Ile Leu Glu
385                 390                 395                 400

Asp Trp Asn Phe Gly Leu Gln Pro Pro Gly Gly Thr Leu Glu Asp
                405                 410                 415

Thr Tyr Arg Phe Val Thr Ser Gln Ala Ile Ala Cys Gln Lys His Thr

```
                   420              425              430
Pro Pro Ala Pro Lys Glu Asp Pro Leu Lys Lys Tyr Thr Phe Trp Glu
            435              440              445

Val Asn Leu Lys Glu Lys Phe Ser Ala Asp Leu Asp Gln Phe Pro Leu
        450              455              460

Gly Arg Lys Phe Leu Leu Gln Ala Gly Leu Ala Lys Pro Lys Phe
465              470              475              480

Thr Leu Gly Lys Arg Lys Ala Thr Pro Thr Thr Ser Thr Ser Thr
                485              490              495

Thr Ala Lys Arg Lys Arg Lys Leu
            500              505
```

HPV16 L1 I114K) nucleic acid sequence
(SEQ ID NO: 206)

```
atgtctcttt ggctgcctag tgaggccact gtctacttgc ctcctgtccc agtatctaag   60
gttgtaagca cggatgaata tgttgcacgc acaaacatat attatcatgc aggaacatcc  120
agactacttg cagttggaca tccctatttt cctattaaaa aacctaacaa taacaaaata  180
ttagttccta agtatcagg attacaatac agggtattta gaatacattt acctgacccc  240
aataagtttg gttttcctga cacctcattt tataatccag atacacagcg gctggtttgg  300
gcctgtgtag gtgttgaggt aggtcgtggt cagccattag gtgtgggcat tagtggccat  360
cctttattaa ataaattgga tgacacagaa atgctagtg cttatgcagc aaatgcaggt  420
gtggataata gagaatgtat atctatggat acaaacaaa cacaattgtg tttaattggt  480
tgcaaaccac ctatagggga acactggggc aaaggatccc catgtaccaa tgttgcagta  540
aatccaggtg attgtccacc attagagtta ataaacacag ttattcagga tggtgatatg  600
gttgatactg gctttggtgc tatggacttt actacattac aggctaacaa agtgaagtt  660
ccactggata tttgtacatc tatttgcaaa tatccagatt atattaaaat ggtgtcagaa  720
ccatatggcg acagcttatt tttttattta cgaagggaac aaatgtttgt tagacattta  780
tttaataggg ctggtactgt tggtgaaaat gtaccagacg atttatacat taaaggctct  840
gggtctactg caaatttagc cagttcaaat tattttccta cacctagtgg ttctatggtt  900
acctctgatg cccaaatatt caataaacct tattggttac aacgagcaca gggccacaat  960
aatggcattt gttgggggtaa ccaactattt gttactgttg ttgatactac acgcagtaca 1020
aatatgtcat tatgtgctgc catatctact tcagaaacta catataaaaa tactaacttt 1080
aaggagtacc tacgacatgg ggaggaatat gatttacagt ttatttttca actgtgcaaa 1140
ataaccttaa ctgcagacgt tatgacatac atacattcta tgaattccac tatttttgag 1200
gactggaatt ttggtctaca acctccccca ggaggcacac tagaagatac ttataggttt 1260
gtaacatccc aggcaattgc ttgtcaaaaa catacacctc cagcacctaa gaagatccc 1320
cttaaaaaat acactttttg ggaagtaaat ttaaaggaaa gttttctgc agacctagat 1380
cagtttcctt taggacgcaa attttttacta caagcaggat tgaaggccaa accaaaattt 1440
acattaggaa aacgaaaagc tacacccacc acctcatcta cctctacaac tgctaaacgc 1500
aaaaaacgta agctgtaa                                              1518
```

HPV L2 Protein Sequence
(SEQ ID NO: 207)

```
Met Arg His Lys Arg Ser Ala Lys Arg Thr Lys Arg Ala Ser Ala Thr
1               5                   10                  15

Gln Leu Tyr Lys Thr Cys Lys Gln Ala Gly Thr Cys Pro Pro Asp Ile
            20                  25                  30

Ile Pro Lys Val Glu Gly Lys Thr Ile Ala Asp Gln Ile Leu Gln Tyr
        35                  40                  45
```

-continued

```
Gly Ser Met Gly Val Phe Phe Gly Gly Leu Gly Ile Gly Thr Gly Ser
     50                  55                  60

Gly Thr Gly Gly Arg Thr Gly Tyr Ile Pro Leu Gly Thr Arg Pro Pro
 65                  70                  75                  80

Thr Ala Thr Asp Thr Leu Ala Pro Val Arg Pro Pro Leu Thr Val Asp
                     85                  90                  95

Pro Val Gly Pro Ser Asp Pro Ser Ile Val Ser Leu Val Glu Glu Thr
                100                 105                 110

Ser Phe Ile Asp Ala Gly Ala Pro Thr Ser Val Pro Ser Ile Pro Pro
            115                 120                 125

Asp Val Ser Gly Phe Ser Ile Thr Thr Ser Thr Asp Thr Thr Pro Ala
        130                 135                 140

Ile Leu Asp Ile Asn Asn Thr Val Thr Val Thr Thr His Asn Asn
145                 150                 155                 160

Pro Thr Phe Thr Asp Pro Ser Val Leu Gln Pro Pro Thr Pro Ala Glu
                165                 170                 175

Thr Gly Gly His Phe Thr Leu Ser Ser Ser Thr Ile Ser Thr His Asn
                180                 185                 190

Tyr Glu Glu Ile Pro Met Asp Thr Phe Ile Val Ser Thr Asn Pro Asn
            195                 200                 205

Thr Val Thr Ser Ser Thr Pro Ile Pro Gly Ser Arg Pro Val Ala Arg
    210                 215                 220

Leu Gly Leu Tyr Ser Arg Thr Thr Gln Gln Val Lys Val Asp Pro
225                 230                 235                 240

Ala Phe Val Thr Thr Pro Thr Lys Leu Ile Thr Tyr Asp Asn Pro Ala
                245                 250                 255

Tyr Glu Gly Ile Asp Val Asp Asn Thr Leu Tyr Phe Ser Ser Asn Asp
            260                 265                 270

Asn Ser Ile Asn Ile Ala Pro Asp Pro Asp Phe Leu Asp Ile Val Ala
        275                 280                 285

Leu His Arg Pro Ala Leu Thr Ser Arg Arg Thr Gly Ile Arg Tyr Ser
    290                 295                 300

Arg Ile Gly Asn Lys Gln Thr Leu Arg Thr Arg Ser Gly Lys Ser Ile
305                 310                 315                 320

Gly Ala Lys Val His Tyr Tyr Asp Phe Ser Thr Ile Asp Pro Ala
                325                 330                 335

Glu Glu Ile Glu Leu Gln Thr Ile Thr Pro Ser Thr Tyr Thr Thr Thr
            340                 345                 350

Ser His Ala Ala Ser Pro Thr Ser Ile Asn Asn Gly Leu Tyr Asp Ile
        355                 360                 365

Tyr Ala Asp Asp Phe Ile Thr Asp Thr Ser Thr Pro Val Pro Ser
    370                 375                 380

Val Pro Ser Thr Ser Leu Ser Gly Tyr Ile Pro Ala Asn Thr Thr Ile
385                 390                 395                 400

Pro Phe Gly Gly Ala Tyr Asn Ile Pro Leu Val Ser Gly Pro Asp Ile
                405                 410                 415

Pro Ile Asn Ile Thr Asp Gln Ala Pro Ser Leu Ile Pro Ile Val Pro
            420                 425                 430

Gly Ser Pro Gln Tyr Thr Ile Ile Ala Asp Ala Gly Asp Phe Tyr Leu
        435                 440                 445

His Pro Ser Tyr Tyr Met Leu Arg Lys Arg Lys Arg Leu Pro Tyr
    450                 455                 460

Phe Phe Ser Asp Val Ser Leu Ala Ala
```

-continued

HPV16 L2 nucleic acid sequence (SEQ ID NO: 208)

```
atgcgacaca acgttctgc aaaacgcaca aaacgtgcat cggctaccca actttataaa   60
acatgcaaac aggcaggtac atgtccacct gacattatac ctaaggttga aggcaaaact  120
attgctgatc aaatattaca atatggaagt atgggtgtat tttttggtgg gttaggaatt  180
ggaacagggt cgggtacagg cggacgcact gggtatattc cattgggaac aaggcctccc  240
acagctacag atacacttgc tcctgtaaga cccccttaa cagtagatcc tgtgggccct  300
tctgatcctt ctatagtttc tttagtggaa gaaactagtt ttattgatgc tggtgcacca  360
acatctgtac cttccattcc cccagatgta tcaggattta gtattactac ttcaactgat  420
accacacctg ctatattaga tattaataat actgttacta ctgttactac acataataat  480
cccactttca ctgacccatc tgtattgcag cctccaacac ctgcagaaac tggagggcat  540
tttacacttt catcatccac tattagtaca cataattatg aagaaattcc tatggataca  600
tttattgtta gcacaaaccc taacacagta actagtagca cacccatacc agggtctcgc  660
ccagtggcac gcctaggatt atatagtcgc acaacacaac aagttaaagt tgtagaccct  720
gcttttgtaa ccactcccac taaacttatt acatatgata tcctgcata tgaaggtata  780
gatgtggata atacattata ttttctagt aatgataata gtattaatat agctccagat  840
cctgactttt tggatatagt tgctttacat aggccagcat taacctctag gcgtactggc  900
ataaggtaca gtagaattgg taataaacaa acactacgta ctcgtagtgg aaaatctata  960
ggtgctaagg tacattatta ttatgatttt agtaccattg atcctgcaga agaaatagaa 1020
ttacaaacta taacaccttc tacatatact accacttcac atgcagcctc acctactct 1080
attaataatg gattatatga tttatgca gatgactta ttacagatac ttctacaacc 1140
ccggtaccat ctgtaccctc tacatcttta tcaggttata ttcctgcaaa tacaacaatt 1200
ccttttggtg gtgcatacaa tattcctta gtatcaggtc ctgatatacc cattaatata 1260
actgaccaag ctccttcatt aattcctata gttccagggt ctccacaata tacaattatt 1320
gctgatgcag gtgactttta tttacatcct agttattaca tgttacgaaa acgacgtaaa 1380
cgtttaccat atttttttc agatgtctct ttggct                             1416
```

Furin Cleavage site (SEQ ID NO: 209)

R X R/K R

Furin Cleavage site (SEQ ID NO: 210)

Arg Val Lys Arg

An MMP-cleavable peptide substrate (SEQ ID NO: 211)

Glu Pro Cit Gly Hof Tyr Leu

An MMP-cleavable peptide substrate (SEQ ID NO: 212)

Gly Pro Leu Gly Ile Ala Gly Gln

An MMP-cleavable peptide substrate (SEQ ID NO: 213)

Pro Val Gly Leu Ile Gly

A Polyglutamic acid docking site (SEQ ID NO: 214)

EEEEEEEC.

A Polyglutamic acid docking site (SEQ ID NO: 215)

CEEEEEEEEC.

EBNA3C peptide aa 284-293 binds HLA-A2.01

(SEQ ID NO: 216)

LLDRVRFMGV

```
EBV peptide
                                                                        (SEQ ID NO: 217)
(K)GILGFVFTL(T)(V)

Chicken Pox Virus CD8+ T cell epitope
                                                                        (SEQ ID NO: 218)
SLPRSRTPI Chicken Pox Virus CD8+ T cell epitope
                                                                        (DEQ ID NO: 219)
SAPLPSNRV OVA peptide
                                                                        (SEQ ID NO: 220)
SIINFEKL RG-1 VLP sequence
                                                                        (SEQ ID NO: 221)
MSLWLPSEAT VYLPPVPVSK VVSTDEYVAR TNIYYHAGTS RLLAVGHPYF PIKKPNNNKI

LVPKVSGLQY RVFRIHLPDP NKFGFPDTSF YNPDTQRLVW ACVGVEVGRG QPLGVGISGH

PLLNKLDDTE NASAYAQLYK TCKQAGTCPP DIIPKVANAG VDNRECISMD YKQTQLCLIG

CKPPIGEHWG KGSPCTNVAV NPGDCPPLEL INTVIQDGDM VDTGFGAMDF TTLQANKSEV

PLDICTSICK YPDYIKMVSE PYGDSLFFYL RREQMFVRHL FNRAGAVGEN VPDDLYIKGS

GSTANLASSN YFPTPSGSMV TSDAQIFNKP YWLQRAQGHN NGICWGNQLF VTVVDTTRST

NMSLCAAIST SETTYKNTNF KEYLRHGEEY DLQFIFQLCK ITLTADVMTY IHSMNSTILE

DWNFGLQPPP GGTLEDTYRF VTSQAIACQK HTPPAPKEDP LKKYTFWEVN LKEKFSADLD

QFPLGRKFLL QAGLKAKPKF TLGKRKATPT TSSTSTTAKR KKRKLSR

HPV L2 protein derived peptide
                                                                        (SEQ ID NOO: 222)
QLYKTCKQAG TCPPDIIPKV
```

---

We claim:

1. A virus-like particle (VLP), comprising in order from amino terminus to carboxy terminus:
   a) a papilloma virus L1 protein,
   b) at least one antigen conjugated to the L1 protein via a cysteine, lysine, or arginine residue of the L1 protein, wherein the at least one antigen comprises at least one T cell epitope, and
   c) at least one peptide cleavage sequence,
   wherein the T cell epitope is from a human pathogen heterologous to the papilloma virus of the VLP, and
   wherein the at least one antigen is not a tumor-associated antigen.

2. The VLP of claim 1, wherein the L1 protein is a mouse papilloma virus L1 protein.

3. The VLP of claim 1, wherein the L1 protein is a full length L1 protein.

4. The VLP of claim 1, wherein the L1 protein comprises at least one truncation on the amino terminus or the carboxy terminus or both the amino terminus and the carboxy terminus.

5. The VLP of claim 1, wherein the antigen comprises a CD8+ or CD4+ T cell epitope, and wherein when the antigen is present inside a human subject and released from the VLP by proteolytic cleavage the antigen stimulates CD8+ or CD4+ T cells within the human subject.

6. The VLP of claim 1, wherein the L1 protein is a chimeric L1 protein with a peptide sequence from at least two different strains of papilloma virus.

7. The VLP of claim 1, wherein the at least one antigen binds to a major histocompatibility class I molecule.

8. The VLP of claim 1, wherein the at least one antigen binds to a major histocompatibility class II molecule.

9. The VLP of claim 1, wherein the at least one peptide cleavage sequence is:
   i) selected from a furin cleavage sequence, a matrix metalloprotease cleavage sequence, and A Disintegrin And Metalloproteinase (ADAM) cleavage sequence, or
   ii) is one or more of SEQ ID NO:209 to 213.

10. The VLP of claim 1, wherein the at least one T cell epitope comprises one or more of SEQ ID NOs: 1 to 204.

11. The VLP of claim 1, wherein the at least one antigen is:
   A) from at least one vaccine for inoculating children against one or more childhood diseases,
   B) a viral antigenic peptide,
   C) a bacterial antigenic peptide,
   D) a parasitic antigenic peptide, or
   E) a fungus antigenic peptide.

12. The VLP of claim 11, wherein:
   a) the at least one antigen is at least a viral antigen, and wherein the viral antigen is from one or more of: vaccinia, Varicella zoster, coronavirus, cytomegalovirus, herpes simplex virus, Herpes zoster, rubella, hepatitis, influenza, measles, mumps, poliovirus, variola, rabies, dengue, Ebola, West Nile, yellow fever, and zika,
   b) the at least one antigen is at least a bacterial antigenic peptide, and wherein the bacterial antigen is from one or more of: *Bordetella pertussis, Clostridium tetani, Chlamydia trachomatis, Corynebacterium diphtheriae, Hemophilus influenza, Neisseria meningitidis, Streptococcus, Vibrio cholera, Mycobacterium tuberculosis, Bacillus* Calmette-Guérin, *Salmonella, Escherichia coli, Legionella pneumophila, Rickettsia, Treponema pallidum pallidum, Bacillus anthracis, Clostridium botulinum*, and *Yersinia*, or
   c) the at least one antigen is at least a parasitic antigenic peptide, and wherein the parasitic antigen is from one or more of: *Entamoeba histolytica, Toxoplasma gondii, Trichinella, Trichomonas, Trypanosoma*, and *Plasmodium*.

13. The VLP of claim 1, wherein the L1 protein is from Bovine papilloma virus (BPV), Human papilloma virus (HPV), Rabbit papilloma virus (RPV), or Mouse papilloma virus (MPV).

14. The VLP of claim 1, wherein the L1 protein sequence comprises SEQ ID NO:221 or SEQ ID NO:222.

* * * * *

SEQUENCE LISTING

```
<160> NUMBER OF SEQ ID NOS: 222

<210> SEQ ID NO 1
<211> LENGTH: 13
<212> TYPE: PRT
<213> ORGANISM: Measles virus

<400> SEQUENCE: 1

Ser Met Leu Asn Ser Gln Ala Ile Asp Asn Leu Arg Ala
1               5                   10

<210> SEQ ID NO 2
<211> LENGTH: 9
<212> TYPE: PRT
<213> ORGANISM: Measles virus

<400> SEQUENCE: 2

Leu Met Ile Asp Arg Pro Tyr Val Leu
1               5

<210> SEQ ID NO 3
<211> LENGTH: 12
<212> TYPE: PRT
<213> ORGANISM: Measles virus

<400> SEQUENCE: 3

Val Ile Ile Asn Asp Asp Gln Gly Leu Phe Lys Val
1               5                   10
```

```
<210> SEQ ID NO 4
<211> LENGTH: 9
<212> TYPE: PRT
<213> ORGANISM: Measles virus

<400> SEQUENCE: 4

Lys Ile Ile Asp Asn Thr Glu Gln Leu
1               5

<210> SEQ ID NO 5
<211> LENGTH: 10
<212> TYPE: PRT
<213> ORGANISM: Measles virus

<400> SEQUENCE: 5

Arg Leu Ser Asp Asn Gly Tyr Tyr Thr Val
1               5                   10

<210> SEQ ID NO 6
<211> LENGTH: 9
<212> TYPE: PRT
<213> ORGANISM: Measles virus

<400> SEQUENCE: 6

Lys Leu Trp Glu Ser Pro Gln Glu Ile
1               5

<210> SEQ ID NO 7
<211> LENGTH: 9
<212> TYPE: PRT
<213> ORGANISM: Measles virus

<400> SEQUENCE: 7

Lys Leu Ile Asp Gly Phe Phe Pro Ala
1               5

<210> SEQ ID NO 8
<211> LENGTH: 8
<212> TYPE: PRT
<213> ORGANISM: Measles virus

<400> SEQUENCE: 8

Ser Met Tyr Arg Val Phe Glu Val
1               5

<210> SEQ ID NO 9
<211> LENGTH: 9
<212> TYPE: PRT
<213> ORGANISM: Measles virus

<400> SEQUENCE: 9

Lys Val Ser Pro Tyr Leu Phe Thr Val
1               5

<210> SEQ ID NO 10
<211> LENGTH: 11
<212> TYPE: PRT
<213> ORGANISM: Measles virus

<400> SEQUENCE: 10

Ser Leu Met Pro Glu Glu Thr Leu His Gln Val
1               5                   10

<210> SEQ ID NO 11
```

```
<211> LENGTH: 11
<212> TYPE: PRT
<213> ORGANISM: Measles virus

<400> SEQUENCE: 11

Arg Gln Ala Gly Gln Glu Met Ile Leu Ala Val
1               5                   10

<210> SEQ ID NO 12
<211> LENGTH: 10
<212> TYPE: PRT
<213> ORGANISM: Measles virus

<400> SEQUENCE: 12

Gly Ser Ala Pro Ile Ser Met Gly Phe Arg
1               5                   10

<210> SEQ ID NO 13
<211> LENGTH: 11
<212> TYPE: PRT
<213> ORGANISM: Measles virus

<400> SEQUENCE: 13

Gly Met Tyr Gly Gly Thr Tyr Leu Val Glu Lys
1               5                   10

<210> SEQ ID NO 14
<211> LENGTH: 13
<212> TYPE: PRT
<213> ORGANISM: Measles virus

<400> SEQUENCE: 14

Ala Val Arg Asp Leu Glu Arg Ala Met Thr Thr Leu Lys
1               5                   10

<210> SEQ ID NO 15
<211> LENGTH: 11
<212> TYPE: PRT
<213> ORGANISM: Measles virus

<400> SEQUENCE: 15

Tyr Val Tyr Asp His Ser Gly Glu Ala Val Lys
1               5                   10

<210> SEQ ID NO 16
<211> LENGTH: 9
<212> TYPE: PRT
<213> ORGANISM: Measles virus

<400> SEQUENCE: 16

Ala Ile Tyr Thr Ala Glu Ile His Lys
1               5

<210> SEQ ID NO 17
<211> LENGTH: 10
<212> TYPE: PRT
<213> ORGANISM: Measles virus
<220> FEATURE:
<221> NAME/KEY: MISC_FEATURE
<222> LOCATION: (10)..(10)
<223> OTHER INFORMATION: May or may not be present

<400> SEQUENCE: 17

Gly Pro Arg Gln Ala Gln Val Ser Phe Leu
1               5                   10
```

```
<210> SEQ ID NO 18
<211> LENGTH: 9
<212> TYPE: PRT
<213> ORGANISM: Measles virus

<400> SEQUENCE: 18

Tyr Pro Ala Leu Gly Leu His Glu Phe
1               5

<210> SEQ ID NO 19
<211> LENGTH: 8
<212> TYPE: PRT
<213> ORGANISM: Measles virus

<400> SEQUENCE: 19

Arg Pro Gly Leu Lys Pro Asp Leu
1               5

<210> SEQ ID NO 20
<211> LENGTH: 12
<212> TYPE: PRT
<213> ORGANISM: Measles virus

<400> SEQUENCE: 20

Ile Pro Tyr Gln Gly Ser Gly Lys Gly Val Ser Phe
1               5                   10

<210> SEQ ID NO 21
<211> LENGTH: 11
<212> TYPE: PRT
<213> ORGANISM: Measles virus

<400> SEQUENCE: 21

Lys Pro Asn Leu Ser Ser Lys Arg Ser Glu Leu
1               5                   10

<210> SEQ ID NO 22
<211> LENGTH: 8
<212> TYPE: PRT
<213> ORGANISM: Measles virus

<400> SEQUENCE: 22

Arg Pro Ile Tyr Gly Leu Glu Val
1               5

<210> SEQ ID NO 23
<211> LENGTH: 9
<212> TYPE: PRT
<213> ORGANISM: Measles virus

<400> SEQUENCE: 23

Asp Ala Leu Leu Arg Leu Gln Ala Met
1               5

<210> SEQ ID NO 24
<211> LENGTH: 8
<212> TYPE: PRT
<213> ORGANISM: Measles virus

<400> SEQUENCE: 24

Phe Pro Lys Leu Gly Lys Thr Leu
1               5

<210> SEQ ID NO 25
```

```
<211> LENGTH: 8
<212> TYPE: PRT
<213> ORGANISM: Measles virus

<400> SEQUENCE: 25

Leu Leu Lys Glu Ala Thr Glu Leu
1               5

<210> SEQ ID NO 26
<211> LENGTH: 9
<212> TYPE: PRT
<213> ORGANISM: Measles virus

<400> SEQUENCE: 26

Ile Pro Pro Met Lys Asn Leu Ala Leu
1               5

<210> SEQ ID NO 27
<211> LENGTH: 9
<212> TYPE: PRT
<213> ORGANISM: Measles virus

<400> SEQUENCE: 27

Asp Ile Lys Glu Lys Val Ile Asn Leu
1               5

<210> SEQ ID NO 28
<211> LENGTH: 9
<212> TYPE: PRT
<213> ORGANISM: Measles virus

<400> SEQUENCE: 28

His Ile Leu Ala Lys Ser Thr Ala Leu
1               5

<210> SEQ ID NO 29
<211> LENGTH: 8
<212> TYPE: PRT
<213> ORGANISM: Measles virus

<400> SEQUENCE: 29

Tyr Leu Lys Asp Lys Ala Leu Ala
1               5

<210> SEQ ID NO 30
<211> LENGTH: 9
<212> TYPE: PRT
<213> ORGANISM: Measles virus

<400> SEQUENCE: 30

Gly Leu Asn Glu Lys Leu Val Phe Tyr
1               5

<210> SEQ ID NO 31
<211> LENGTH: 10
<212> TYPE: PRT
<213> ORGANISM: Measles virus

<400> SEQUENCE: 31

Arg Ile Thr His Val Asp Thr Glu Ser Tyr
1               5                   10

<210> SEQ ID NO 32
<211> LENGTH: 9
<212> TYPE: PRT
```

<213> ORGANISM: Measles virus

<400> SEQUENCE: 32

Leu Leu Lys Lys Gly Asn Ser Leu Tyr
1               5

<210> SEQ ID NO 33
<211> LENGTH: 8
<212> TYPE: PRT
<213> ORGANISM: Measles virus

<400> SEQUENCE: 33

Ser Lys Glu Ser Gln His Val Tyr
1               5

<210> SEQ ID NO 34
<211> LENGTH: 8
<212> TYPE: PRT
<213> ORGANISM: Measles virus

<400> SEQUENCE: 34

Ala Gln Arg Leu Asn Glu Ile Tyr
1               5

<210> SEQ ID NO 35
<211> LENGTH: 9
<212> TYPE: PRT
<213> ORGANISM: Measles virus

<400> SEQUENCE: 35

Ser Gln Gln Gly Met Phe His Ala Tyr
1               5

<210> SEQ ID NO 36
<211> LENGTH: 9
<212> TYPE: PRT
<213> ORGANISM: Measles virus

<400> SEQUENCE: 36

Ser Met Ile Asp Leu Val Thr Lys Phe
1               5

<210> SEQ ID NO 37
<211> LENGTH: 9
<212> TYPE: PRT
<213> ORGANISM: Measles virus

<400> SEQUENCE: 37

Ile Val Ser Ser His Phe Phe Val Tyr
1               5

<210> SEQ ID NO 38
<211> LENGTH: 12
<212> TYPE: PRT
<213> ORGANISM: Measles virus

<400> SEQUENCE: 38

Glu Pro Ile Gly Ser Leu Ala Ile Glu Glu Ala Met
1               5                   10

<210> SEQ ID NO 39
<211> LENGTH: 10
<212> TYPE: PRT
<213> ORGANISM: Measles virus

<400> SEQUENCE: 39

Glu Pro Ile Arg Asp Ala Leu Asn Ala Met
1               5                   10

<210> SEQ ID NO 40
<211> LENGTH: 9
<212> TYPE: PRT
<213> ORGANISM: Measles virus

<400> SEQUENCE: 40

Ala Pro Val Phe His Met Thr Asn Tyr
1               5

<210> SEQ ID NO 41
<211> LENGTH: 9
<212> TYPE: PRT
<213> ORGANISM: Measles virus

<400> SEQUENCE: 41

Ser Ala Val Arg Ile Ala Thr Val Tyr
1               5

<210> SEQ ID NO 42
<211> LENGTH: 10
<212> TYPE: PRT
<213> ORGANISM: Measles virus

<400> SEQUENCE: 42

Met Pro Glu Glu Thr Leu His Gln Val Met
1               5                   10

<210> SEQ ID NO 43
<211> LENGTH: 10
<212> TYPE: PRT
<213> ORGANISM: Measles virus

<400> SEQUENCE: 43

Leu Pro Ala Pro Ile Gly Gly Met Asn Tyr
1               5                   10

<210> SEQ ID NO 44
<211> LENGTH: 9
<212> TYPE: PRT
<213> ORGANISM: Measles virus

<400> SEQUENCE: 44

Ala Glu Gly Gly Glu Ile His Glu Leu
1               5

<210> SEQ ID NO 45
<211> LENGTH: 9
<212> TYPE: PRT
<213> ORGANISM: Measles virus

<400> SEQUENCE: 45

Ala Glu Val Asp Gly Asp Val Lys Leu
1               5

<210> SEQ ID NO 46
<211> LENGTH: 10
<212> TYPE: PRT
<213> ORGANISM: Measles virus

<400> SEQUENCE: 46

Leu Glu Thr Arg Thr Thr Asn Gln Phe Leu
1               5                   10

<210> SEQ ID NO 47
<211> LENGTH: 9
<212> TYPE: PRT
<213> ORGANISM: Measles virus

<400> SEQUENCE: 47

Lys Glu Ser Gln His Val Tyr Tyr Leu
1               5

<210> SEQ ID NO 48
<211> LENGTH: 10
<212> TYPE: PRT
<213> ORGANISM: Measles virus

<400> SEQUENCE: 48

Tyr Glu Ser Gly Val Arg Ile Ala Ser Leu
1               5                   10

<210> SEQ ID NO 49
<211> LENGTH: 11
<212> TYPE: PRT
<213> ORGANISM: Measles virus

<400> SEQUENCE: 49

Gln Glu Ile Ser Arg His Gln Ala Leu Gly Tyr
1               5                   10

<210> SEQ ID NO 50
<211> LENGTH: 10
<212> TYPE: PRT
<213> ORGANISM: Measles virus

<400> SEQUENCE: 50

Lys Glu Ile Lys Glu Thr Gly Arg Leu Phe
1               5                   10

<210> SEQ ID NO 51
<211> LENGTH: 12
<212> TYPE: PRT
<213> ORGANISM: Measles virus

<400> SEQUENCE: 51

Ala Glu Asn Leu Ile Ser Asn Gly Ile Gly Lys Tyr
1               5                   10

<210> SEQ ID NO 52
<211> LENGTH: 9
<212> TYPE: PRT
<213> ORGANISM: Measles virus

<400> SEQUENCE: 52

Ala Val Arg Asp Leu Glu Arg Ala Met
1               5

<210> SEQ ID NO 53
<211> LENGTH: 9
<212> TYPE: PRT
<213> ORGANISM: Measles virus

<400> SEQUENCE: 53

Phe Arg Ser Val Asn Ala Val Ala Phe
1               5

<210> SEQ ID NO 54
<211> LENGTH: 9
<212> TYPE: PRT
<213> ORGANISM: Measles virus

<400> SEQUENCE: 54

Ala Arg Val Pro His Ala Tyr Ser Leu
1               5

<210> SEQ ID NO 55
<211> LENGTH: 14
<212> TYPE: PRT
<213> ORGANISM: Measles virus
<220> FEATURE:
<221> NAME/KEY: MISC_FEATURE
<222> LOCATION: (13)..(14)
<223> OTHER INFORMATION: May or may not be present

<400> SEQUENCE: 55

Thr Asp Thr Pro Ile Val Tyr Asn Asp Arg Asn Leu Leu Asp
1               5                   10

<210> SEQ ID NO 56
<211> LENGTH: 8
<212> TYPE: PRT
<213> ORGANISM: Measles virus

<400> SEQUENCE: 56

Lys Lys Gln Ile Asn Arg Gln Asn
1               5

<210> SEQ ID NO 57
<211> LENGTH: 9
<212> TYPE: PRT
<213> ORGANISM: Measles virus

<400> SEQUENCE: 57

Asp Thr Gly Val Asp Thr Arg Ile Trp
1               5

<210> SEQ ID NO 58
<211> LENGTH: 8
<212> TYPE: PRT
<213> ORGANISM: Measles virus

<400> SEQUENCE: 58

Asp Gln Gly Leu Phe Lys Val Leu
1               5

<210> SEQ ID NO 59
<211> LENGTH: 10
<212> TYPE: PRT
<213> ORGANISM: Measles virus

<400> SEQUENCE: 59

Gly Lys Ile Ile Asp Asn Thr Glu Gln Leu
1               5                   10

<210> SEQ ID NO 60
<211> LENGTH: 11
<212> TYPE: PRT
<213> ORGANISM: Measles virus

<400> SEQUENCE: 60

Gly Arg Leu Val Pro Gln Val Arg Val Ile Asp
1               5                   10

<210> SEQ ID NO 61
<211> LENGTH: 14
<212> TYPE: PRT
<213> ORGANISM: Measles virus

<400> SEQUENCE: 61

Gly Pro Pro Ile Ser Leu Glu Arg Leu Asp Val Gly Thr Asn
1               5                   10

<210> SEQ ID NO 62
<211> LENGTH: 16
<212> TYPE: PRT
<213> ORGANISM: Measles virus
<220> FEATURE:
<221> NAME/KEY: MISC_FEATURE
<222> LOCATION: (16)..(16)
<223> OTHER INFORMATION: May or may not be present

<400> SEQUENCE: 62

Ala Pro Val Phe His Met Thr Asn Tyr Leu Glu Gln Pro Val Ser Asn
1               5                   10                  15

<210> SEQ ID NO 63
<211> LENGTH: 9
<212> TYPE: PRT
<213> ORGANISM: Measles virus

<400> SEQUENCE: 63

Pro Thr Thr Ile Arg Gly Gln Phe Ser
1               5

<210> SEQ ID NO 64
<211> LENGTH: 9
<212> TYPE: PRT
<213> ORGANISM: Measles virus

<400> SEQUENCE: 64

His Tyr Arg Glu Val Asn Leu Val Tyr
1               5

<210> SEQ ID NO 65
<211> LENGTH: 11
<212> TYPE: PRT
<213> ORGANISM: Measles virus
<220> FEATURE:
<221> NAME/KEY: MISC_FEATURE
<222> LOCATION: (1)..(1)
<223> OTHER INFORMATION: May or may not be present
<220> FEATURE:
<221> NAME/KEY: MISC_FEATURE
<222> LOCATION: (10)..(11)
<223> OTHER INFORMATION: May or may not be present

<400> SEQUENCE: 65

Lys Lys Val Asp Thr Asn Phe Ile Tyr Gln Gln
1               5                   10

<210> SEQ ID NO 66
<211> LENGTH: 15
<212> TYPE: PRT
<213> ORGANISM: Measles virus

<400> SEQUENCE: 66

Leu Ser Glu Ile Lys Gly Val Ile Val His Arg Leu Glu Gly Val

```
1               5                  10                 15
```

<210> SEQ ID NO 67
<211> LENGTH: 9
<212> TYPE: PRT
<213> ORGANISM: Measles virus

<400> SEQUENCE: 67

Leu Asp Arg Leu Val Arg Leu Ile Gly
1               5

<210> SEQ ID NO 68
<211> LENGTH: 9
<212> TYPE: PRT
<213> ORGANISM: Measles virus

<400> SEQUENCE: 68

Arg Arg Tyr Pro Asp Ala Val Tyr Leu
1               5

<210> SEQ ID NO 69
<211> LENGTH: 10
<212> TYPE: PRT
<213> ORGANISM: Hepatitis B virus

<400> SEQUENCE: 69

Phe Leu Pro Ser Asp Phe Phe Pro Ser Val
1               5                  10

<210> SEQ ID NO 70
<211> LENGTH: 9
<212> TYPE: PRT
<213> ORGANISM: Hepatitis B virus

<400> SEQUENCE: 70

Phe Leu Leu Thr Arg Ile Leu Thr Ile
1               5

<210> SEQ ID NO 71
<211> LENGTH: 9
<212> TYPE: PRT
<213> ORGANISM: Hepatitis B virus

<400> SEQUENCE: 71

Trp Leu Ser Leu Leu Val Pro Phe Val
1               5

<210> SEQ ID NO 72
<211> LENGTH: 9
<212> TYPE: PRT
<213> ORGANISM: Hepatitis B virus

<400> SEQUENCE: 72

Gly Leu Ser Arg Tyr Val Ala Arg Leu
1               5

<210> SEQ ID NO 73
<211> LENGTH: 9
<212> TYPE: PRT
<213> ORGANISM: Hepatitis B virus

<400> SEQUENCE: 73

Phe Leu Leu Ser Leu Gly Ile His Leu
1               5

<210> SEQ ID NO 74
<211> LENGTH: 20
<212> TYPE: PRT
<213> ORGANISM: Hepatitis B virus

<400> SEQUENCE: 74

Met Asp Ile Asp Pro Tyr Lys Glu Phe Gly Ala Thr Val Glu Leu Leu
1               5                   10                  15

Ser Phe Leu Pro
            20

<210> SEQ ID NO 75
<211> LENGTH: 25
<212> TYPE: PRT
<213> ORGANISM: Hepatitis B virus

<400> SEQUENCE: 75

Arg Asp Leu Leu Asp Thr Ala Ser Ala Leu Tyr Arg Glu Ala Leu Glu
1               5                   10                  15

Ser Pro Glu His Cys Ser Pro His His
            20                  25

<210> SEQ ID NO 76
<211> LENGTH: 25
<212> TYPE: PRT
<213> ORGANISM: Hepatitis B virus

<400> SEQUENCE: 76

Thr Trp Val Gly Val Asn Leu Glu Asp Pro Ala Ser Arg Asp Leu Val
1               5                   10                  15

Val Ser Tyr Val Asn Thr Asn Met Gly
            20                  25

<210> SEQ ID NO 77
<211> LENGTH: 16
<212> TYPE: PRT
<213> ORGANISM: Hepatitis B virus

<400> SEQUENCE: 77

Val Val Ser Tyr Val Asn Thr Asn Met Gly Leu Lys Phe Arg Gln Leu
1               5                   10                  15

<210> SEQ ID NO 78
<211> LENGTH: 12
<212> TYPE: PRT
<213> ORGANISM: Hepatitis B virus

<400> SEQUENCE: 78

Val Val Ser Tyr Val Asn Thr Asn Met Gly Leu Lys
1               5                   10

<210> SEQ ID NO 79
<211> LENGTH: 21
<212> TYPE: PRT
<213> ORGANISM: Hepatitis B virus

<400> SEQUENCE: 79

Leu Leu Trp Phe His Ile Ser Cys Leu Thr Phe Gly Arg Glu Thr Val
1               5                   10                  15

Ile Glu Tyr Leu Val
            20

```
<210> SEQ ID NO 80
<211> LENGTH: 11
<212> TYPE: PRT
<213> ORGANISM: Hepatitis B virus

<400> SEQUENCE: 80

Leu Leu Trp Phe His Ile Ser Cys Leu Thr Phe
1               5                   10

<210> SEQ ID NO 81
<211> LENGTH: 12
<212> TYPE: PRT
<213> ORGANISM: Hepatitis B virus

<400> SEQUENCE: 81

Val Ser Phe Gly Val Trp Ile Arg Thr Pro Pro Ala
1               5                   10

<210> SEQ ID NO 82
<211> LENGTH: 21
<212> TYPE: PRT
<213> ORGANISM: Hepatitis B virus

<400> SEQUENCE: 82

Val Ser Phe Gly Val Trp Ile Arg Thr Pro Pro Ala Tyr Arg Pro Pro
1               5                   10                  15

Asn Ala Pro Ile Leu
            20

<210> SEQ ID NO 83
<211> LENGTH: 12
<212> TYPE: PRT
<213> ORGANISM: Hepatitis B virus

<400> SEQUENCE: 83

Pro Pro Ala Tyr Arg Pro Pro Asn Ala Pro Ile Leu
1               5                   10

<210> SEQ ID NO 84
<211> LENGTH: 12
<212> TYPE: PRT
<213> ORGANISM: Hepatitis B virus

<400> SEQUENCE: 84

Trp Ile Arg Thr Pro Pro Ala Tyr Arg Pro Pro Asn
1               5                   10

<210> SEQ ID NO 85
<211> LENGTH: 9
<212> TYPE: PRT
<213> ORGANISM: Hepatitis B virus

<400> SEQUENCE: 85

Leu Leu Ala Gln Phe Thr Ser Ala Ile
1               5

<210> SEQ ID NO 86
<211> LENGTH: 8
<212> TYPE: PRT
<213> ORGANISM: Hepatitis B virus

<400> SEQUENCE: 86

Ala Leu Met Pro Leu Tyr Ala Cys
1               5
```

```
<210> SEQ ID NO 87
<211> LENGTH: 9
<212> TYPE: PRT
<213> ORGANISM: Hepatitis B virus

<400> SEQUENCE: 87

Lys Leu His Leu Tyr Ser His Pro Ile
1               5

<210> SEQ ID NO 88
<211> LENGTH: 10
<212> TYPE: PRT
<213> ORGANISM: Hepatitis B virus

<400> SEQUENCE: 88

Tyr Leu His Thr Leu Trp Lys Ala Gly Ile
1               5                   10

<210> SEQ ID NO 89
<211> LENGTH: 10
<212> TYPE: PRT
<213> ORGANISM: Hepatitis B virus

<400> SEQUENCE: 89

Tyr Leu His Thr Leu Trp Lys Ala Gly Val
1               5                   10

<210> SEQ ID NO 90
<211> LENGTH: 10
<212> TYPE: PRT
<213> ORGANISM: Hepatitis B virus

<400> SEQUENCE: 90

Leu Leu Val Pro Phe Val Gln Trp Phe Val
1               5                   10

<210> SEQ ID NO 91
<211> LENGTH: 10
<212> TYPE: PRT
<213> ORGANISM: Hepatitis B virus

<400> SEQUENCE: 91

Ile Leu Leu Leu Cys Leu Ile Phe Leu Leu
1               5                   10

<210> SEQ ID NO 92
<211> LENGTH: 9
<212> TYPE: PRT
<213> ORGANISM: Hepatitis B virus

<400> SEQUENCE: 92

Val Leu Leu Asp Tyr Gln Gly Met Leu
1               5

<210> SEQ ID NO 93
<211> LENGTH: 10
<212> TYPE: PRT
<213> ORGANISM: Hepatitis B virus

<400> SEQUENCE: 93

Leu Leu Pro Ile Phe Phe Cys Leu Trp Val
1               5                   10

<210> SEQ ID NO 94
```

<211> LENGTH: 9
<212> TYPE: PRT
<213> ORGANISM: Hepatitis B virus

<400> SEQUENCE: 94

Val Leu Gln Ala Gly Phe Phe Leu Leu
1               5

<210> SEQ ID NO 95
<211> LENGTH: 9
<212> TYPE: PRT
<213> ORGANISM: Hepatitis B virus

<400> SEQUENCE: 95

Pro Leu Leu Pro Ile Phe Phe Cys Leu
1               5

<210> SEQ ID NO 96
<211> LENGTH: 10
<212> TYPE: PRT
<213> ORGANISM: Hepatitis B virus

<400> SEQUENCE: 96

Ile Leu Ser Thr Leu Pro Glu Thr Thr Val
1               5                   10

<210> SEQ ID NO 97
<211> LENGTH: 20
<212> TYPE: PRT
<213> ORGANISM: Hepatitis B virus

<400> SEQUENCE: 97

Asn Cys Thr Cys Ile Pro Ile Pro Ser Ser Tyr Ala Phe Gly Lys Phe
1               5                   10                  15

Leu Thr Gly Tyr
            20

<210> SEQ ID NO 98
<211> LENGTH: 20
<212> TYPE: PRT
<213> ORGANISM: Hepatitis B virus

<400> SEQUENCE: 98

Ala Ser Ala Arg Phe Ser Tyr Leu Ser Leu Leu Val Pro Phe Val Gly
1               5                   10                  15

Tyr Phe Val Gly
            20

<210> SEQ ID NO 99
<211> LENGTH: 20
<212> TYPE: PRT
<213> ORGANISM: Hepatitis B virus

<400> SEQUENCE: 99

Leu Ser Pro Thr Val Tyr Leu Ser Val Ile Tyr Met Met Tyr Tyr Tyr
1               5                   10                  15

Gly Pro Ser Leu
            20

<210> SEQ ID NO 100
<211> LENGTH: 19
<212> TYPE: PRT
<213> ORGANISM: Hepatitis B virus

```
<400> SEQUENCE: 100

Thr Asn Met Gly Leu Lys Phe Arg Leu Leu Tyr Phe His Ile Ser Cys
1               5                   10                  15

Leu Tyr Phe

<210> SEQ ID NO 101
<211> LENGTH: 14
<212> TYPE: PRT
<213> ORGANISM: Influenza A virus

<400> SEQUENCE: 101

Ala Ala Phe Glu Asp Leu Arg Val Leu Ser Phe Ile Arg Gly
1               5                   10

<210> SEQ ID NO 102
<211> LENGTH: 34
<212> TYPE: PRT
<213> ORGANISM: Influenza A virus

<400> SEQUENCE: 102

Ala Gly Phe Ile Glu Asn Gly Trp Glu Gly Met Val Asp Gly Trp Tyr
1               5                   10                  15

Gly Phe Arg His Gln Asn Ser Glu Gly Thr Gly Gln Ala Ala Asp Leu
            20                  25                  30

Lys Ser

<210> SEQ ID NO 103
<211> LENGTH: 9
<212> TYPE: PRT
<213> ORGANISM: Influenza A virus

<400> SEQUENCE: 103

Ala Ile Met Asp Lys Asn Ile Ile Leu
1               5

<210> SEQ ID NO 104
<211> LENGTH: 8
<212> TYPE: PRT
<213> ORGANISM: Influenza A virus

<400> SEQUENCE: 104

Ala Ser Cys Met Gly Leu Ile Tyr
1               5

<210> SEQ ID NO 105
<211> LENGTH: 16
<212> TYPE: PRT
<213> ORGANISM: Influenza A virus

<400> SEQUENCE: 105

Ala Ser Gly Arg Val Thr Val Ser Thr Lys Arg Ser Gln Gln Thr Val
1               5                   10                  15

<210> SEQ ID NO 106
<211> LENGTH: 23
<212> TYPE: PRT
<213> ORGANISM: Influenza A virus

<400> SEQUENCE: 106

Ala Ser Gln Gly Thr Lys Arg Ser Tyr Glu Gln Met Glu Thr Asp Gly
1               5                   10                  15

Glu Arg Gln Asn Ala Thr Glu
```

```
                    20

<210> SEQ ID NO 107
<211> LENGTH: 32
<212> TYPE: PRT
<213> ORGANISM: Influenza A virus

<400> SEQUENCE: 107

Ala Thr Gly Met Arg Asn Val Pro Glu Lys Gln Thr Arg Gly Ile Phe
1               5                   10                  15

Gly Ala Ile Ala Gly Phe Ile Glu Asn Gly Trp Glu Gly Met Val Asp
            20                  25                  30

<210> SEQ ID NO 108
<211> LENGTH: 9
<212> TYPE: PRT
<213> ORGANISM: Influenza A virus

<400> SEQUENCE: 108

Cys Thr Glu Leu Lys Leu Ser Asp Tyr
1               5

<210> SEQ ID NO 109
<211> LENGTH: 9
<212> TYPE: PRT
<213> ORGANISM: Influenza A virus

<400> SEQUENCE: 109

Cys Val Asn Gly Ser Cys Phe Thr Val
1               5

<210> SEQ ID NO 110
<211> LENGTH: 16
<212> TYPE: PRT
<213> ORGANISM: Influenza A virus

<400> SEQUENCE: 110

Cys Tyr Pro Tyr Asp Val Pro Asp Tyr Ala Ser Leu Arg Ser Leu Val
1               5                   10                  15

<210> SEQ ID NO 111
<211> LENGTH: 19
<212> TYPE: PRT
<213> ORGANISM: Influenza A virus

<400> SEQUENCE: 111

Cys Tyr Pro Tyr Asp Val Pro Asp Tyr Ala Ser Leu Arg Ser Leu Val
1               5                   10                  15

Ala Ser Ser

<210> SEQ ID NO 112
<211> LENGTH: 32
<212> TYPE: PRT
<213> ORGANISM: Influenza A virus

<400> SEQUENCE: 112

Cys Tyr Pro Tyr Asp Val Pro Asp Tyr Ala Ser Leu Arg Ser Leu Val
1               5                   10                  15

Ala Ser Ser Gly Thr Leu Glu Phe Ile Asn Glu Asp Phe Asn Trp Thr
            20                  25                  30

<210> SEQ ID NO 113
<211> LENGTH: 14
```

```
<212> TYPE: PRT
<213> ORGANISM: Influenza A virus

<400> SEQUENCE: 113

Asp Pro Arg Met Cys Ser Leu Met Gln Gly Ser Thr Leu Pro
1 5 10

<210> SEQ ID NO 114
<211> LENGTH: 36
<212> TYPE: PRT
<213> ORGANISM: Influenza A virus

<400> SEQUENCE: 114

Asp Tyr Ala Ser Leu Arg Ser Leu Val Ala Ser Ser Gly Thr Leu Glu
1 5 10 15

Phe Ile Asn Glu Gly Phe Asn Trp Thr Gly Val Thr Gln Asn Gly Gly
20 25 30

Ser Ser Ala Cys
35

<210> SEQ ID NO 115
<211> LENGTH: 11
<212> TYPE: PRT
<213> ORGANISM: Influenza A virus

<400> SEQUENCE: 115

Glu Asp Leu Thr Phe Leu Ala Arg Ser Ala Leu
1 5 10

<210> SEQ ID NO 116
<211> LENGTH: 9
<212> TYPE: PRT
<213> ORGANISM: Influenza A virus

<400> SEQUENCE: 116

Glu Leu Arg Ser Arg Tyr Trp Ala Ile
1 5

<210> SEQ ID NO 117
<211> LENGTH: 36
<212> TYPE: PRT
<213> ORGANISM: Influenza A virus

<400> SEQUENCE: 117

Glu Asn Gln His Thr Ile Asp Leu Thr Asp Ser Glu Met Asn Lys Leu
1 5 10 15

Phe Glu Lys Thr Arg Lys Gln Leu Arg Glu Asn Ala Glu Asp Met Gly
20 25 30

Asn Gly Cys Phe
35

<210> SEQ ID NO 118
<211> LENGTH: 8
<212> TYPE: PRT
<213> ORGANISM: Influenza A virus

<400> SEQUENCE: 118

Phe Glu Asp Leu Arg Val Leu Ser
1 5

<210> SEQ ID NO 119
<211> LENGTH: 9
<212> TYPE: PRT

<213> ORGANISM: Influenza A virus

<400> SEQUENCE: 119

Gly Ile Leu Gly Phe Val Phe Thr Leu
1 5

<210> SEQ ID NO 120
<211> LENGTH: 10
<212> TYPE: PRT
<213> ORGANISM: Influenza A virus

<400> SEQUENCE: 120

Gly Ile Leu Gly Phe Val Phe Thr Leu Thr
1 5 10

<210> SEQ ID NO 121
<211> LENGTH: 11
<212> TYPE: PRT
<213> ORGANISM: Influenza A virus

<400> SEQUENCE: 121

Gly Ile Leu Gly Phe Val Phe Thr Leu Thr Val
1 5 10

<210> SEQ ID NO 122
<211> LENGTH: 20
<212> TYPE: PRT
<213> ORGANISM: Influenza A virus

<400> SEQUENCE: 122

Gly Lys Asn Thr Asp Leu Glu Val Leu Met Glu Trp Leu Lys Thr Arg
1 5 10 15

Pro Ile Leu Ser
20

<210> SEQ ID NO 123
<211> LENGTH: 35
<212> TYPE: PRT
<213> ORGANISM: Influenza A virus

<400> SEQUENCE: 123

His His Pro Ser Thr Asp Arg Asp Gln Thr Ser Leu Tyr Val Arg Ala
1 5 10 15

Ser Gly Arg Val Thr Val Ser Thr Lys Arg Ser Gln Gln Thr Val Thr
20 25 30

Pro Asn Ile
35

<210> SEQ ID NO 124
<211> LENGTH: 12
<212> TYPE: PRT
<213> ORGANISM: Influenza A virus

<400> SEQUENCE: 124

Lys Gly Ile Leu Gly Phe Val Phe Thr Leu Thr Val
1 5 10

<210> SEQ ID NO 125
<211> LENGTH: 14
<212> TYPE: PRT
<213> ORGANISM: Influenza A virus

<400> SEQUENCE: 125

-continued

Lys Leu Ser Thr Arg Gly Val Gln Ile Ala Ser Asn Glu Asn
1               5                   10

<210> SEQ ID NO 126
<211> LENGTH: 20
<212> TYPE: PRT
<213> ORGANISM: Influenza A virus

<400> SEQUENCE: 126

Leu Lys Gly Lys Phe Gln Thr Ala Ala Gln Arg Ala Met Met Asp Gln
1               5                   10                  15

Val Arg Glu Ser
            20

<210> SEQ ID NO 127
<211> LENGTH: 14
<212> TYPE: PRT
<213> ORGANISM: Influenza A virus

<400> SEQUENCE: 127

Leu Pro Arg Arg Ser Gly Ala Ala Gly Ala Ala Val Lys Gly
1               5                   10

<210> SEQ ID NO 128
<211> LENGTH: 22
<212> TYPE: PRT
<213> ORGANISM: Influenza A virus

<400> SEQUENCE: 128

Leu Arg Val Leu Ser Phe Ile Arg Gly Thr Lys Val Ser Pro Arg Gly
1               5                   10                  15

Lys Leu Ser Thr Arg Gly
            20

<210> SEQ ID NO 129
<211> LENGTH: 19
<212> TYPE: PRT
<213> ORGANISM: Influenza A virus

<400> SEQUENCE: 129

Leu Thr Lys Gly Ile Leu Gly Phe Val Phe Thr Leu Thr Val Pro Ser
1               5                   10                  15

Glu Arg Gly

<210> SEQ ID NO 130
<211> LENGTH: 22
<212> TYPE: PRT
<213> ORGANISM: Influenza A virus

<400> SEQUENCE: 130

Pro Ser Phe Asp Met Ser Asn Glu Gly Ser Tyr Phe Phe Gly Asp Asn
1               5                   10                  15

Ala Glu Glu Tyr Asp Asn
            20

<210> SEQ ID NO 131
<211> LENGTH: 17
<212> TYPE: PRT
<213> ORGANISM: Influenza A virus

<400> SEQUENCE: 131

Arg Gly Leu Gln Arg Arg Arg Phe Val Gln Asn Ala Leu Asn Gly Asn
1               5                   10                  15

Gly

<210> SEQ ID NO 132
<211> LENGTH: 11
<212> TYPE: PRT
<213> ORGANISM: Influenza A virus

<400> SEQUENCE: 132

Arg Arg Ser Gly Ala Ala Gly Ala Ala Val Lys
1               5                   10

<210> SEQ ID NO 133
<211> LENGTH: 8
<212> TYPE: PRT
<213> ORGANISM: Influenza A virus

<400> SEQUENCE: 133

Arg Tyr Trp Ala Ile Arg Thr Arg
1               5

<210> SEQ ID NO 134
<211> LENGTH: 9
<212> TYPE: PRT
<213> ORGANISM: Influenza A virus

<400> SEQUENCE: 134

Ser Arg Tyr Trp Ala Ile Arg Thr Arg
1               5

<210> SEQ ID NO 135
<211> LENGTH: 9
<212> TYPE: PRT
<213> ORGANISM: Influenza A virus

<400> SEQUENCE: 135

Val Ser Asp Gly Gly Pro Asn Leu Tyr
1               5

<210> SEQ ID NO 136
<211> LENGTH: 9
<212> TYPE: PRT
<213> ORGANISM: Influenza A virus

<400> SEQUENCE: 136

Phe Met Tyr Ser Asp Phe His Phe Ile
1               5

<210> SEQ ID NO 137
<211> LENGTH: 10
<212> TYPE: PRT
<213> ORGANISM: Influenza A virus

<400> SEQUENCE: 137

Ile Leu Gly Phe Val Phe Thr Leu Thr Val
1               5                   10

<210> SEQ ID NO 138
<211> LENGTH: 9
<212> TYPE: PRT
<213> ORGANISM: Influenza A virus

<400> SEQUENCE: 138

Asn Met Leu Ser Thr Val Leu Gly Val
1               5

<210> SEQ ID NO 139
<211> LENGTH: 10
<212> TYPE: PRT
<213> ORGANISM: Influenza A virus

<400> SEQUENCE: 139

Arg Met Val Leu Ala Ser Thr Thr Ala Lys
1               5                   10

<210> SEQ ID NO 140
<211> LENGTH: 9
<212> TYPE: PRT
<213> ORGANISM: Influenza A virus

<400> SEQUENCE: 140

Ser Ile Ile Pro Ser Gly Pro Leu Lys
1               5

<210> SEQ ID NO 141
<211> LENGTH: 9
<212> TYPE: PRT
<213> ORGANISM: Influenza A virus

<400> SEQUENCE: 141

Ser Leu Glu Asn Phe Arg Ala Tyr Val
1               5

<210> SEQ ID NO 142
<211> LENGTH: 20
<212> TYPE: PRT
<213> ORGANISM: Influenza A virus

<400> SEQUENCE: 142

Leu Thr Lys Gly Ile Leu Gly Phe Val Phe Thr Leu Thr Val Pro Ser
1               5                   10                  15

Glu Arg Gly Leu
            20

<210> SEQ ID NO 143
<211> LENGTH: 9
<212> TYPE: PRT
<213> ORGANISM: Epstein Barr virus

<400> SEQUENCE: 143

Gly Leu Cys Thr Leu Val Ala Met Leu
1               5

<210> SEQ ID NO 144
<211> LENGTH: 14
<212> TYPE: PRT
<213> ORGANISM: Human cytomegalovirus

<400> SEQUENCE: 144

Ala Arg Asn Leu Val Pro Met Val Ala Thr Val Gln Gly Gln
1               5                   10

<210> SEQ ID NO 145
<211> LENGTH: 15
<212> TYPE: PRT
<213> ORGANISM: Human cytomegalovirus

<400> SEQUENCE: 145

Arg Lys Thr Pro Arg Val Thr Gly Gly Gly Ala Met Ala Gly Ala

-continued

<210> SEQ ID NO 146
<211> LENGTH: 15
<212> TYPE: PRT
<213> ORGANISM: Human cytomegalovirus

<400> SEQUENCE: 146

Gln Glu Phe Phe Trp Asp Ala Asn Asp Ile Tyr Arg Ile Phe Ala
1               5                   10                  15

<210> SEQ ID NO 147
<211> LENGTH: 15
<212> TYPE: PRT
<213> ORGANISM: Human cytomegalovirus

<400> SEQUENCE: 147

Ala Arg Asn Leu Val Pro Met Val Ala Thr Val Gln Gly Gln Asn
1               5                   10                  15

<210> SEQ ID NO 148
<211> LENGTH: 12
<212> TYPE: PRT
<213> ORGANISM: Human cytomegalovirus

<400> SEQUENCE: 148

Tyr Tyr Thr Ser Ala Phe Val Phe Pro Thr Lys Asp
1               5                   10

<210> SEQ ID NO 149
<211> LENGTH: 11
<212> TYPE: PRT
<213> ORGANISM: Human cytomegalovirus

<400> SEQUENCE: 149

Val Phe Pro Thr Lys Asp Val Ala Leu Arg His
1               5                   10

<210> SEQ ID NO 150
<211> LENGTH: 15
<212> TYPE: PRT
<213> ORGANISM: Human cytomegalovirus

<400> SEQUENCE: 150

Asp Asp Val Trp Thr Ser Gly Ser Asp Ser Asp Glu Glu Leu Val
1               5                   10                  15

<210> SEQ ID NO 151
<211> LENGTH: 9
<212> TYPE: PRT
<213> ORGANISM: Human cytomegalovirus

<400> SEQUENCE: 151

Asn Leu Val Pro Met Val Ala Thr Val
1               5

<210> SEQ ID NO 152
<211> LENGTH: 18
<212> TYPE: PRT
<213> ORGANISM: Polio virus

<400> SEQUENCE: 152

Val Ala Ile Ile Glu Val Asp Asn Glu Gln Pro Thr Thr Arg Ala Gln
1               5                   10                  15

Lys Leu

<210> SEQ ID NO 153
<211> LENGTH: 18
<212> TYPE: PRT
<213> ORGANISM: Polio virus

<400> SEQUENCE: 153

Thr Arg Ala Gln Lys Leu Phe Ala Met Trp Arg Ile Thr Tyr Lys Asp
1 5 10 15

Thr Val

<210> SEQ ID NO 154
<211> LENGTH: 39
<212> TYPE: PRT
<213> ORGANISM: Polio virus

<400> SEQUENCE: 154

Gly Ala Cys Val Ala Ile Ile Glu Val Asp Asn Glu Gln Pro Thr Thr
1 5 10 15

Arg Ala Gln Lys Leu Phe Ala Met Trp Arg Ile Thr Tyr Lys Asp Thr
20 25 30

Val Gln Leu Arg Arg Lys Leu
35

<210> SEQ ID NO 155
<211> LENGTH: 11
<212> TYPE: PRT
<213> ORGANISM: Epstein Barr virus

<400> SEQUENCE: 155

His Pro Val Gly Glu Ala Asp Tyr Phe Glu Tyr
1 5 10

<210> SEQ ID NO 156
<211> LENGTH: 10
<212> TYPE: PRT
<213> ORGANISM: Epstein Barr virus

<400> SEQUENCE: 156

Asp Thr Pro Leu Ile Pro Leu Thr Ile Phe
1 5 10

<210> SEQ ID NO 157
<211> LENGTH: 9
<212> TYPE: PRT
<213> ORGANISM: Epstein Barr virus

<400> SEQUENCE: 157

Gln Ala Lys Trp Arg Leu Gln Thr Leu
1 5

<210> SEQ ID NO 158
<211> LENGTH: 9
<212> TYPE: PRT
<213> ORGANISM: Epstein Barr virus

<400> SEQUENCE: 158

Ala Tyr Ser Ser Trp Met Tyr Ser Tyr
1 5

<210> SEQ ID NO 159
<211> LENGTH: 8

```
<212> TYPE: PRT
<213> ORGANISM: Epstein Barr virus

<400> SEQUENCE: 159

Arg Tyr Ser Ile Phe Phe Asp Tyr
1               5

<210> SEQ ID NO 160
<211> LENGTH: 9
<212> TYPE: PRT
<213> ORGANISM: Epstein Barr virus

<400> SEQUENCE: 160

Phe Leu Arg Gly Arg Ala Tyr Gly Leu
1               5

<210> SEQ ID NO 161
<211> LENGTH: 9
<212> TYPE: PRT
<213> ORGANISM: Epstein Barr virus

<400> SEQUENCE: 161

Arg Pro Pro Ile Phe Ile Arg Arg Leu
1               5

<210> SEQ ID NO 162
<211> LENGTH: 9
<212> TYPE: PRT
<213> ORGANISM: Epstein Barr virus

<400> SEQUENCE: 162

Leu Glu Lys Ala Arg Gly Ser Thr Tyr
1               5

<210> SEQ ID NO 163
<211> LENGTH: 9
<212> TYPE: PRT
<213> ORGANISM: Epstein Barr virus

<400> SEQUENCE: 163

His Leu Ala Ala Gln Gly Met Ala Tyr
1               5

<210> SEQ ID NO 164
<211> LENGTH: 9
<212> TYPE: PRT
<213> ORGANISM: Epstein Barr virus

<400> SEQUENCE: 164

Tyr Pro Leu His Glu Gln His Gly Met
1               5

<210> SEQ ID NO 165
<211> LENGTH: 9
<212> TYPE: PRT
<213> ORGANISM: Epstein Barr virus

<400> SEQUENCE: 165

Val Phe Ser Asp Gly Arg Val Ala Cys
1               5

<210> SEQ ID NO 166
<211> LENGTH: 9
<212> TYPE: PRT
<213> ORGANISM: Epstein Barr virus
```

-continued

```
<400> SEQUENCE: 166

Val Pro Ala Pro Ala Gly Pro Ile Val
1               5

<210> SEQ ID NO 167
<211> LENGTH: 9
<212> TYPE: PRT
<213> ORGANISM: Epstein Barr virus

<400> SEQUENCE: 167

Ser Val Arg Asp Arg Leu Ala Arg Leu
1               5

<210> SEQ ID NO 168
<211> LENGTH: 9
<212> TYPE: PRT
<213> ORGANISM: Epstein Barr virus

<400> SEQUENCE: 168

Arg Leu Arg Ala Glu Ala Gln Val Lys
1               5

<210> SEQ ID NO 169
<211> LENGTH: 15
<212> TYPE: PRT
<213> ORGANISM: Epstein Barr virus

<400> SEQUENCE: 169

Asn Pro Thr Gln Ala Pro Val Ile Gln Leu Val His Ala Val Tyr
1               5                   10                  15

<210> SEQ ID NO 170
<211> LENGTH: 9
<212> TYPE: PRT
<213> ORGANISM: Epstein Barr virus

<400> SEQUENCE: 170

His Arg Cys Gln Ala Ile Arg Lys Lys
1               5

<210> SEQ ID NO 171
<211> LENGTH: 9
<212> TYPE: PRT
<213> ORGANISM: Epstein Barr virus

<400> SEQUENCE: 171

Thr Tyr Ser Ala Gly Ile Val Gln Ile
1               5

<210> SEQ ID NO 172
<211> LENGTH: 11
<212> TYPE: PRT
<213> ORGANISM: Epstein Barr virus

<400> SEQUENCE: 172

Arg Arg Ala Arg Ser Leu Ser Ala Glu Arg Tyr
1               5                   10

<210> SEQ ID NO 173
<211> LENGTH: 10
<212> TYPE: PRT
<213> ORGANISM: Epstein Barr virus

<400> SEQUENCE: 173
```

Ala Val Phe Asp Arg Lys Ser Asp Ala Lys
1               5                   10

<210> SEQ ID NO 174
<211> LENGTH: 9
<212> TYPE: PRT
<213> ORGANISM: Epstein Barr virus

<400> SEQUENCE: 174

Ile Val Thr Asp Phe Ser Val Ile Lys
1               5

<210> SEQ ID NO 175
<211> LENGTH: 15
<212> TYPE: PRT
<213> ORGANISM: Epstein Barr virus

<400> SEQUENCE: 175

Leu Pro Gly Pro Gln Val Thr Ala Val Leu Leu His Glu Glu Ser
1               5                   10                  15

<210> SEQ ID NO 176
<211> LENGTH: 9
<212> TYPE: PRT
<213> ORGANISM: Epstein Barr virus

<400> SEQUENCE: 176

Ala Val Leu Leu His Glu Glu Ser Met
1               5

<210> SEQ ID NO 177
<211> LENGTH: 14
<212> TYPE: PRT
<213> ORGANISM: Epstein Barr virus

<400> SEQUENCE: 177

Asp Glu Pro Ala Ser Thr Glu Pro Val His Asp Gln Leu Leu
1               5                   10

<210> SEQ ID NO 178
<211> LENGTH: 10
<212> TYPE: PRT
<213> ORGANISM: Epstein Barr virus

<400> SEQUENCE: 178

Val Glu Ile Thr Pro Tyr Lys Pro Thr Trp
1               5                   10

<210> SEQ ID NO 179
<211> LENGTH: 9
<212> TYPE: PRT
<213> ORGANISM: Epstein Barr virus

<400> SEQUENCE: 179

Gly Gln Gly Gly Ser Pro Thr Ala Met
1               5

<210> SEQ ID NO 180
<211> LENGTH: 9
<212> TYPE: PRT
<213> ORGANISM: Epstein Barr virus

<400> SEQUENCE: 180

Glu Gly Gly Val Gly Trp Arg His Trp

<210> SEQ ID NO 181
<211> LENGTH: 10
<212> TYPE: PRT
<213> ORGANISM: Epstein Barr virus

<400> SEQUENCE: 181

Gln Asn Gly Ala Leu Ala Ile Asn Thr Phe
1               5                   10

<210> SEQ ID NO 182
<211> LENGTH: 10
<212> TYPE: PRT
<213> ORGANISM: Epstein Barr virus

<400> SEQUENCE: 182

Leu Arg Gly Lys Trp Gln Arg Arg Tyr Arg
1               5                   10

<210> SEQ ID NO 183
<211> LENGTH: 9
<212> TYPE: PRT
<213> ORGANISM: Epstein Barr virus

<400> SEQUENCE: 183

Arg Arg Ile Tyr Asp Leu Ile Glu Leu
1               5

<210> SEQ ID NO 184
<211> LENGTH: 8
<212> TYPE: PRT
<213> ORGANISM: Epstein Barr virus

<400> SEQUENCE: 184

His His Ile Trp Gln Asn Leu Leu
1               5

<210> SEQ ID NO 185
<211> LENGTH: 10
<212> TYPE: PRT
<213> ORGANISM: Epstein Barr virus

<400> SEQUENCE: 185

Glu Glu Asn Leu Leu Asp Phe Val Arg Phe
1               5                   10

<210> SEQ ID NO 186
<211> LENGTH: 10
<212> TYPE: PRT
<213> ORGANISM: Epstein Barr virus

<400> SEQUENCE: 186

Leu Leu Asp Phe Val Arg Phe Met Gly Val
1               5                   10

<210> SEQ ID NO 187
<211> LENGTH: 9
<212> TYPE: PRT
<213> ORGANISM: Epstein Barr virus

<400> SEQUENCE: 187

Lys Glu His Val Ile Gln Asn Ala Phe
1               5

```
<210> SEQ ID NO 188
<211> LENGTH: 9
<212> TYPE: PRT
<213> ORGANISM: Epstein Barr virus

<400> SEQUENCE: 188

Phe Arg Lys Ala Gln Ile Gln Gly Leu
1               5

<210> SEQ ID NO 189
<211> LENGTH: 9
<212> TYPE: PRT
<213> ORGANISM: Epstein Barr virus

<400> SEQUENCE: 189

Gln Pro Arg Ala Pro Ile Arg Pro Ile
1               5

<210> SEQ ID NO 190
<211> LENGTH: 9
<212> TYPE: PRT
<213> ORGANISM: Epstein Barr virus

<400> SEQUENCE: 190

Pro Tyr Leu Phe Trp Leu Ala Ala Ile
1               5

<210> SEQ ID NO 191
<211> LENGTH: 9
<212> TYPE: PRT
<213> ORGANISM: Epstein Barr virus

<400> SEQUENCE: 191

Ile Glu Asp Pro Pro Phe Asn Ser Leu
1               5

<210> SEQ ID NO 192
<211> LENGTH: 9
<212> TYPE: PRT
<213> ORGANISM: Epstein Barr virus

<400> SEQUENCE: 192

Arg Arg Arg Trp Arg Arg Leu Thr Val
1               5

<210> SEQ ID NO 193
<211> LENGTH: 9
<212> TYPE: PRT
<213> ORGANISM: Epstein Barr virus

<400> SEQUENCE: 193

Leu Leu Trp Thr Leu Val Val Leu Leu
1               5

<210> SEQ ID NO 194
<211> LENGTH: 11
<212> TYPE: PRT
<213> ORGANISM: Epstein Barr virus

<400> SEQUENCE: 194

Ser Ser Cys Ser Ser Cys Pro Leu Ser Lys Ile
1               5                   10

<210> SEQ ID NO 195
```

```
<211> LENGTH: 9
<212> TYPE: PRT
<213> ORGANISM: Epstein Barr virus

<400> SEQUENCE: 195

Thr Tyr Gly Pro Val Phe Met Cys Leu
1               5

<210> SEQ ID NO 196
<211> LENGTH: 9
<212> TYPE: PRT
<213> ORGANISM: Epstein Barr virus

<400> SEQUENCE: 196

Cys Leu Gly Gly Leu Leu Thr Met Val
1               5

<210> SEQ ID NO 197
<211> LENGTH: 10
<212> TYPE: PRT
<213> ORGANISM: Epstein Barr virus

<400> SEQUENCE: 197

Val Met Ser Asn Thr Leu Leu Ser Ala Trp
1               5                   10

<210> SEQ ID NO 198
<211> LENGTH: 9
<212> TYPE: PRT
<213> ORGANISM: Epstein Barr virus

<400> SEQUENCE: 198

Leu Thr Ala Gly Phe Leu Ile Phe Leu
1               5

<210> SEQ ID NO 199
<211> LENGTH: 8
<212> TYPE: PRT
<213> ORGANISM: Epstein Barr virus

<400> SEQUENCE: 199

Arg Ala Lys Phe Lys Gln Leu Leu
1               5

<210> SEQ ID NO 200
<211> LENGTH: 16
<212> TYPE: PRT
<213> ORGANISM: Epstein Barr virus

<400> SEQUENCE: 200

Arg Lys Cys Cys Arg Ala Lys Phe Lys Gln Leu Leu Gln His Tyr Arg
1               5                   10                  15

<210> SEQ ID NO 201
<211> LENGTH: 9
<212> TYPE: PRT
<213> ORGANISM: Epstein Barr virus

<400> SEQUENCE: 201

Lys Asp Thr Trp Leu Asp Ala Arg Met
1               5

<210> SEQ ID NO 202
<211> LENGTH: 9
<212> TYPE: PRT
```

<213> ORGANISM: Epstein Barr virus

<400> SEQUENCE: 202

Asp Glu Val Glu Phe Leu Gly His Tyr
1               5

<210> SEQ ID NO 203
<211> LENGTH: 15
<212> TYPE: PRT
<213> ORGANISM: Epstein Barr virus

<400> SEQUENCE: 203

Phe Arg Asn Leu Ala Tyr Gly Arg Thr Cys Val Leu Gly Lys Glu
1               5                   10                  15

<210> SEQ ID NO 204
<211> LENGTH: 9
<212> TYPE: PRT
<213> ORGANISM: Epstein Barr virus

<400> SEQUENCE: 204

Tyr Arg Ser Gly Ile Ile Ala Val Val
1               5

<210> SEQ ID NO 205
<211> LENGTH: 505
<212> TYPE: PRT
<213> ORGANISM: Human papillomavirus

<400> SEQUENCE: 205

Met Ser Leu Trp Leu Pro Ser Glu Ala Thr Val Tyr Leu Pro Pro Val
1               5                   10                  15

Pro Val Ser Lys Val Val Ser Thr Asp Glu Tyr Val Ala Arg Thr Asn
                20                  25                  30

Ile Tyr Tyr His Ala Gly Thr Ser Arg Leu Leu Ala Val Gly His Pro
            35                  40                  45

Tyr Phe Pro Ile Lys Lys Pro Asn Asn Asn Lys Ile Leu Val Pro Lys
    50                  55                  60

Val Ser Gly Leu Gln Tyr Arg Val Phe Arg Ile His Leu Pro Asp Pro
65                  70                  75                  80

Asn Lys Phe Gly Phe Pro Asp Thr Ser Phe Tyr Asn Pro Asp Thr Gln
                85                  90                  95

Arg Leu Val Trp Ala Cys Val Gly Val Glu Val Gly Arg Gly Gln Pro
            100                 105                 110

Leu Gly Val Gly Ile Ser Gly His Pro Leu Leu Asn Lys Leu Asp Asp
        115                 120                 125

Thr Glu Asn Ala Ser Ala Tyr Ala Ala Asn Ala Gly Val Asp Asn Arg
    130                 135                 140

Glu Cys Ile Ser Met Asp Tyr Lys Gln Thr Gln Leu Cys Leu Ile Gly
145                 150                 155                 160

Cys Lys Pro Pro Ile Gly Glu His Trp Gly Lys Gly Ser Pro Cys Thr
                165                 170                 175

Asn Val Ala Val Asn Pro Gly Asp Cys Pro Pro Leu Glu Leu Ile Asn
            180                 185                 190

Thr Val Ile Gln Asp Gly Asp Met Val Asp Thr Gly Phe Gly Ala Met
        195                 200                 205

Asp Phe Thr Thr Leu Gln Ala Asn Lys Ser Glu Val Pro Leu Asp Ile
    210                 215                 220

```
Cys Thr Ser Ile Cys Lys Tyr Pro Asp Tyr Ile Lys Met Val Ser Glu
225                 230                 235                 240

Pro Tyr Gly Asp Ser Leu Phe Phe Tyr Leu Arg Arg Glu Gln Met Phe
            245                 250                 255

Val Arg His Leu Phe Asn Arg Ala Gly Thr Val Gly Glu Asn Val Pro
            260                 265                 270

Asp Asp Leu Tyr Ile Lys Gly Ser Gly Ser Thr Ala Asn Leu Ala Ser
            275                 280                 285

Ser Asn Tyr Phe Pro Thr Pro Ser Gly Ser Met Val Thr Ser Asp Ala
            290                 295                 300

Gln Ile Phe Asn Lys Pro Tyr Trp Leu Gln Arg Ala Gln Gly His Asn
305                 310                 315                 320

Asn Gly Ile Cys Trp Gly Asn Gln Leu Phe Val Thr Val Val Asp Thr
                325                 330                 335

Thr Arg Ser Thr Asn Met Ser Leu Cys Ala Ala Ile Ser Thr Ser Glu
            340                 345                 350

Thr Thr Tyr Lys Asn Thr Asn Phe Lys Glu Tyr Leu Arg His Gly Glu
            355                 360                 365

Glu Tyr Asp Leu Gln Phe Ile Phe Gln Leu Cys Lys Ile Thr Leu Thr
370                 375                 380

Ala Asp Val Met Thr Tyr Ile His Ser Met Asn Ser Thr Ile Leu Glu
385                 390                 395                 400

Asp Trp Asn Phe Gly Leu Gln Pro Pro Gly Gly Thr Leu Glu Asp
                405                 410                 415

Thr Tyr Arg Phe Val Thr Ser Gln Ala Ile Ala Cys Gln Lys His Thr
            420                 425                 430

Pro Pro Ala Pro Lys Glu Asp Pro Leu Lys Lys Tyr Thr Phe Trp Glu
            435                 440                 445

Val Asn Leu Lys Glu Lys Phe Ser Ala Asp Leu Asp Gln Phe Pro Leu
            450                 455                 460

Gly Arg Lys Phe Leu Leu Gln Ala Gly Leu Lys Ala Lys Pro Lys Phe
465                 470                 475                 480

Thr Leu Gly Lys Arg Lys Ala Thr Pro Thr Thr Ser Ser Thr Ser Thr
            485                 490                 495

Thr Ala Lys Arg Lys Lys Arg Lys Leu
            500                 505
```

<210> SEQ ID NO 206
<211> LENGTH: 1518
<212> TYPE: DNA
<213> ORGANISM: Human papillomavirus

<400> SEQUENCE: 206

```
atgtctcttt ggctgcctag tgaggccact gtctacttgc ctcctgtccc agtatctaag      60
gttgtaagca cggatgaata tgttgcacgc acaaacatat attatcatgc aggaacatcc     120
agactacttg cagttggaca tccctatttt cctattaaaa acctaacaa taacaaaata      180
ttagttccta agtatcagg attacaatac agggtattta gaatacattt acctgacccc     240
aataagtttg gttttcctga cacctcattt tataatccag atacacagcg gctggtttgg     300
gcctgtgtag gtgttgaggt aggtcgtggt cagccattag gtgtgggcat tagtggccat     360
cctttattaa ataaattgga tgacacagaa aatgctagtg cttatgcagc aaatgcaggt     420
gtggataata gagaatgtat atctatggat tacaaacaaa cacaattgtg tttaattggt     480
tgcaaaccac ctataggga acactgggc aaaggatccc catgtaccaa tgttgcagta     540
```

-continued

```
aatccaggtg attgtccacc attagagtta ataaacacag ttattcagga tggtgatatg    600
gttgatactg gctttggtgc tatggacttt actacattac aggctaacaa aagtgaagtt    660
ccactggata tttgtacatc tatttgcaaa tatccagatt atattaaaat ggtgtcagaa    720
ccatatggcg acagcttatt tttttattta cgaagggaac aaatgtttgt tagacattta    780
tttaataggg ctggtactgt tggtgaaaat gtaccagacg atttatacat taaaggctct    840
gggtctactg caaatttagc cagttcaaat tattttccta cacctagtgg ttctatggtt    900
acctctgatg cccaaatatt caataaacct tattggttac aacgagcaca gggccacaat    960
aatggcattt gttggggtaa ccaactattt gttactgttg ttgatactac acgcagtaca   1020
aatatgtcat tatgtgctgc catatctact tcagaaacta catataaaaa tactaacttt   1080
aaggagtacc tacgacatgg ggaggaatat gatttacagt ttattttca actgtgcaaa    1140 ataaccttaa ctgcagacgt tatgacatac atacattcta tgaattccac tatttggag    1200 gactggaatt ttggtctaca acctccccca ggaggcacac tagaagatac ttataggttt   1260
gtaacatccc aggcaattgc ttgtcaaaaa catacacctc cagcacctaa agaagatccc   1320
cttaaaaaat acactttttg ggaagtaaat ttaaaggaaa agttttctgc agacctagat   1380
cagtttcctt taggacgcaa atttttacta caagcaggat tgaaggccaa accaaaattt   1440
acattaggaa acgaaaagc tacacccacc acctcatcta cctctacaac tgctaaacgc   1500
aaaaaacgta agctgtaa                                                  1518
```

<210> SEQ ID NO 207
<211> LENGTH: 473
<212> TYPE: PRT
<213> ORGANISM: Human papillomavirus

<400> SEQUENCE: 207

```
Met Arg His Lys Arg Ser Ala Lys Arg Thr Lys Arg Ala Ser Ala Thr
1               5                   10                  15

Gln Leu Tyr Lys Thr Cys Lys Gln Ala Gly Thr Cys Pro Pro Asp Ile
            20                  25                  30

Ile Pro Lys Val Glu Gly Lys Thr Ile Ala Asp Gln Ile Leu Gln Tyr
        35                  40                  45

Gly Ser Met Gly Val Phe Phe Gly Gly Leu Gly Ile Gly Thr Gly Ser
    50                  55                  60

Gly Thr Gly Gly Arg Thr Gly Tyr Ile Pro Leu Gly Thr Arg Pro Pro
65                  70                  75                  80

Thr Ala Thr Asp Thr Leu Ala Pro Val Arg Pro Pro Leu Thr Val Asp
                85                  90                  95

Pro Val Gly Pro Ser Asp Pro Ser Ile Val Ser Leu Val Glu Glu Thr
            100                 105                 110

Ser Phe Ile Asp Ala Gly Ala Pro Thr Ser Val Pro Ser Ile Pro Pro
        115                 120                 125

Asp Val Ser Gly Phe Ser Ile Thr Thr Ser Thr Asp Thr Thr Pro Ala
    130                 135                 140

Ile Leu Asp Ile Asn Asn Thr Val Thr Thr Val Thr Thr His Asn Asn
145                 150                 155                 160

Pro Thr Phe Thr Asp Pro Ser Val Leu Gln Pro Pro Thr Pro Ala Glu
                165                 170                 175

Thr Gly Gly His Phe Thr Leu Ser Ser Ser Thr Ile Ser Thr His Asn
            180                 185                 190
```

```
Tyr Glu Glu Ile Pro Met Asp Thr Phe Ile Val Ser Thr Asn Pro Asn
            195                 200                 205

Thr Val Thr Ser Ser Thr Pro Ile Pro Gly Ser Arg Pro Val Ala Arg
    210                 215                 220

Leu Gly Leu Tyr Ser Arg Thr Thr Gln Gln Val Lys Val Val Asp Pro
225                 230                 235                 240

Ala Phe Val Thr Thr Pro Thr Lys Leu Ile Thr Tyr Asp Asn Pro Ala
                245                 250                 255

Tyr Glu Gly Ile Asp Val Asp Asn Thr Leu Tyr Phe Ser Ser Asn Asp
            260                 265                 270

Asn Ser Ile Asn Ile Ala Pro Asp Pro Asp Phe Leu Asp Ile Val Ala
        275                 280                 285

Leu His Arg Pro Ala Leu Thr Ser Arg Arg Thr Gly Ile Arg Tyr Ser
290                 295                 300

Arg Ile Gly Asn Lys Gln Thr Leu Arg Thr Arg Ser Gly Lys Ser Ile
305                 310                 315                 320

Gly Ala Lys Val His Tyr Tyr Tyr Asp Phe Ser Thr Ile Asp Pro Ala
                325                 330                 335

Glu Glu Ile Glu Leu Gln Thr Ile Thr Pro Ser Thr Tyr Thr Thr Thr
            340                 345                 350

Ser His Ala Ala Ser Pro Thr Ser Ile Asn Asn Gly Leu Tyr Asp Ile
        355                 360                 365

Tyr Ala Asp Asp Phe Ile Thr Asp Thr Ser Thr Thr Pro Val Pro Ser
370                 375                 380

Val Pro Ser Thr Ser Leu Ser Gly Tyr Ile Pro Ala Asn Thr Thr Ile
385                 390                 395                 400

Pro Phe Gly Gly Ala Tyr Asn Ile Pro Leu Val Ser Gly Pro Asp Ile
                405                 410                 415

Pro Ile Asn Ile Thr Asp Gln Ala Pro Ser Leu Ile Pro Ile Val Pro
            420                 425                 430

Gly Ser Pro Gln Tyr Thr Ile Ile Ala Asp Ala Gly Asp Phe Tyr Leu
        435                 440                 445

His Pro Ser Tyr Tyr Met Leu Arg Lys Arg Arg Lys Arg Leu Pro Tyr
450                 455                 460

Phe Phe Ser Asp Val Ser Leu Ala Ala
465                 470
```

<210> SEQ ID NO 208
<211> LENGTH: 1416
<212> TYPE: DNA
<213> ORGANISM: Human papillomavirus

<400> SEQUENCE: 208

```
atgcgacaca aacgttctgc aaaacgcaca aaacgtgcat cggctaccca actttataaa      60
acatgcaaac aggcaggtac atgtccacct gacattatac ctaaggttga aggcaaaact     120
attgctgatc aaatattaca atatggaagt atgggtgtat tttttggtgg gttaggaatt     180
ggaacagggt cgggtacagg cggacgcact gggtatattc cattgggaac aaggcctccc     240
acagctacag atacacttgc tcctgtaaga cccccttta cagtagatcc tgtgggccct     300
tctgatcctt ctatagtttc tttagtggaa gaaactagtt ttattgatgc tggtgcacca     360
acatctgtac cttccattcc cccagatgta tcaggattta gtattactac ttcaactgat     420
accacacctg ctatattaga tattaataat actgttacta ctgttactac acataataat     480
cccactttca ctgacccatc tgtattgcag cctccaacac ctgcagaaac tggagggcat     540
```

```
tttacacttt catcatccac tattagtaca cataattatg aagaaattcc tatggataca    600
tttattgtta gcacaaaccc taacacagta actagtagca cacccatacc agggtctcgc    660
ccagtggcac gcctaggatt atatagtcgc acaacacaac aagttaaagt tgtagaccct    720
gcttttgtaa ccactcccac taaacttatt acatatgata atcctgcata tgaaggtata    780
gatgtggata atacattata tttttctagt aatgataata gtattaatat agctccagat    840
cctgactttt tggatatagt tgctttacat aggccagcat taacctctag gcgtactggc    900
ataaggtaca gtagaattgg taataaacaa acactacgta ctcgtagtgg aaaatctata    960
ggtgctaagg tacattatta ttatgatttt agtaccattg atcctgcaga agaaatagaa   1020
ttacaaacta taacaccttc tacatatact accacttcac atgcagcctc acctacttct   1080
attaataatg gattatatga tatttatgca gatgacttta ttacagatac ttctacaacc   1140
ccggtaccat ctgtaccctc tacatcttta tcaggttata ttcctgcaaa tacaacaatt   1200
ccttttggtg gtgcatacaa tattccttta gtatcaggtc ctgatatacc cattaatata   1260
actgaccaag ctccttcatt aattcctata gttccagggt ctccacaata tacaattatt   1320
gctgatgcag gtgacttta tttacatcct agtattaca tgttacgaaa acgacgtaaa    1380
cgtttaccat atttttttc agatgtctct ttggct                              1416
```

<210> SEQ ID NO 209
<211> LENGTH: 4
<212> TYPE: PRT
<213> ORGANISM: Unknown
<220> FEATURE:
<223> OTHER INFORMATION: Description of Unknown:
      Furin Cleavage site
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (3)..(3)
<223> OTHER INFORMATION: Arg or Lys

<400> SEQUENCE: 209

Arg Xaa Xaa Arg
1

<210> SEQ ID NO 210
<211> LENGTH: 4
<212> TYPE: PRT
<213> ORGANISM: Unknown
<220> FEATURE:
<223> OTHER INFORMATION: Description of Unknown:
      Furin Cleavage site

<400> SEQUENCE: 210

Arg Val Lys Arg
1

<210> SEQ ID NO 211
<211> LENGTH: 7
<212> TYPE: PRT
<213> ORGANISM: Unknown
<220> FEATURE:
<223> OTHER INFORMATION: Description of Unknown:
      MMP-cleavable peptide substrate
<220> FEATURE:
<221> NAME/KEY: MOD_RES
<222> LOCATION: (3)..(3)
<223> OTHER INFORMATION: Cit

```
<220> FEATURE:
<221> NAME/KEY: MOD_RES
<222> LOCATION: (5)..(5)
<223> OTHER INFORMATION: Hof

<400> SEQUENCE: 211

Glu Pro Xaa Gly Xaa Tyr Leu
1               5

<210> SEQ ID NO 212
<211> LENGTH: 8
<212> TYPE: PRT
<213> ORGANISM: Unknown
<220> FEATURE:
<223> OTHER INFORMATION: Description of Unknown:
      MMP-cleavable peptide substrate

<400> SEQUENCE: 212

Gly Pro Leu Gly Ile Ala Gly Gln
1               5

<210> SEQ ID NO 213
<211> LENGTH: 6
<212> TYPE: PRT
<213> ORGANISM: Unknown
<220> FEATURE:
<223> OTHER INFORMATION: Description of Unknown:
      MMP-cleavable peptide substrate

<400> SEQUENCE: 213

Pro Val Gly Leu Ile Gly
1               5

<210> SEQ ID NO 214
<211> LENGTH: 9
<212> TYPE: PRT
<213> ORGANISM: Unknown
<220> FEATURE:
<223> OTHER INFORMATION: Description of Unknown:
      Polyglutamic acid docking site

<400> SEQUENCE: 214

Glu Glu Glu Glu Glu Glu Glu Glu Cys
1               5

<210> SEQ ID NO 215
<211> LENGTH: 10
<212> TYPE: PRT
<213> ORGANISM: Unknown
<220> FEATURE:
<223> OTHER INFORMATION: Description of Unknown:
      Polyglutamic acid docking site

<400> SEQUENCE: 215

Cys Glu Glu Glu Glu Glu Glu Glu Glu Cys
1               5                   10

<210> SEQ ID NO 216
<211> LENGTH: 10
<212> TYPE: PRT
<213> ORGANISM: Epstein Barr virus

<400> SEQUENCE: 216

Leu Leu Asp Arg Val Arg Phe Met Gly Val
1               5                   10

<210> SEQ ID NO 217
```

```
<211> LENGTH: 12
<212> TYPE: PRT
<213> ORGANISM: Epstein Barr virus
<220> FEATURE:
<221> NAME/KEY: MISC_FEATURE
<222> LOCATION: (1)..(1)
<223> OTHER INFORMATION: May or may not be present
<220> FEATURE:
<221> NAME/KEY: MISC_FEATURE
<222> LOCATION: (11)..(12)
<223> OTHER INFORMATION: May or may not be present

<400> SEQUENCE: 217

Lys Gly Ile Leu Gly Phe Val Phe Thr Leu Thr Val
1               5                   10

<210> SEQ ID NO 218
<211> LENGTH: 9
<212> TYPE: PRT
<213> ORGANISM: Chicken pox virus

<400> SEQUENCE: 218

Ser Leu Pro Arg Ser Arg Thr Pro Ile
1               5

<210> SEQ ID NO 219
<211> LENGTH: 9
<212> TYPE: PRT
<213> ORGANISM: Chicken pox virus

<400> SEQUENCE: 219

Ser Ala Pro Leu Pro Ser Asn Arg Val
1               5

<210> SEQ ID NO 220
<211> LENGTH: 8
<212> TYPE: PRT
<213> ORGANISM: Gallus gallus

<400> SEQUENCE: 220

Ser Ile Ile Asn Phe Glu Lys Leu
1               5

<210> SEQ ID NO 221
<211> LENGTH: 527
<212> TYPE: PRT
<213> ORGANISM: Artificial Sequence
<220> FEATURE:
<223> OTHER INFORMATION: Description of Artificial Sequence: Synthetic
      RG-1 VLP sequence

<400> SEQUENCE: 221

Met Ser Leu Trp Leu Pro Ser Glu Ala Thr Val Tyr Leu Pro Pro Val
1               5                   10                  15

Pro Val Ser Lys Val Val Ser Thr Asp Glu Tyr Val Ala Arg Thr Asn
                20                  25                  30

Ile Tyr Tyr His Ala Gly Thr Ser Arg Leu Leu Ala Val Gly His Pro
            35                  40                  45

Tyr Phe Pro Ile Lys Lys Pro Asn Asn Asn Lys Ile Leu Val Pro Lys
        50                  55                  60

Val Ser Gly Leu Gln Tyr Arg Val Phe Arg Ile His Leu P

```
Arg Leu Val Trp Ala Cys Val Gly Val Glu Val Gly Arg Gly Gln Pro
                100                 105                 110

Leu Gly Val Gly Ile Ser Gly His Pro Leu Leu Asn Lys Leu Asp Asp
            115                 120                 125

Thr Glu Asn Ala Ser Ala Tyr Ala Gln Leu Tyr Lys Thr Cys Lys Gln
        130                 135                 140

Ala Gly Thr Cys Pro Pro Asp Ile Ile Pro Lys Val Ala Asn Ala Gly
145                 150                 155                 160

Val Asp Asn Arg Glu Cys Ile Ser Met Asp Tyr Lys Gln Thr Gln Leu
                165                 170                 175

Cys Leu Ile Gly Cys Lys Pro Pro Ile Gly Glu His Trp Gly Lys Gly
            180                 185                 190

Ser Pro Cys Thr Asn Val Ala Val Asn Pro Gly Asp Cys Pro Pro Leu
        195                 200                 205

Glu Leu Ile Asn Thr Val Ile Gln Asp Gly Asp Met Val Asp Thr Gly
210                 215                 220

Phe Gly Ala Met Asp Phe Thr Thr Leu Gln Ala Asn Lys Ser Glu Val
225                 230                 235                 240

Pro Leu Asp Ile Cys Thr Ser Ile Cys Lys Tyr Pro Asp Tyr Ile Lys
                245                 250                 255

Met Val Ser Glu Pro Tyr Gly Asp Ser Leu Phe Phe Tyr Leu Arg Arg
            260                 265                 270

Glu Gln Met Phe Val Arg His Leu Phe Asn Arg Ala Gly Ala Val Gly
        275                 280                 285

Glu Asn Val Pro Asp Asp Leu Tyr Ile Lys Gly Ser Gly Ser Thr Ala
290                 295                 300

Asn Leu Ala Ser Ser Asn Tyr Phe Pro Thr Pro Ser Gly Ser Met Val
305                 310                 315                 320

Thr Ser Asp Ala Gln Ile Phe Asn Lys Pro Tyr Trp Leu Gln Arg Ala
                325                 330                 335

Gln Gly His Asn Asn Gly Ile Cys Trp Gly Asn Gln Leu Phe Val Thr
            340                 345                 350

Val Val Asp Thr Thr Arg Ser Thr Asn Met Ser Leu Cys Ala Ala Ile
        355                 360                 365

Ser Thr Ser Glu Thr Thr Tyr Lys Asn Thr Asn Phe Lys Glu Tyr Leu
370                 375                 380

Arg His Gly Glu Glu Tyr Asp Leu Gln Phe Ile Phe Gln Leu Cys Lys
385                 390                 395                 400

Ile Thr Leu Thr Ala Asp Val Met Thr Tyr Ile His Ser Met Asn Ser
                405                 410                 415

Thr Ile Leu Glu Asp Trp Asn Phe Gly Leu Gln Pro Pro Pro Gly Gly
            420                 425                 430

Thr Leu Glu Asp Thr Tyr Arg Phe Val Thr Ser Gln Ala Ile Ala Cys
        435                 440                 445

Gln Lys His Thr Pro Pro Ala Pro Lys Glu Asp Pro Leu Lys Lys Tyr
450                 455                 460

Thr Phe Trp Glu Val Asn Leu Lys Glu Lys Phe Ser Ala Asp Leu Asp
465                 470                 475                 480

Gln Phe Pro Leu Gly Arg Lys Phe Leu Leu Gln Ala Gly Leu Lys Ala
                485                 490                 495

Lys Pro Lys Phe Thr Leu Gly Lys Arg Lys Ala Thr Pro Thr Thr Ser
            500                 505                 510

Ser Thr Ser Thr Thr Ala Lys Arg Lys Lys Arg Lys Leu Ser Arg
```

```
                515                 520                 525

<210> SEQ ID NO 222
<211> LENGTH: 20
<212> TYPE: PRT
<213> ORGANISM: Human papillomavirus

<400> SEQUENCE: 222

Gln Leu Tyr Lys Thr Cys Lys Gln Ala Gly Thr Cys Pro Pro Asp Ile
1               5                   10                  15

Ile Pro Lys Val
            20
```